(12) United States Patent
Ziebol et al.

(10) Patent No.: US 10,525,250 B1
(45) Date of Patent: Jan. 7, 2020

(54) INFUSION DEVICE WITH ANTIMICROBIAL PROPERTIES

(71) Applicant: Pursuit Vascular, Inc., Maple Grove, MN (US)

(72) Inventors: Robert J. Ziebol, Shoreview, MN (US); Matthew David Beilke, Plymouth, MN (US)

(73) Assignee: Pursuit Vascular, Inc., Maple Grove, MN (US)

( * ) Notice: Subject to any disclaimer, the term of this patent is extended or adjusted under 35 U.S.C. 154(b) by 0 days.

(21) Appl. No.: 16/404,378

(22) Filed: May 6, 2019

Related U.S. Application Data

(60) Provisional application No. 62/756,967, filed on Nov. 7, 2018.

(51) Int. Cl.
| | | |
|---|---|---|
| *A61M 39/16* | (2006.01) | |
| *A61M 1/28* | (2006.01) | |
| *A61K 31/155* | (2006.01) | |
| *A61K 9/00* | (2006.01) | |
| *A61M 25/00* | (2006.01) | |

(52) U.S. Cl.
CPC ......... *A61M 39/162* (2013.01); *A61K 9/0019* (2013.01); *A61K 31/155* (2013.01); *A61M 1/285* (2013.01); *A61M 2025/0019* (2013.01); *A61M 2205/0205* (2013.01)

(58) Field of Classification Search
CPC ................ A61M 39/161; A61M 1/285; A61M 2025/0019; A61M 2205/0205; A61K 9/0019; A61K 31/155
See application file for complete search history.

(56) References Cited

U.S. PATENT DOCUMENTS

| | | |
|---|---|---|
| 559,697 A | 5/1896 | Tiugti et al. |
| 975,939 A | 11/1910 | William et al. |
| 1,445,642 A | 2/1923 | O'neill |
| 3,262,448 A | 7/1966 | Ring et al. |
| 3,595,241 A | 7/1971 | Sheridan |
| 3,977,517 A | 8/1976 | Kadlecik et al. |
| 4,078,686 A | 3/1978 | Karesh |
| 4,331,783 A | 5/1982 | Stoy |
| 4,337,327 A | 6/1982 | Stoy |
| 4,369,294 A | 1/1983 | Stoy |
| 4,370,451 A | 1/1983 | Stoy |
| 4,379,874 A | 4/1983 | Stoy |
| 4,420,589 A | 12/1983 | Stoy |
| 4,440,207 A | 4/1984 | Genatempo et al. |
| 4,446,967 A | 5/1984 | Halkyard |

(Continued)

FOREIGN PATENT DOCUMENTS

| | | |
|---|---|---|
| CN | 101405042 | 4/2009 |
| CN | 102202716 | 9/2011 |

(Continued)

*Primary Examiner* — Lauren P Farrar
(74) *Attorney, Agent, or Firm* — Pauly, DeVries Smith & Deffner LLC

(57) ABSTRACT

The present disclosure is directed to an infusion device and method for preventing infection and microbial ingress in medical device connections. The infusion device comprising a male connector, the male connector comprising a male luer having an antimicrobial agent. In certain implementations the male luer comprises a tapered sealing member further comprising a recess containing chlorhexidine acetate.

30 Claims, 70 Drawing Sheets

(56) References Cited

U.S. PATENT DOCUMENTS

| | | |
|---|---|---|
| 4,559,043 A | 12/1985 | Whitehouse et al. |
| 4,624,664 A | 11/1986 | Peluso et al. |
| 4,631,188 A | 12/1986 | Stoy et al. |
| 4,705,790 A | 11/1987 | Hubele et al. |
| 4,769,013 A | 9/1988 | Lorenz et al. |
| 4,808,158 A | 2/1989 | Kreuzer et al. |
| 4,889,255 A | 12/1989 | Schiemann et al. |
| 4,894,056 A | 1/1990 | Bommarito |
| 5,015,238 A | 5/1991 | Solomon et al. |
| 5,071,413 A | 12/1991 | Utterberg |
| 5,154,920 A | 10/1992 | Flesher et al. |
| 5,240,675 A | 8/1993 | Wilk et al. |
| 5,297,310 A | 3/1994 | Cox et al. |
| 5,330,899 A | 7/1994 | Devaughn et al. |
| 5,337,730 A | 8/1994 | Maguire |
| 5,366,505 A | 11/1994 | Farber |
| 5,370,640 A | 12/1994 | Kolff |
| 5,375,589 A | 12/1994 | Bhatta |
| 5,407,807 A | 4/1995 | Markus |
| 5,409,012 A | 4/1995 | Sahatjian |
| 5,628,733 A | 5/1997 | Zinreich et al. |
| 5,782,808 A | 7/1998 | Folden |
| 5,902,631 A | 5/1999 | Wang et al. |
| 5,951,519 A | 9/1999 | Utterberg |
| 6,045,623 A | 4/2000 | Cannon |
| 6,059,107 A | 5/2000 | Nøsted et al. |
| 6,071,413 A | 6/2000 | Dyke |
| 6,105,812 A | 8/2000 | Riordan |
| 6,183,450 B1 | 2/2001 | Lois |
| 6,232,406 B1 | 5/2001 | Stoy |
| 6,237,800 B1 | 5/2001 | Barrett et al. |
| 6,409,716 B1 | 6/2002 | Sahatjian et al. |
| 6,444,318 B1 | 9/2002 | Guire et al. |
| 6,468,259 B1 | 10/2002 | Djokic et al. |
| 6,605,294 B2 | 8/2003 | Sawhney |
| 6,605,751 B1 | 8/2003 | Gibbins et al. |
| 6,634,498 B2 | 10/2003 | Kayerød et al. |
| 6,725,492 B2 | 4/2004 | Moore et al. |
| 7,097,850 B2 | 8/2006 | Chappa et al. |
| 7,195,615 B2 | 3/2007 | Tan |
| 7,442,402 B2 | 10/2008 | Chudzik et al. |
| 7,922,701 B2 | 4/2011 | Buchman |
| 8,146,757 B2 | 4/2012 | Abreu et al. |
| 8,500,717 B2 | 8/2013 | Becker |
| 8,622,995 B2 | 1/2014 | Ziebol et al. |
| 8,622,996 B2 | 1/2014 | Ziebol et al. |
| 9,022,984 B2 | 5/2015 | Ziebol et al. |
| 9,072,868 B2 | 7/2015 | Ziebol et al. |
| 9,078,992 B2 | 7/2015 | Ziebol et al. |
| 9,352,142 B2 | 5/2016 | Ziebol et al. |
| 9,809,355 B2 | 11/2017 | Solomon et al. |
| 9,849,276 B2 | 12/2017 | Ziebol et al. |
| 10,159,829 B2 | 12/2018 | Ziebol et al. |
| 2004/0034329 A1 | 2/2004 | Mankus et al. |
| 2004/0156908 A1 | 8/2004 | Polaschegg et al. |
| 2005/0098527 A1 | 5/2005 | Yates et al. |
| 2005/0124970 A1 | 6/2005 | Kunin et al. |
| 2005/0171493 A1 | 8/2005 | Nicholls |
| 2005/0220882 A1 | 10/2005 | Pritchard et al. |
| 2005/0267421 A1 | 12/2005 | Wing |
| 2005/0288551 A1 | 12/2005 | Callister et al. |
| 2006/0024372 A1 | 2/2006 | Utterberg et al. |
| 2006/0206178 A1 | 9/2006 | Kim |
| 2007/0202177 A1 | 8/2007 | Hoang |
| 2008/0132880 A1 | 6/2008 | Buchman |
| 2008/0172007 A1 | 7/2008 | Bousquet |
| 2008/0319423 A1 | 12/2008 | Tanghoj et al. |
| 2009/0062766 A1 | 3/2009 | Howlett et al. |
| 2009/0137969 A1 | 5/2009 | Colantonio et al. |
| 2009/0205151 A1 | 8/2009 | Fisher et al. |
| 2009/0247485 A1 | 10/2009 | Ahmed et al. |
| 2010/0106102 A1 | 4/2010 | Ziebol et al. |
| 2010/0106103 A1 | 4/2010 | Ziebol et al. |
| 2010/0143427 A1 | 6/2010 | King et al. |
| 2011/0030726 A1 | 2/2011 | Vaillancourt et al. |
| 2012/0022469 A1 | 1/2012 | Alpert et al. |
| 2013/0039953 A1 | 2/2013 | Dudnyk et al. |
| 2013/0134161 A1 | 5/2013 | Fogel et al. |
| 2013/0144258 A1 | 6/2013 | Ziebol et al. |
| 2013/0184679 A1 | 7/2013 | Ziebol et al. |
| 2013/0204231 A1* | 8/2013 | Ziebol .................... A61L 2/186 604/508 |
| 2013/0274686 A1 | 10/2013 | Ziebol et al. |
| 2014/0042116 A1 | 2/2014 | Shen et al. |
| 2014/0228775 A1* | 8/2014 | Burkholz .......... A61M 25/0097 604/244 |
| 2015/0343174 A1 | 12/2015 | Ziebol et al. |
| 2016/0001058 A1 | 1/2016 | Ziebol et al. |
| 2018/0200500 A1 | 7/2018 | Ziebol et al. |

FOREIGN PATENT DOCUMENTS

| | | |
|---|---|---|
| CN | 103796704 | 12/2016 |
| CN | 106902402 | 6/2017 |
| CN | 106902405 | 6/2017 |
| DE | 3515665 | 5/1986 |
| EP | 1442753 | 2/2007 |
| EP | 1813293 | 8/2007 |
| WO | 2006102756 | 10/2006 |
| WO | 2010062589 | 7/2010 |
| WO | 2013009998 | 1/2013 |

* cited by examiner

← DISTAL DIRECTION          PROXIMAL DIRECTION →

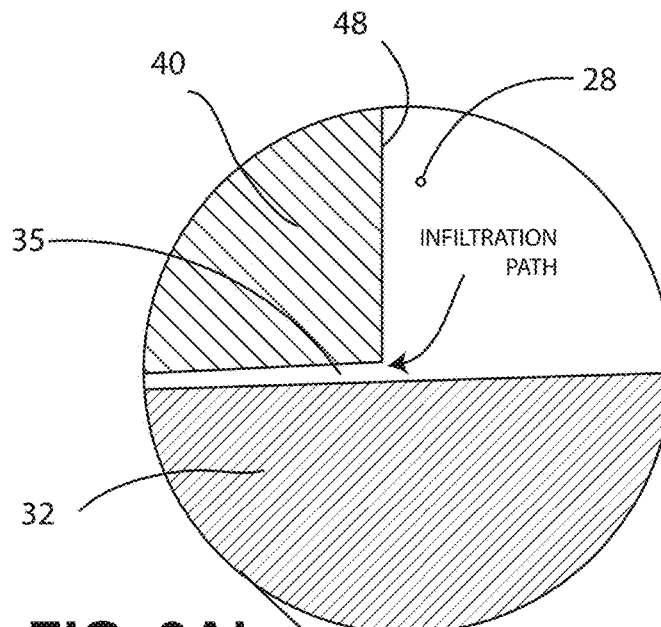
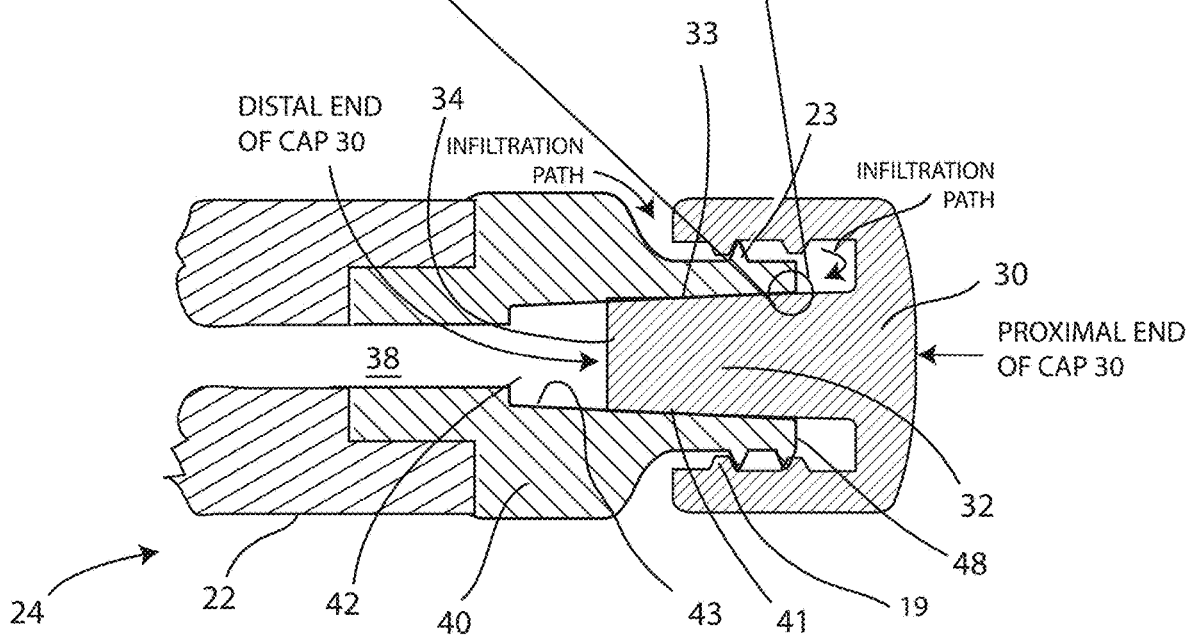

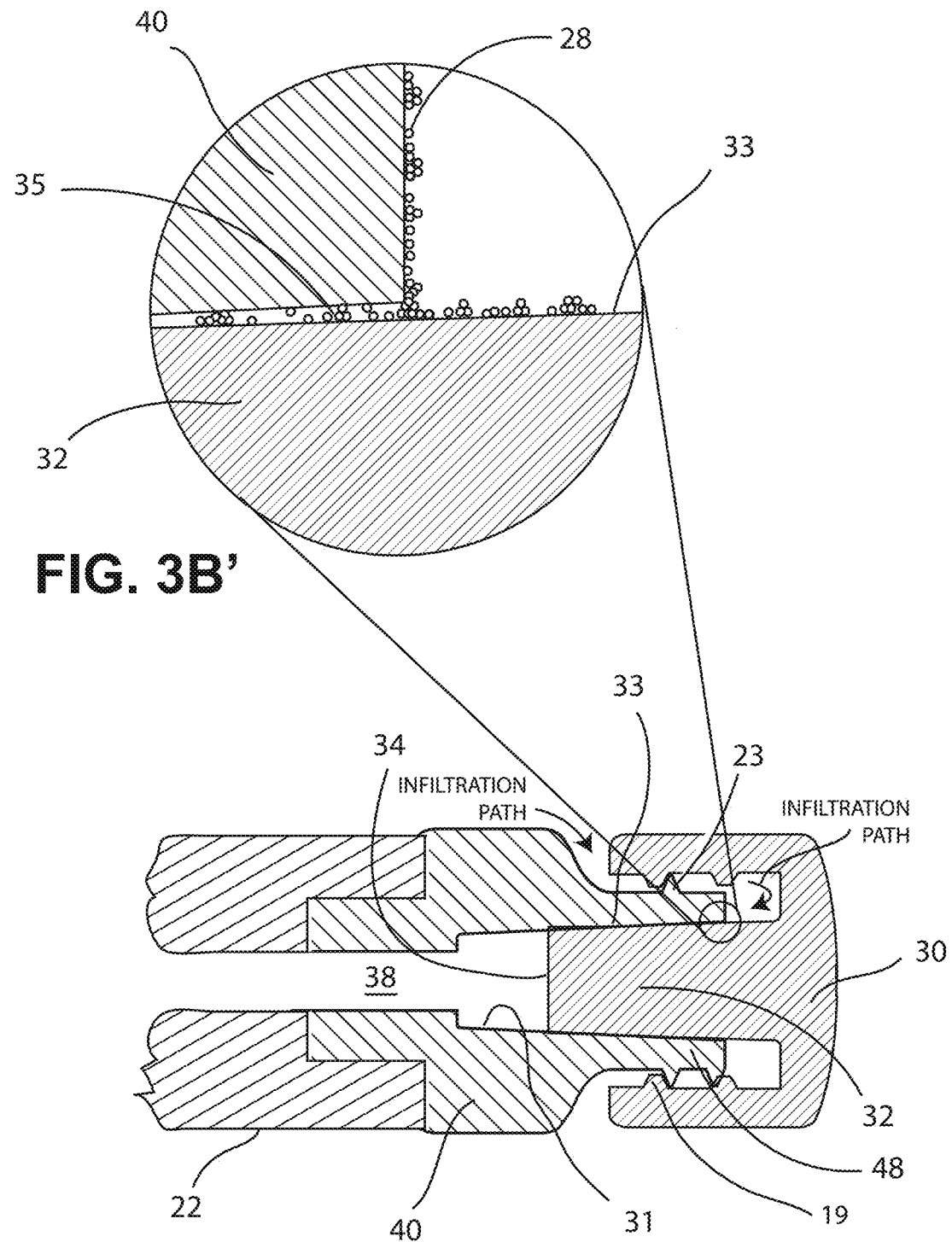

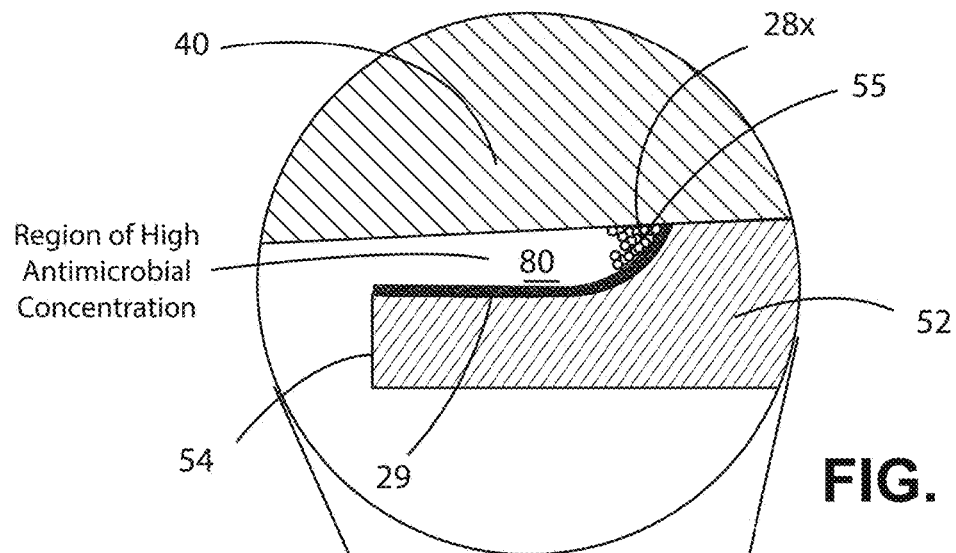
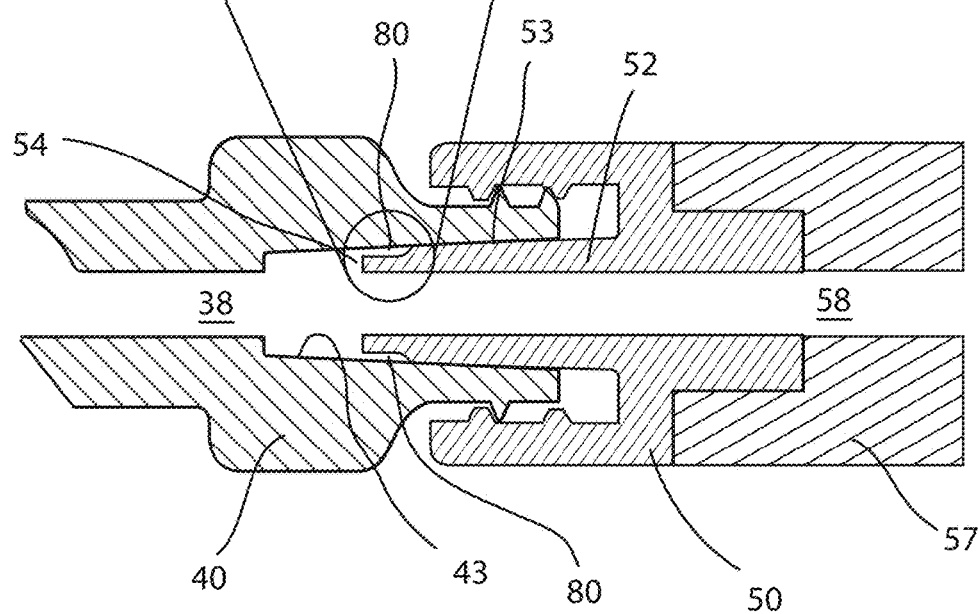
FIG. 7B

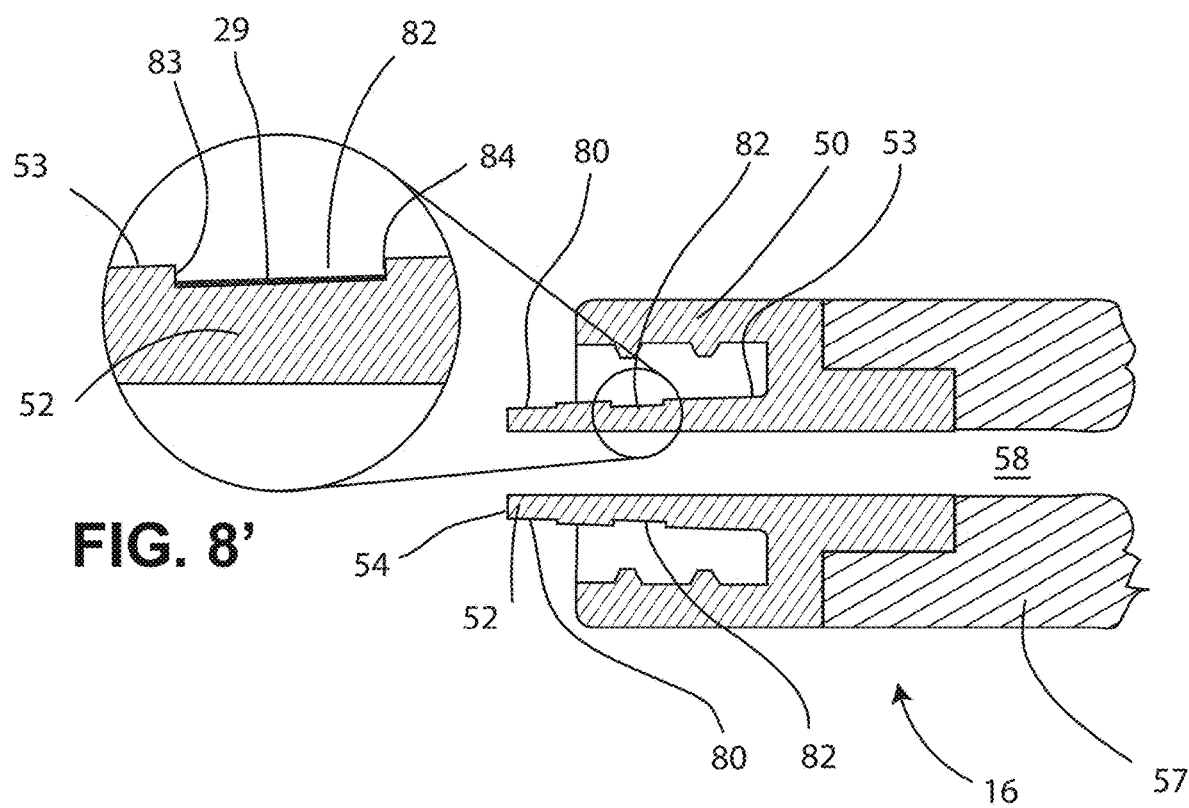

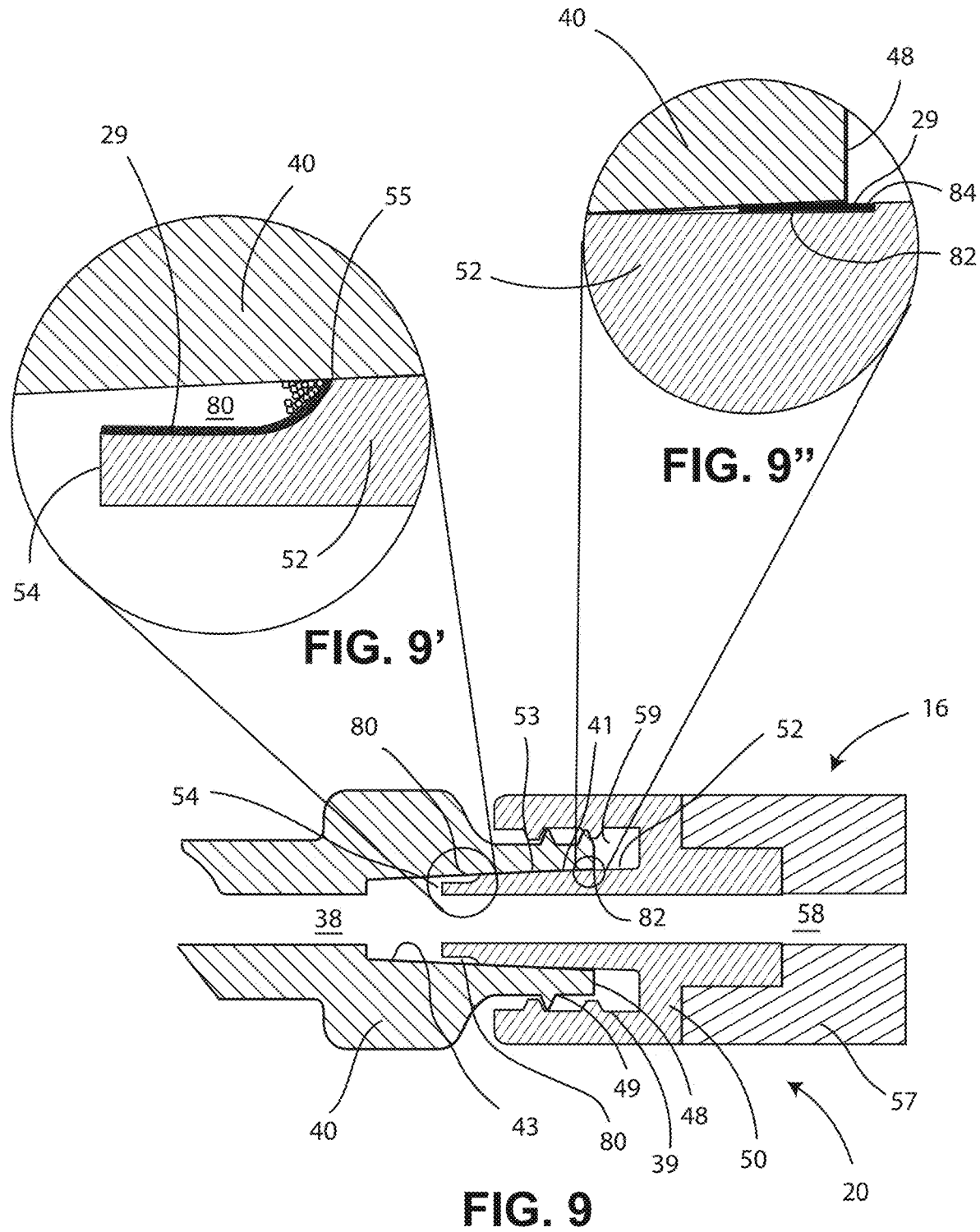

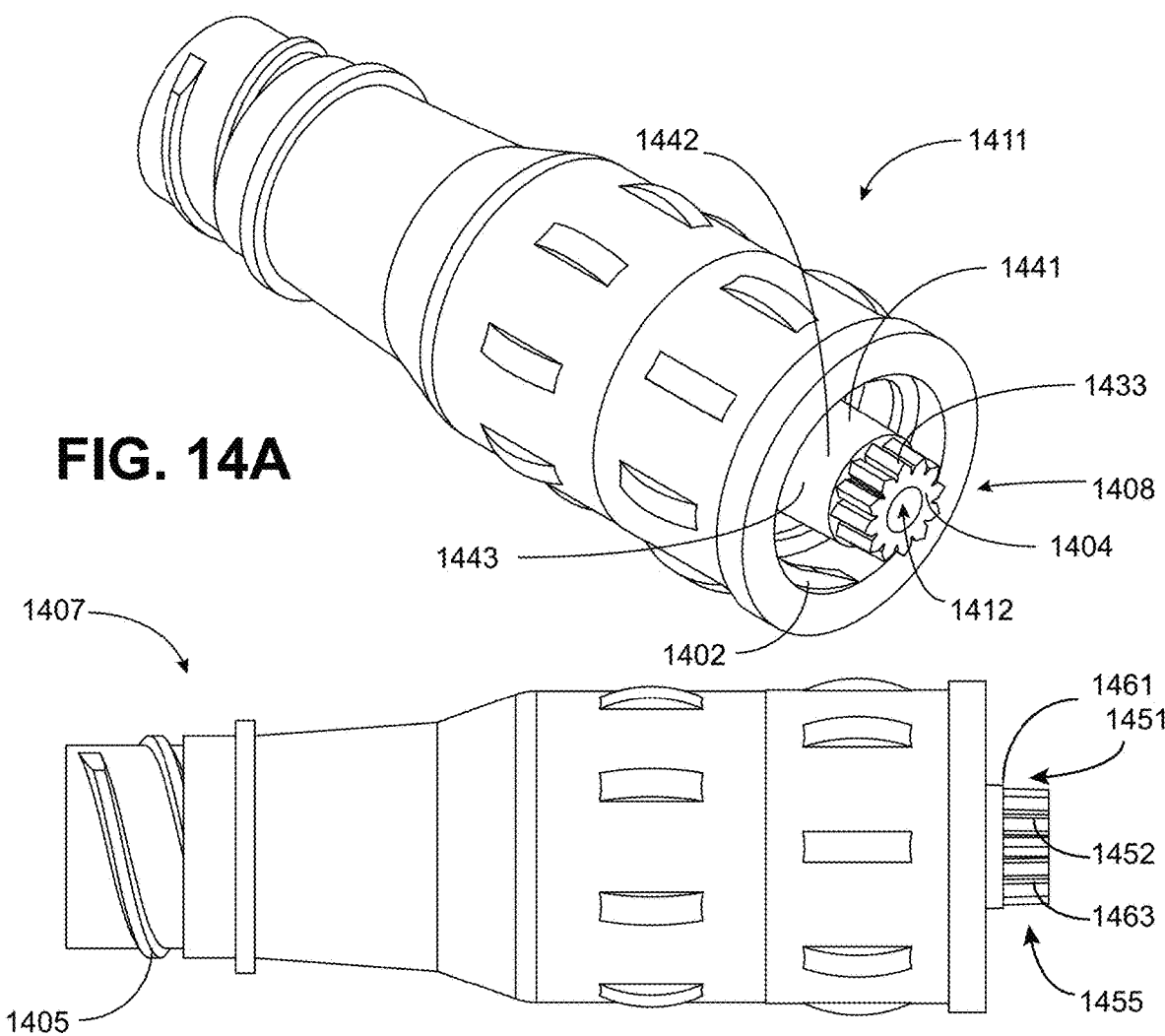
FIG. 14A
FIG. 14B
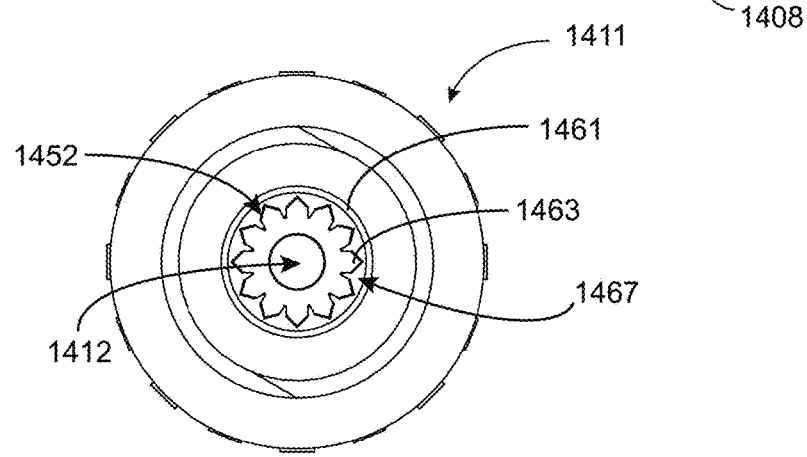
FIG. 14C

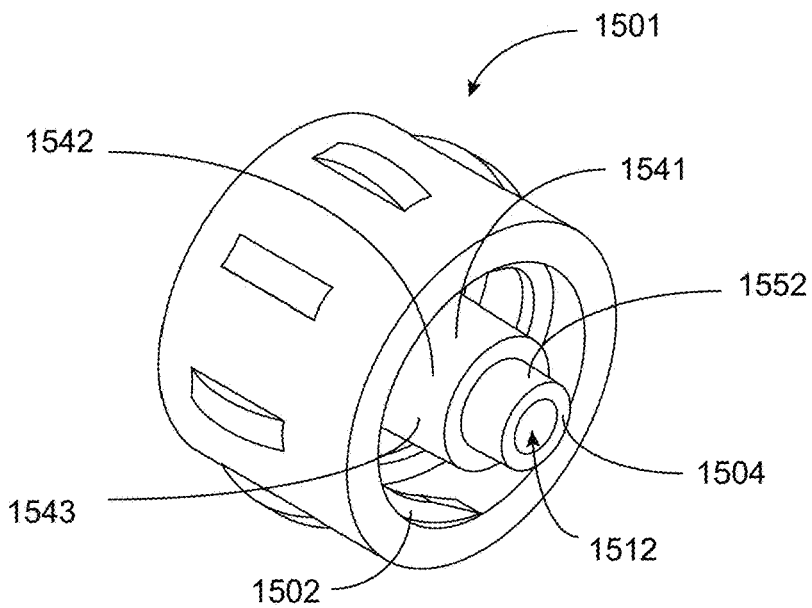
FIG. 15A
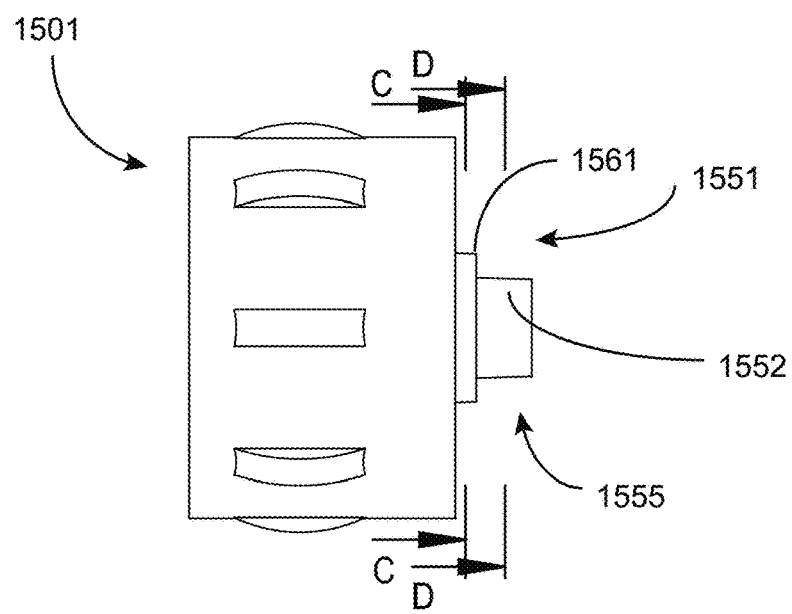
FIG. 15B
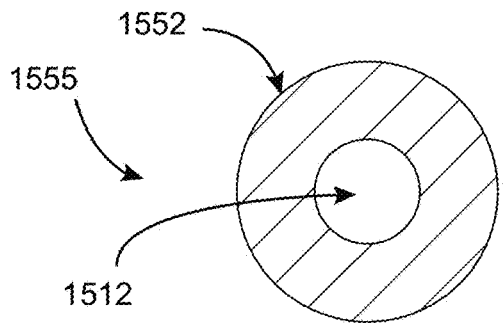 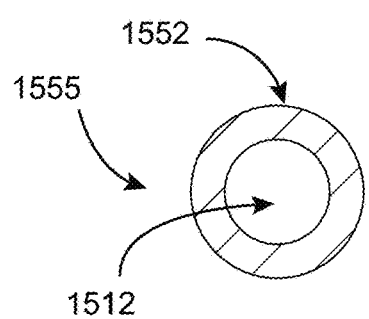
FIG. 15C      FIG. 15D

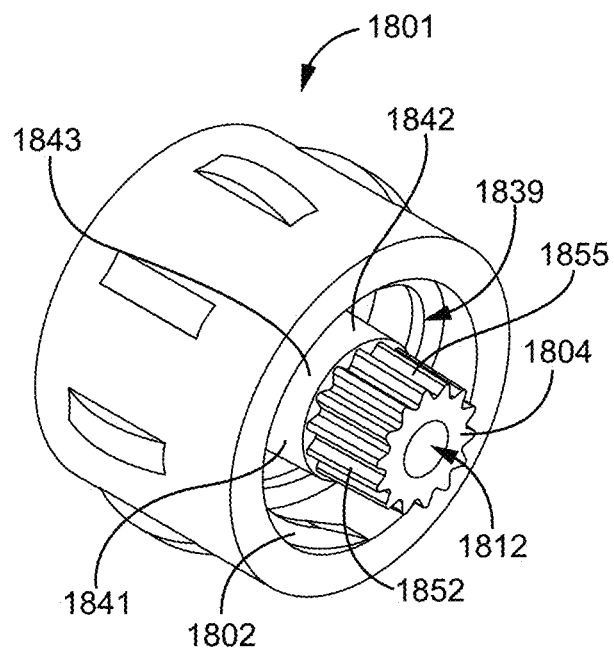
FIG. 18A
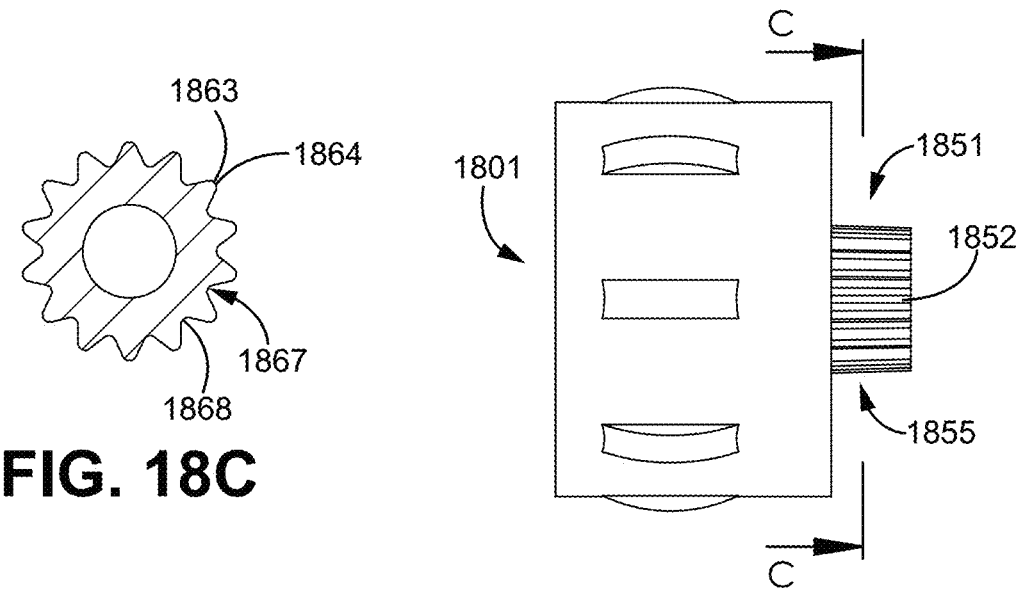
FIG. 18C
FIG 18B

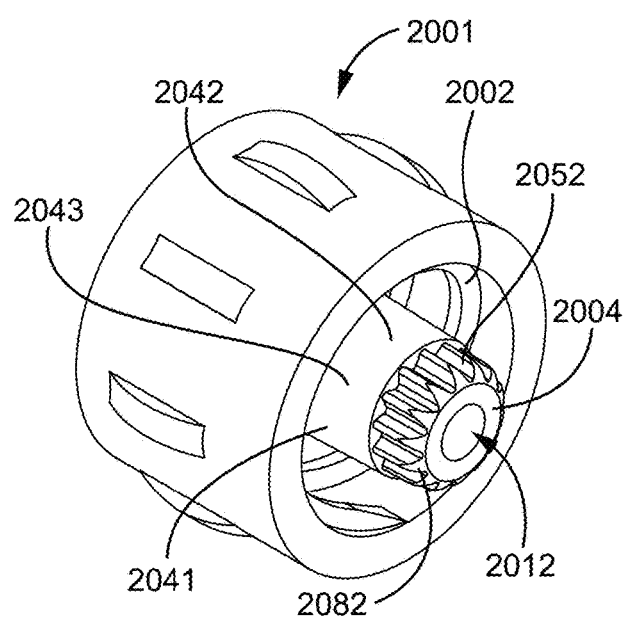
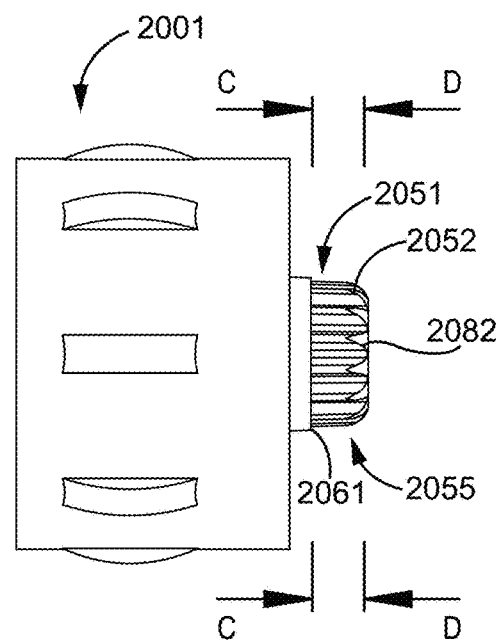
FIG. 20A  FIG. 20B
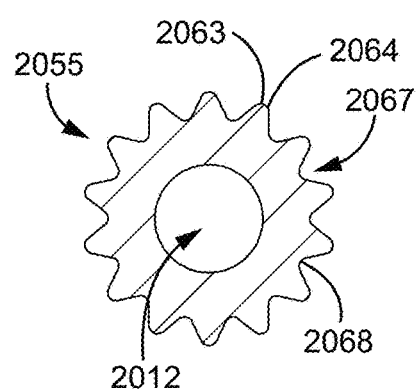
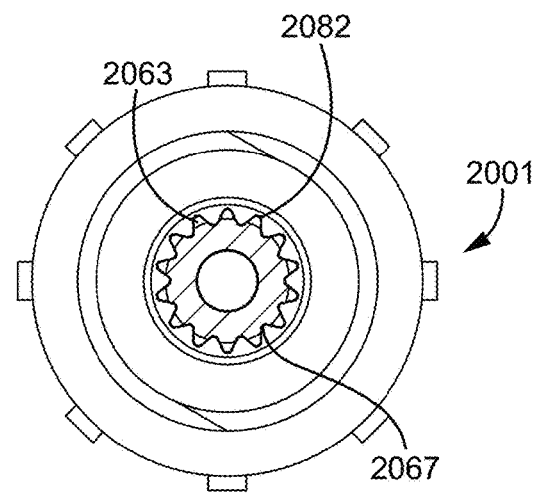
FIG. 20C  FIG. 20D

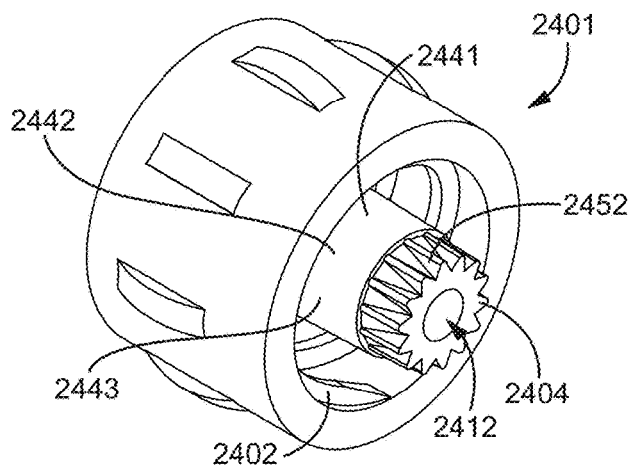
FIG. 24A
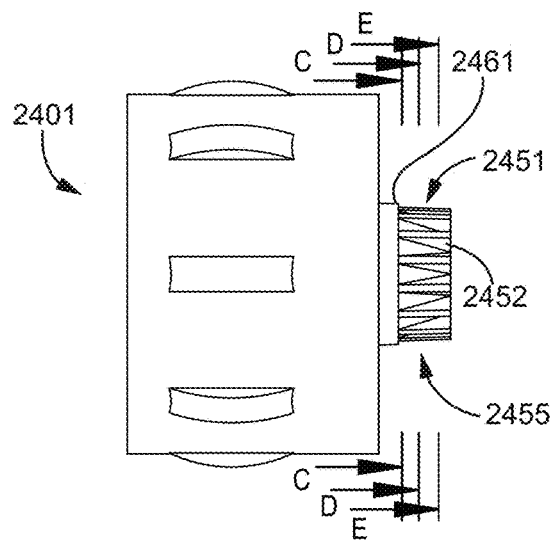
FIG. 24B
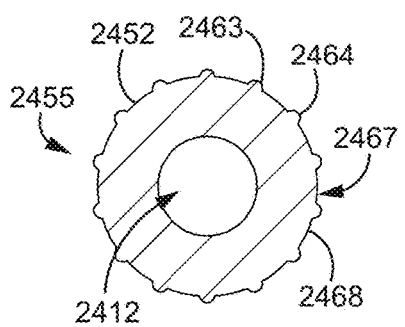 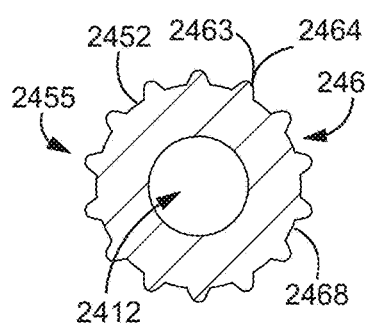 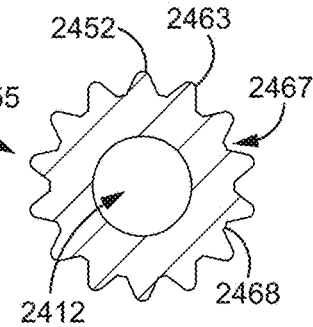
FIG. 24C  FIG. 24D  FIG. 24E

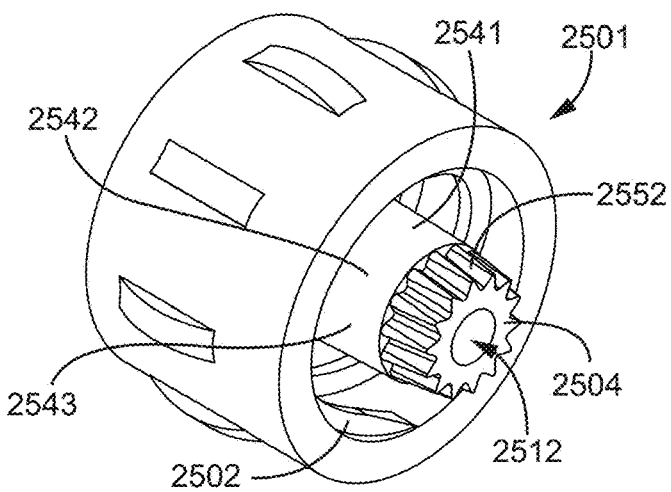
FIG. 25A
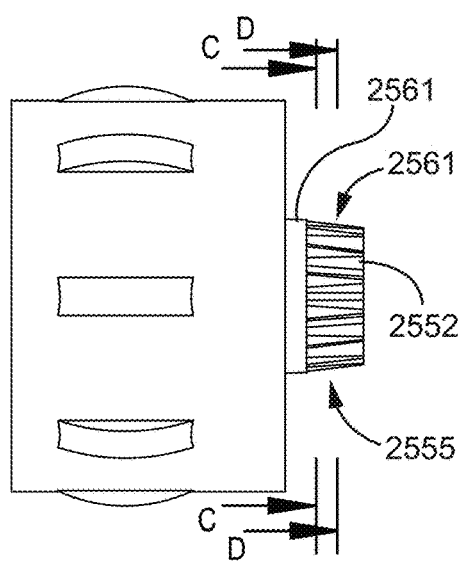
FIG. 25B
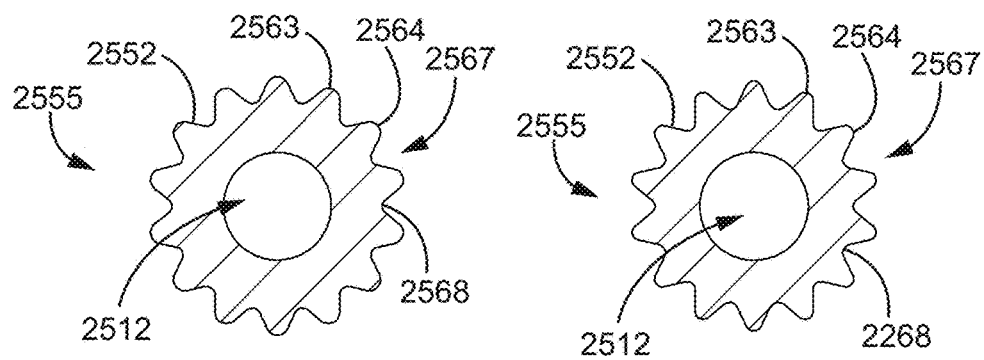
FIG. 25C  FIG. 25D

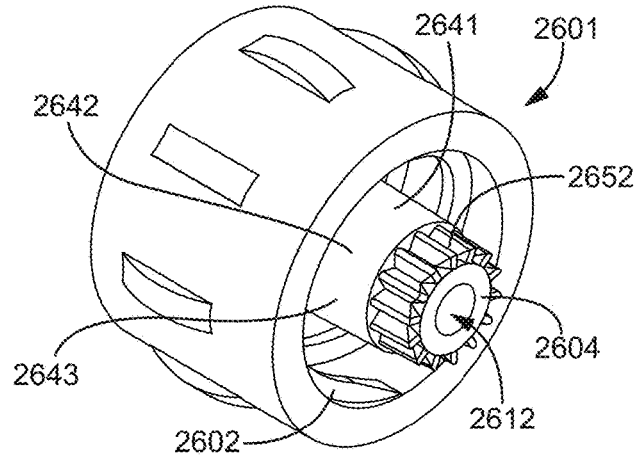
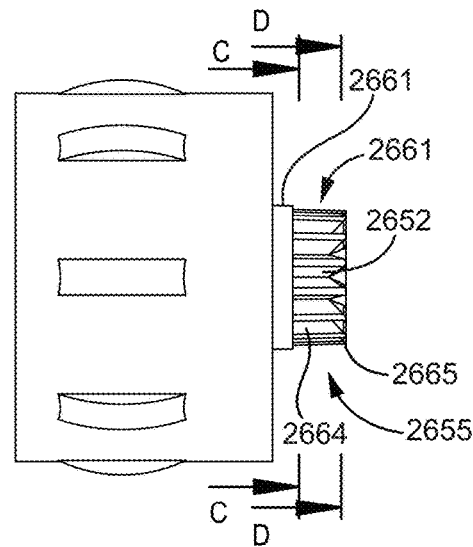
FIG. 26A  FIG. 26B
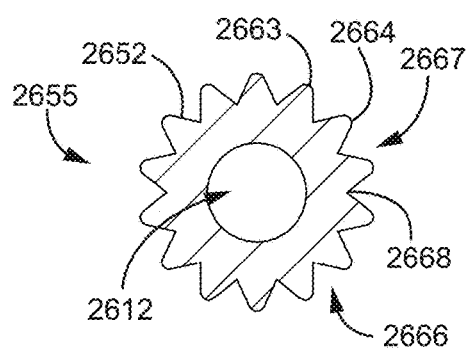
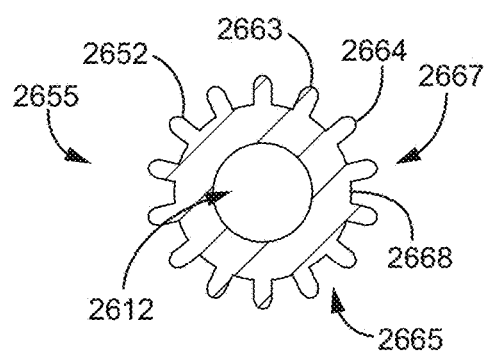
FIG. 26C  FIG. 26D

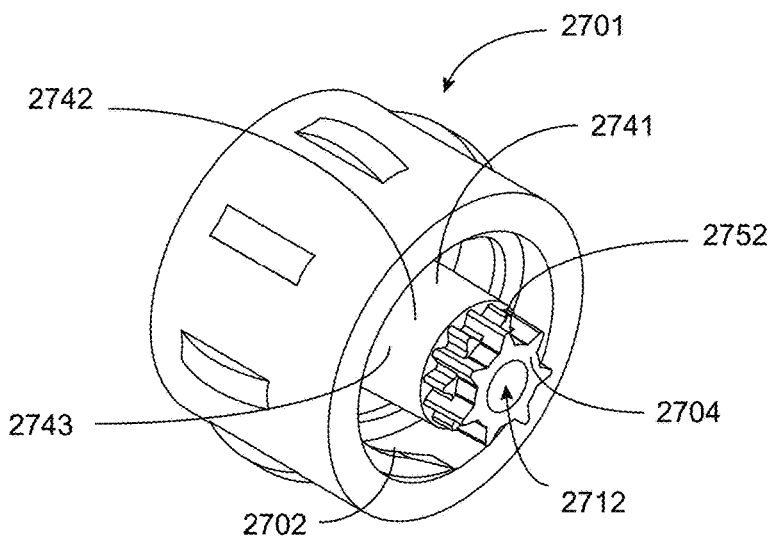
FIG. 27A
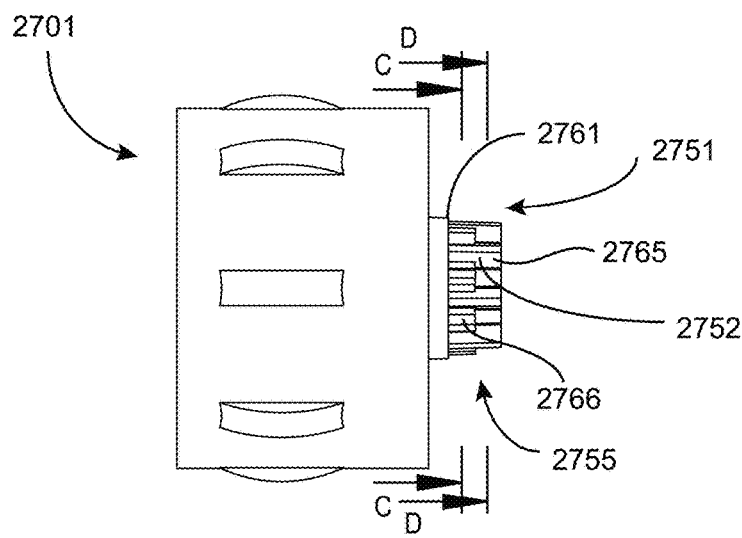
FIG. 27B
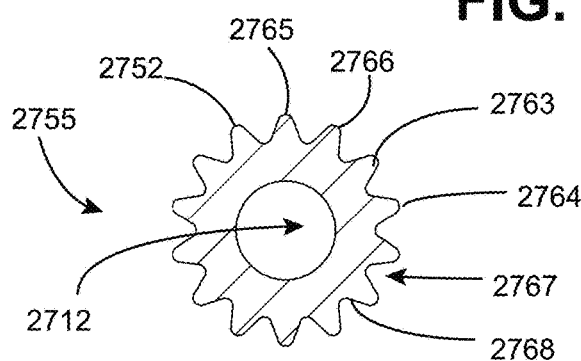 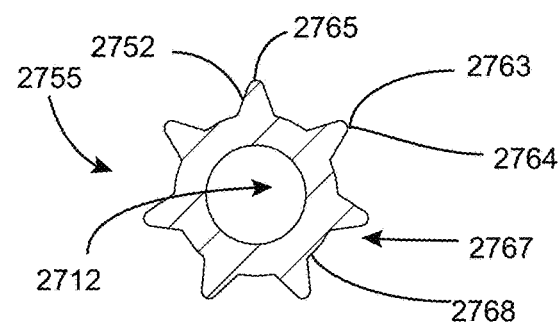
FIG. 27C  FIG. 27D

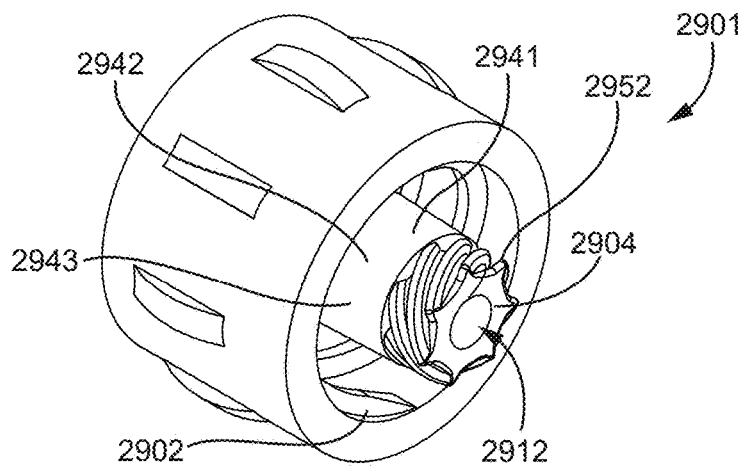
FIG. 29A
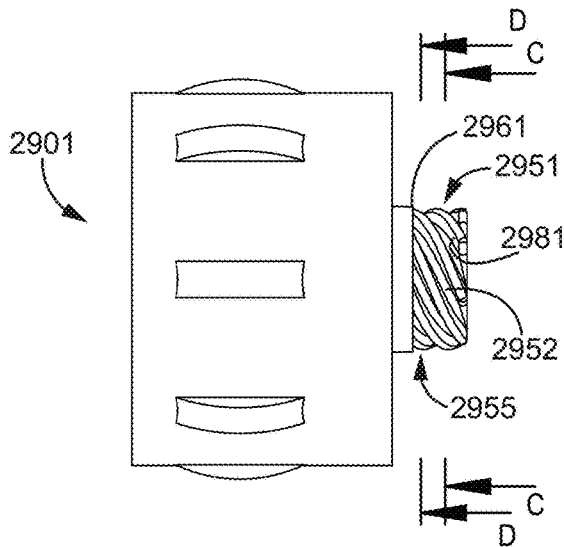
FIG. 29B
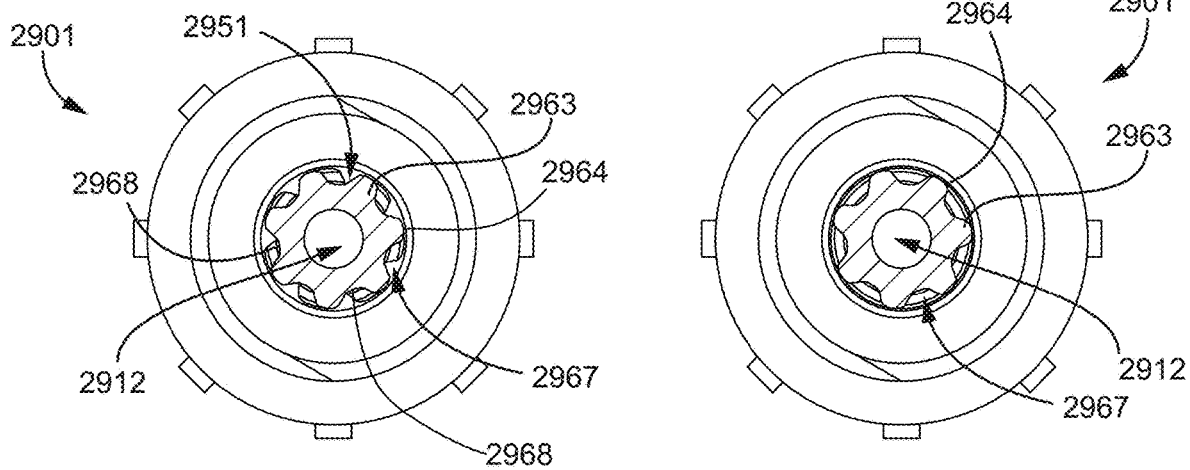
FIG. 29C  FIG. 29D

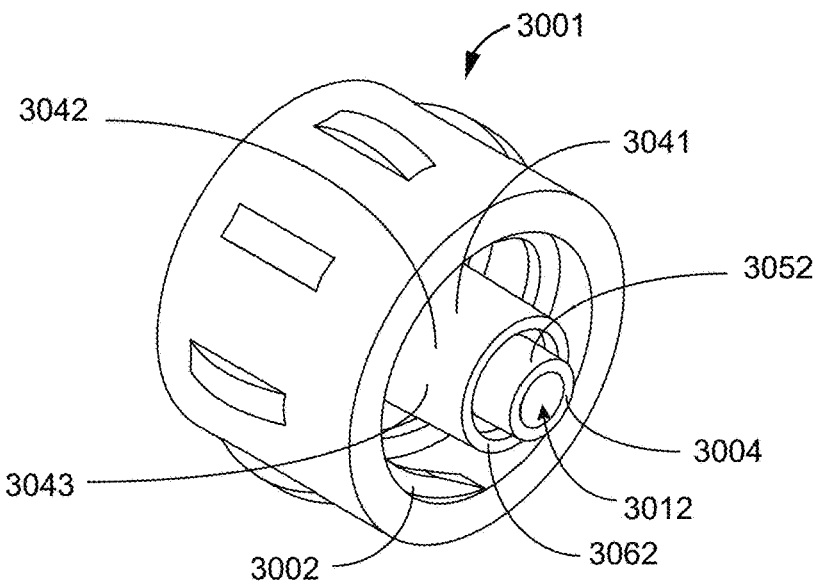
FIG. 30A
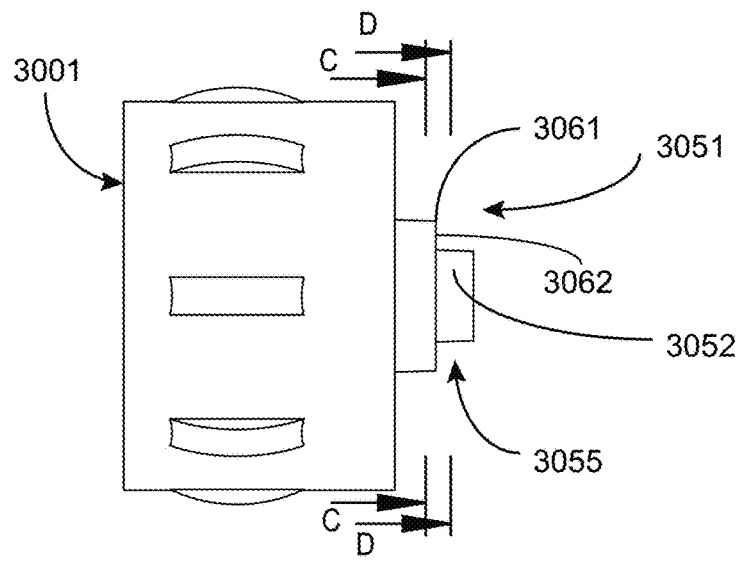
FIG. 30B
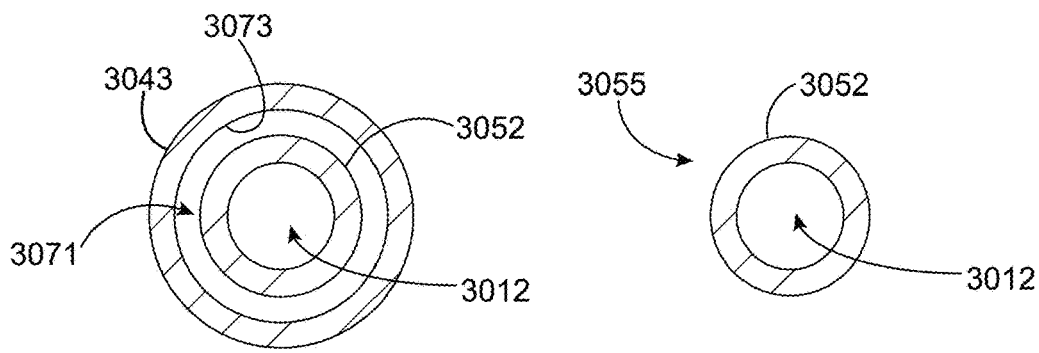
FIG. 30C      FIG. 30D

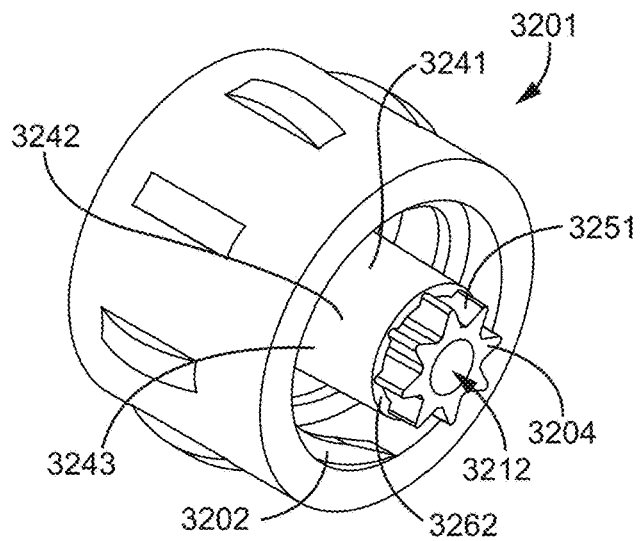
FIG. 32A
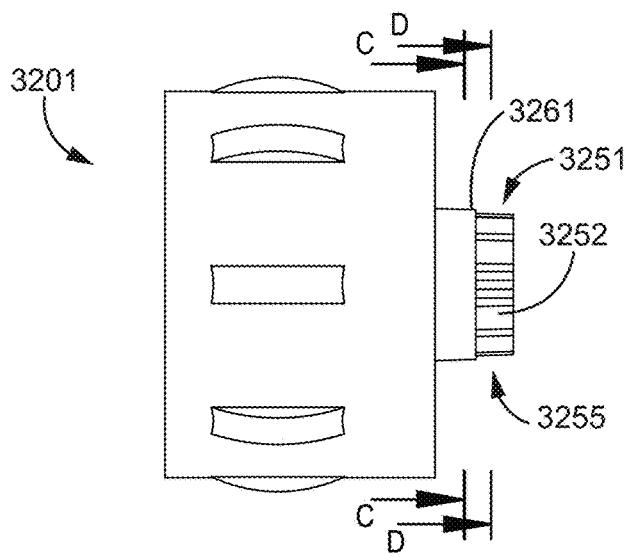
FIG. 32B
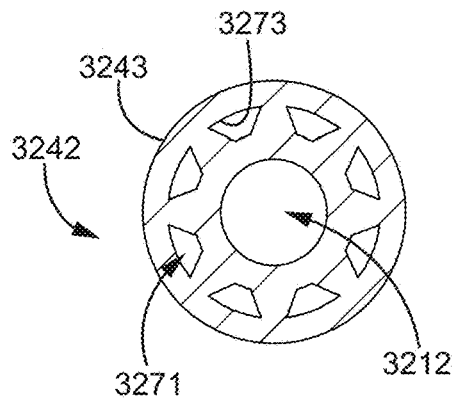 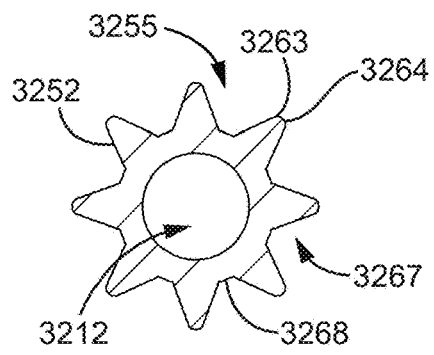
FIG. 32C    FIG. 32D

INFUSION DEVICE WITH ANTIMICROBIAL PROPERTIES

This application claims the benefit of U.S. Provisional Application No. 62/756,967, filed Nov. 7, 2018, the contents of which are herein incorporated by reference.

FIELD

The present disclosure relates to medical devices, systems, and methods for killing infection-causing organisms and providing in-situ antimicrobial properties.

BACKGROUND

Infusion devices, such as catheters and on-catheter devices, are commonly used in providing modern medical care to patients. For example, catheters such as hemodialysis catheters, peritoneal dialysis catheters, peripherally inserted central catheters, midline catheters and drainage catheters are all commonly used in providing modern medical care to patients. Other infusion devices used in providing medical care include needleless connectors, intravenous (IV) administration sets, peritoneal dialysis lines, bloodlines, syringes, valves and filters.

These infusion devices are useful for treating various medical conditions. For example, peritoneal catheters allow patients with renal disease to have waste and fluid removed from their bodies. Thus, catheters and other infusion devices make critical medical care possible and are often essential to providing improved health care outcomes.

However, long-term use of catheters has a serious drawback in that a significant percentage of catheters fail due to infection, resulting in elevated mortality rates and significantly increased healthcare costs associated with treatment. Furthermore, infections are a leading cause of death in the United States, and many of those infections are attributable to infusion devices. The mortality rate associated with such infections is considerable. Therefore, a need exists for a manner to reduce infections relating from the use of infusion devices.

SUMMARY

The present disclosure is directed, in part, to infusion devices comprising a coupling, the coupling typically comprising both a male connector or cap and a female connector, wherein the male connector or cap comprises an antimicrobial. In certain implementations the male connector or cap comprises a male luer that inserts into a female luer. The male luer typically includes a tapered surface, such as a male luer commonly used in medical devices. In certain implementations the male connector or cap comprises a male luer with a tapered sealing surface having a truncated conical geometry. In certain implementations the male connector or cap comprises a male luer with a tapered sealing surface having a non-conical geometry.

Infection-causing organisms are ever present in the environment; and they live on patients' skin and can survive and be transmitted in air and water. Conventional medical device connectors and caps, such as male and female connectors with tapered luers, contain a threaded region along with a tapered sealing region, such as an overlapping sealing region of the tapered portions of male and female connectors. The overlapping sealing regions seal fluid inside the medical device and keeps air and organisms out. However, our testing shows that organisms can still migrate through the threaded region and penetrate a portion of the way into the sealing region. This results in organisms being present along the walls of the tapered portions of the male and female luers within a thin interstitial space of the sealing region. When the male and female connectors are separated from one another some organisms can remain on the walls of the male and female connectors, including on tapered portions of male luer and female luer of the male and female connectors that previously formed a seal. The next time a connection is made some of the organisms on the wall of the female luer can be pushed past the sealing surface and into the fluid path (during insertion of the male luer into the female luer). Once organisms are in the fluid path they can multiply, spread, and cause an infection.

The walls of the male luer and female luer are typically tapered, or at least partially tapered, and may also become contaminated by airborne organisms landing on the surface or through touch contamination. Upon inserting the male luer into the female luer the organisms can be pushed into the fluid path where they can also multiply, spread and cause an infection.

A catheter is generally a tubular construction, thus catheters can be characterized as a "medical tube". Similarly, other infusion devices can also be characterized as "medical tubes"

In certain aspects of the subject matter described herein, the distal end of the male luer, as well as intermediate portions (portions between the distal and proximal ends) of the male luer, contain an antimicrobial. As used herein, the terms "proximal" end and "distal end" are used to refer to the relative positions on an article. With regard to a catheter, for example, the proximal end is that end closest to a person servicing the catheter female connector, while the distal end is closest to a patient. For example, the distal end of a hemodialysis catheter will be inside a patient, while the proximal end will be outside the patient and have a female luer on a female connector. Similarly, the proximal end of a male cap containing a male luer will be outside of the female connector when coupled to the female connector, while the distal end of the male cap will be inside the female connector when coupled to the female connector. As will be discussed later, FIGS. 2 and 3A show directional arrows depicting the distal direction and the proximal direction (an intermediate location would be between the distal and proximal directions). FIG. 3A further shows a male cap 30 with the proximal and distal ends of the cap labeled. Thus "proximal" and "distal" are relative terms, showing the position relative to the patient and ends of a device.

The present disclosure includes a method for delivering an antimicrobial composition into an infusion device, the method comprising: inserting a male connector having a male tapered surface into a female connector of the infusion device, the female connector having a female tapered surface, such that the male tapered surface engages the female tapered surface to form a fluid-tight seal, the male connector having: i) a distal tip; ii) a recess proximal to the distal tip, the recess having a recess surface radially inward of a line of taper extending distally along the male tapered surface at a first taper angle relative to a central longitudinal axis of the male connector; and iii) a water-soluble antimicrobial composition positioned on the recess surface; wherein upon insertion of the male connector into the female connector a cavity is formed between the recess surface and the female tapered surface, and a fluid inside the infusion device at least partially fills the cavity and at least a portion of the antimicrobial composition is dispersed within the fluid in the cavity.

The present disclosure is directed to a method for delivering an antimicrobial composition into an infusion device, the method comprising: inserting a male connector having a male tapered surface into a female connector of the infusion device, the female connector having a female tapered surface, such that the male tapered surface engages the female tapered surface to form a substantially fluid-tight seal, the male connector having: i) a distal tip; ii) a recess surface proximal to the distal tip, wherein the recess surface is radially inward of a line of taper extending along, and distal of, the male tapered surface at a first taper angle relative to a central longitudinal axis of the male connector; and iii) a water-soluble antimicrobial composition positioned on the recess surface; wherein, upon insertion of the male connector into the female connector, a cavity is formed between the recess surface and the female tapered surface, and a fluid inside the infusion device at least partially fills the cavity, and at least a portion of the antimicrobial composition is dispersed within the fluid in the cavity.

In certain embodiments the male connector further comprises a tapered surface distal edge proximal to the distal tip of the male connector, the tapered surface distal edge being at the distal most end of the male tapered surface.

In some embodiments the tapered surface distal edge is proximal to at least part of the recess in the male connector.

In some embodiments the tapered surface distal edge has an outer diameter, the distal tip has an outer diameter, and the outer diameter of the tapered surface distal edge is greater than the outer diameter of the distal tip.

In some embodiments during insertion of the male connector into the female connector the tapered surface distal edge of the male connector contacts the tapered surface of the female connector and tapered surface edge of the male connector and both rotates and moves distally along the female tapered surface.

In some embodiments a fluid flow channel extends through the male connector.

In some embodiments the antimicrobial composition comprises chlorhexidine.

In some embodiments a portion of the antimicrobial composition dissolves into the fluid and forms a chlorhexidine precipitate on a portion of the tapered female surface.

In some embodiments, the chlorhexidine precipitate is formed on a portion of the tapered female surface defining the cavity between the recess surface and female tapered surface.

In some embodiments the distal tip of the male connector has an outer diameter that is less than 95 percent of an inner diameter of a portion of the female tapered surface radially outward of the distal tip.

In some embodiments the cavity defines an annular volume between the male connector and the female connector.

In some embodiments the annular volume is between 1 and 10 micro liters in volume.

In some embodiments a plurality of blades extend radially outward from the male recess surface into the cavity to at least partially divide the cavity.

In some embodiments the first taper angle being equal to a second taper angle of the recess surface relative to the central longitudinal axis.

In some embodiments a proximal trap is included.

In some embodiments the tapered surface distal edge defines a portion of the recess.

In some embodiments a portion of the water-soluble antimicrobial composition is contained within the proximal trap.

A method for delivering an antimicrobial composition into an infusion device is also disclosed, the method comprising: inserting a male connector having a male tapered surface into a female connector of the infusion device, the female connector having a female tapered surface, such that the male tapered surface engages the female tapered surface to form a fluid-tight seal, the male connector having: i) a conical taper defined in part by the male tapered surface; ii) a distal tip having a diameter that is less than 95 percent of the diameter of the female tapered surface immediately adjacent to the distal tip; iii) a recess in the male connector proximal to the distal tip of the male connector, the recess having a recess surface residing inside the conical taper, wherein a proximal portion of the recess further defines a proximal trap; iv) a tapered surface distal edge proximal to the distal tip, the tapered surface distal edge having a diameter greater than the distal tip diameter; v) a fluid flow channel through the male connector; and vi) a water-soluble antimicrobial composition positioned on the recess surface; wherein upon insertion of the male connector into the female connector, an annular cavity is formed between the recess surface and the female tapered surface of the female connector, and a fluid inside the infusion device at least partially fills the annular cavity and at least a portion of the antimicrobial composition is dispersed within the fluid in the annular cavity.

A further disclosed method is a method for delivering an antimicrobial composition into an infusion device, the method comprising: inserting a male connector having a male tapered surface into a female connector of the infusion device, the female connector having a female tapered surface, such that the male tapered surface engages the female tapered surface to form a fluid-tight seal, the male connector having: i) a conical taper defined in part by the male tapered surface; ii) a distal tip having an outer diameter that is less than 95 percent of an inner diameter of the female tapered surface at a point radially outward of the distal tip; iii) a recess surface proximal to the distal tip of the male connector, the recess surface residing inside the conical taper; iv) a tapered surface distal edge proximal to the distal tip, the tapered surface distal edge having an outer diameter greater than the outer diameter of the distal tip; v) a fluid flow channel through the male connector; and vi) a water-soluble antimicrobial composition positioned on the recess surface; wherein upon insertion of the male connector into the female connector, an annular cavity is formed between the recess surface and the female tapered surface of the female connector, and a fluid inside the infusion device at least partially fills the annular cavity, and at least a portion of the antimicrobial composition is dispersed within the fluid in the annular cavity; wherein a proximal portion of the annular cavity is configured to collect microbes.

In some embodiments the annular cavity defines an annular volume between the male connector and the female connector, and wherein a portion of the antimicrobial composition dissolves into the fluid and forms a chlorhexidine precipitate on a portion of the tapered female surface.

In some embodiments a plurality of blades extend radially outward from the recess surface into the annular cavity to at least partially divide the annular cavity.

A method for delivering an antimicrobial composition into an infusion device is also disclosed, the method comprising: inserting a male connector having a male tapered surface into a female connector of an infusion device, the female connector having a female tapered surface, such that the male tapered surface engages the female tapered surface to form a fluid-tight seal, the male connector having: i) a conical taper defined in part by the male tapered surface; ii) a distal tip having a diameter that is less than 95 percent of the diameter of the female tapered surface immediately adjacent to the distal tip; iii) a recess in the male connector proximal to the distal tip, the recess having a recess surface residing inside the conical taper and wherein a proximal portion of the recess further defines a recess; iv) a tapered surface distal edge proximal to the distal tip, the tapered surface distal edge having a radius greater than the distal tip radius; v) a fluid flow channel through the male connector; vi) a water-soluble antimicrobial composition positioned on the recess; c) inserting the male connector into the female connector such that the male tapered surface forms a fluid-tight seal with the female tapered surface; wherein upon insertion of the male connector into the female connector an annular cavity is formed between the recess surface and the interior surface of the female connector, the annular cavity having a proximal end and a distal end, a volume between the proximal end and the distal end, a width measured radially, and a length measured axially; wherein the tapered surface distal edge at least partially forms the proximal end of the cavity, and the distal end to the annular cavity has an open face with radial width less than 50 percent of the axial depth of the cavity; wherein the length of the annular cavity is at least twice the width of the annular cavity; and wherein a fluid inside the infusion device at least partially fills the cavity and at least a portion of the antimicrobial composition is dispersed within the fluid in the cavity. In some embodiments a proximal trap is included.

A further embodiment is directed to a method for delivering an antimicrobial composition into an infusion device, the method comprising: inserting a male connector having a male tapered surface into a female connector of an infusion device, the female connector having a female tapered surface, such that the male tapered surface engages the female tapered surface to form a fluid-tight seal, the male connector having: i) a conical taper defined in part by the male tapered surface; ii) a distal tip having an outer diameter that is less than 95 percent of an inner diameter of the female tapered surface at a point radially outward of the distal tip; iii) a recess surface proximal to the distal tip and inside the conical taper; iv) a tapered surface distal edge proximal to the distal tip, the tapered surface distal edge having a radius greater than a radius of the distal tip; v) a fluid flow channel through the male connector; vi) a water-soluble antimicrobial composition positioned on the recess surface; wherein, upon insertion of the male connector into the female connector, an annular cavity is formed between the recess surface and the female tapered surface of the female connector, the annular cavity having a proximal end and a distal end, a volume between the proximal end and the distal end, a width measured radially, and a length measured axially; wherein the tapered surface distal edge at least partially defines the proximal end of the annular cavity, the distal end of the annular cavity is in fluid communication with a fluid lumen of the infusion device, and the width of the annular cavity is less than 50 percent of the length of the annular cavity; and wherein a fluid inside the infusion device at least partially fills the annular cavity, and at least a portion of the antimicrobial composition is dispersed within the fluid in the annular cavity.

In some embodiments a plurality of blades extend radially outward from the recess surface into the annular cavity to at least partially divide the annular cavity.

In some embodiments a portion of the antimicrobial composition dissolves into the fluid and forms a chlorhexidine precipitate on a portion of the tapered female surface.

A method for delivering an antimicrobial composition into a medical tube having a female connector with a female tapered surface is described, the method comprising inserting a male connector into the female connector such that a male tapered surface of the male connector forms a fluid-tight seal with the female tapered surface, wherein the male connector includes: i) an end face, ii) a radially-outward-facing recess surface proximal to the end face and radially inward of the male tapered surface, iii) a fluid flow channel, and iv) a water-soluble antimicrobial composition on the recess surface, wherein upon insertion of the male connector into the female connector, a cavity is defined by the recess surface and the female tapered surface; and upon inserting the male connector into the infusion device, a fluid at least partially filling the cavity disperses at least a portion of the antimicrobial composition within the fluid in the cavity.

In some embodiments the male connector further comprising a tapered surface distal edge proximal to a distal tip of the male connector. In some embodiments the tapered surface distal edge is proximal to the recess surface in the male connector. In some embodiments a proximal trap is included.

In some embodiments a plurality of blades extend radially outward from the recess surface into the cavity to at least partially divide the cavity.

In some embodiments a portion of the antimicrobial composition dissolves into the fluid and forms a chlorhexidine precipitate on a portion of the tapered female surface.

As used herein, the term "female connector" is used to refer to portions of an infusion device containing a female connector, and the female connector generally includes a void area referred to herein as the "female luer". The void forming the female luer typically has a tapered surface. The female connector also includes immediately surrounding elements, such as a threaded outer portion. The term "female connector" as used herein is also sometimes referred to interchangeably in the medical field as a "female connector", "adapter", "hub", and "fitting" when describing an element containing a female luer. As used herein, the terms "male connector" and "male cap" are used to refer to connectors having a sealing extension called a male luer, and this male luer generally has a tapered surface (although in some implementations only parts of that male luer will be tapered). A male connector has a fluid flow path through it (along its axis), while a male cap is sealed and does not have a fluid flow path through it. Thus, a male connector is meant to allow fluid flow through it while a male cap is meant to form a fluid-tight seal and stop fluid flow within a catheter. In many implementations the male connector and cap will have similar or identical internal geometries, other than a central conduit for fluid flow, and in this disclosure the term "connector" is therefore sometimes used to refer to both a connector with a fluid path through it and a cap that does not have a fluid flow path through it. When describing a specific embodiment, the term "connector" or "cap" may be used to describe a specific embodiment, but this is generally not meant to be limiting.

When describing a mated pair of devices, such as a female connector combined with a male connector, the term "coupling" is used herein. Alternatively, the female connector can be combined with a male cap, which is also a "coupling" as used herein. In summary, as used herein a coupling is a female connector combined with either a male connector or a male cap. A female connector in turn is a portion of an infusion device, and the female connector contains a cavity or volume known as the female luer. This cavity or volume known as the female luer typically has a tapered interior surface. The male connector and male cap each include a sealing extension called a male luer that fits within a female luer. The male luer typically has a tapered outer surface. A seal is formed when the tapered surface of the male luer on the male connector or cap contacts the tapered surface of the female luer of the female connector. When these tapered surfaces are in contact with one another the female connector and male connector or cap combine to form a coupling. This coupling can allow flow between infusion devices (such as when a female connector and male connector combine) or prevent flow (such as when a female connector and male cap combine). In both cases it is highly desirable to have the seal between the female and male luers be constructed so as to prevent ingress of microbes, such as bacteria and fungi.

In certain implementations described herein, the male luer of the male connector or cap delivers antimicrobial to the female luer of the female connector. In one embodiment the male luer has a recess near its distal end, the recess containing an antimicrobial. In certain implementations the male luer comprises a recess in the intermediate portion of its tapered outer surface (between the proximal and distal ends of the tapered outer surface, but still on the tapered portion of the male luer), the recess containing an antimicrobial. In certain implementations the male luer comprises a recessed tip portion (at the distal end of the male luer) and a recessed intermediate portion, with both recesses containing an antimicrobial. In certain implementations the male luer comprises a flat end face at its distal end. In certain implementations the male luer comprises an antimicrobial coating at a distal edge region. In certain implementations the male luer comprises an antimicrobial coating at a distal outer region.

In certain implementations the antimicrobial agent comprises chlorhexidine. In certain implementations the antimicrobial agent comprises chlorhexidine base. In certain implementations the antimicrobial agent comprises chlorhexidine acetate. In certain implementations the antimicrobial agent comprises chlorhexidine gluconate. In certain implementations the antimicrobial agent is a dry coating.

In certain implementations the antimicrobial agent is water soluble at greater than 1 mg/mL. In certain implementations the agent is water soluble at greater than 10 mg/mL. In certain implementations a first antimicrobial agent is water soluble at less than 1 mg/mL and a second antimicrobial is soluble at greater than 10 mg/mL. In certain implementations the antimicrobial agent is impregnated into the luer surface. In certain implementations the antimicrobial agent is a broad-spectrum compound capable of killing gram positive bacteria, gram negative bacteria and fungi. In certain implementations the antimicrobial agent is a nonantibiotic antimicrobial. In certain implementations the antimicrobial agent converts into chlorhexidine dihydrochloride in presence of saline.

In certain implementations the antimicrobial agent comprises silver. In certain implementations the antimicrobial agent comprises silver sulfadiazine. In certain implementations the antimicrobial agent contains more than one compound. In certain implementations the antimicrobial agent comprises chlorhexidine and silver sulfadiazine. In certain implementations the antimicrobial agent comprises the antibiotics minocycline and rifampin.

In certain implementations the antimicrobial agent is applied in a solvent-based coating process. In certain implementations the antimicrobial agent is applied in a spray process. In certain implementations the antimicrobial agent is applied in a dip process. In certain implementations the antimicrobial agent is dispersed in bulk material of an injection molding process. In certain implementations the antimicrobial agent is part of an antimicrobial solution that contains a solvent that swells the device material, which allows the antimicrobial agent to impregnate the device material, where it remains after solvent evaporates.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

BRIEF DESCRIPTION OF THE DRAWINGS

The device may be more completely understood in connection with the following drawings, in which:

FIG. 3A is a cross-sectional sliced view of a proximal end of a peritoneal catheter with a male cap installed on a female connector.

FIG. 3A' is a closeup cross-sectional sliced view of a portion of the proximal end of the peritoneal catheter and the female connector and the male cap of FIG. 3A.

FIG. 3B is a cross-sectional sliced view of the proximal end of the peritoneal catheter with the male cap installed on the female connector of FIG. 3A after microbes have infiltrated along a path.

FIG. 3B' is a closeup cross-sectional sliced view of a portion of the proximal end of the peritoneal catheter, specifically of the female connector, and the male cap of FIG. 3B.

FIG. 3C' is a closeup cross-sectional sliced view of a portion of the proximal end of the peritoneal catheter, including the female connector, of FIG. 3C.

FIG. 3D' is a closeup cross-sectional sliced view of a portion of the proximal end of the peritoneal catheter, including the female connector, of FIG. 3D.

FIG. 3E' is a closeup cross-sectional sliced view of a portion of the proximal end of the peritoneal catheter of FIG. 3E, including a male luer of the male cap.

FIG. 3F' is a closeup cross-sectional sliced view of a portion of the proximal end of the peritoneal catheter with the new male cap installed of FIG. 3F, including the male luer of the male cap.

FIG. 4A' is a closeup cross-sectional sliced view of a portion of the proximal end of the peritoneal catheter with the male cap installed on the female connector of FIG. 4A.

FIG. 4B' is a closeup cross-sectional sliced view of a portion of the proximal end of the peritoneal catheter with the male cap installed of FIG. 4B.

FIG. 4C' is a closeup cross-sectional sliced view of a portion of the proximal end of the peritoneal catheter of FIG. 4C.

FIG. 4D' is a closeup cross-sectional sliced view of a portion of the proximal end of the peritoneal catheter of FIG. 4D.

FIG. 4E' is a closeup cross-sectional sliced view of a portion of the proximal end of the peritoneal catheter, including the female connector, of FIG. 4E.

FIG. 4F' is a closeup cross-sectional sliced view of a portion of the proximal end of the peritoneal catheter with the new male cap installed of FIG. 4F.

FIG. 7A' is a closeup cross-sectional sliced view of a portion of the female connector having the infusion set coupled to it, the infusion set comprising the male connector having the male luer including the distal recess configured for delivery of the antimicrobial agent of FIG. 7A.

FIG. 7B is a partial cross-sectional view of the female connector having the infusion set connected, the infusion set comprising the male luer including the distal recess configured for delivery of the antimicrobial agent of FIG. 7A after a period of time.

FIG. 7B' is a closeup cross-sectional sliced view of a portion of the female connector and the male luer including the distal recess configured for delivery of the antimicrobial agent of FIG. 7B.

FIG. 8 is a partial cross-sectional view of an infusion set, the infusion set including a male connector having a tube connected, the male connector including a male luer having a distal recess and an intermediate recess configured for delivery of an antimicrobial agent.

FIG. 8' is a closeup partial cross-sectional view of the male luer of FIG. 8, showing the intermediate recess configured for delivery of an antimicrobial agent.

FIG. 9 is a partial cross-sectional view of a female connector having an infusion device connected, the infusion device comprising a male luer including a distal recess and an intermediate recess, each recess containing an antimicrobial agent and configured for delivery of the antimicrobial agent.

FIG. 9' is a closeup partial cross-sectional view of the female connector and the male luer of FIG. 9 showing an enlargement of the distal recess of the male luer.

FIG. 9" is a closeup partial cross-sectional view of the female connector and the male luer of FIG. 9 showing an enlargement of a proximal end of the female connector and the intermediate recess of the male luer.

FIG. 13' is an enlarged partial cross-sectional view of the female connector and the male luer of FIG. 13.

FIG. 14A is an isometric view of a needleless connector according to some examples.

FIG. 14B is a side view of the needleless connector of FIG. 14A.

FIG. 14C is an end view of the needleless connector of FIG. 14A.

FIG. 15A is an isometric view of a male luer connector according to some examples.

FIG. 15B is a side view of the male luer connector of FIG. 15A.

FIG. 15C is a cross-sectional view of the male luer connector of FIG. 15A along line C-C of FIG. 15B.

FIG. 15D is a cross-sectional view of the male luer connector of FIG. 15A along line D-D of FIG. 15B.

FIG. 18A is an isometric view of a male luer connector according to some examples.

FIG. 18B is a side view of the male luer connector of FIG. 18A.

FIG. 18C is a cross-sectional view of the male luer connector of FIG. 18A along line C-C of FIG. 18B.

FIG. 20A is an isometric view of a male luer connector according to some examples.

FIG. 20B is a side view of the male luer connector of FIG. 20A.

FIG. 20C is a cross-sectional view of the male luer connector of FIG. 20A along line C-C of FIG. 20B.

FIG. 20D is a cross-sectional view of the male luer connector of FIG. 20A along line D-D of FIG. 20B.

FIG. 24A is an isometric view of a male luer connector according to some examples.

FIG. 24B is a side view of the male luer connector of FIG. 24A according to some examples.

FIG. 24C is a cross-sectional view of the male luer connector of FIG. 24A along line C-C of FIG. 24B according to some examples.

FIG. 24D is a cross-sectional view of the male luer connector of FIG. 24A along line D-D of FIG. 24B according to some examples.

FIG. 24E is a cross-sectional view of the male luer connector of FIG. 24A along line E-E of FIG. 24B according to some examples.

FIG. 25A is an isometric view of a male luer connector according to some examples.

FIG. 25B is a side view of the male luer connector of FIG. 25A.

FIG. 25C is a cross-sectional view of the male luer connector of FIG. 25A along line C-C of FIG. 25B.

FIG. 25D is a cross-sectional view of the male luer connector of FIG. 25A along line D-D of FIG. 25B.

FIG. 26G is a cross-sectional view of the male luer connector of FIG. 26A along line G-G of FIG. 26E.

FIG. 27A is an isometric view of a male luer connector according to some examples.

FIG. 27B is a side view of the male luer connector of FIG. 27A.

FIG. 27C is a cross-sectional view of the male luer connector of FIG. 27A along line C-C of FIG. 27B.

FIG. 27D is a cross-sectional view of the male luer connector of FIG. 27A along line D-D of FIG. 27B.

FIG. 27E is an end view of the male luer connector of FIG. 27A.

FIG. 27F is a cross-sectional view of the male luer connector of FIG. 27A along line F-F of FIG. 27E.

FIG. 27G is a cross-sectional view of the male luer connector of FIG. 27A along line G-G of FIG. 27E.

FIG. 28A is an isometric view of a male luer connector according to some examples.

FIG. 28B is a side view of the male luer connector of FIG. 28A.

FIG. 28C is a cross-sectional view of the male luer connector of FIG. 28A along line C-C of FIG. 28B.

FIG. 28D is an end view of the male luer connector of FIG. 28A.

Figure 28A:
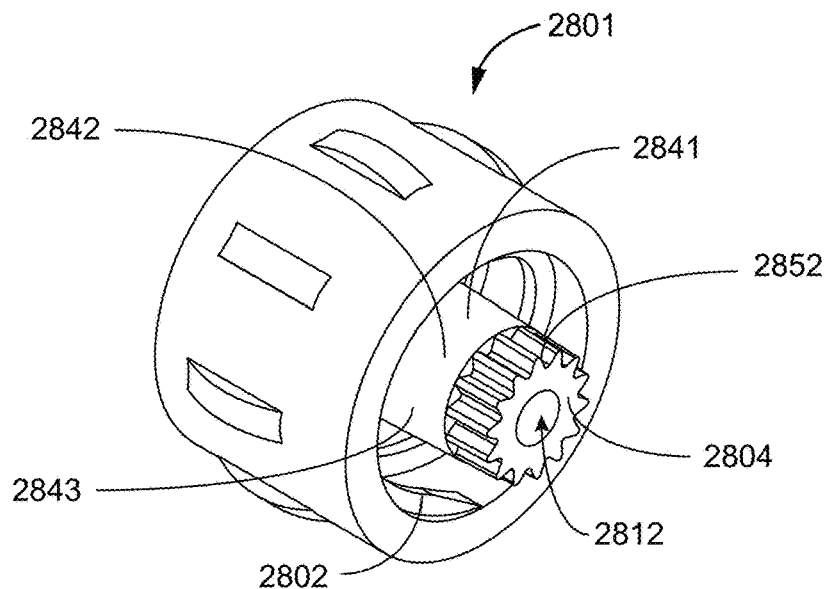
Figure 28B:
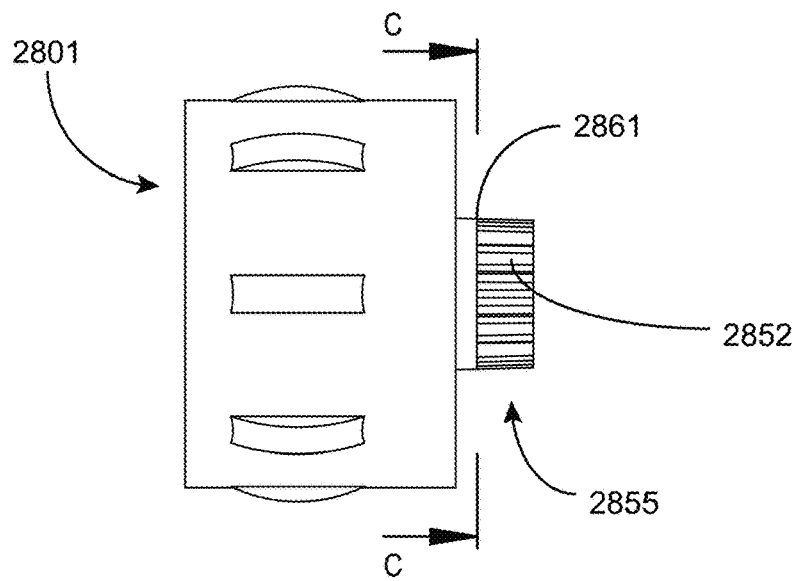
Figure 28C:
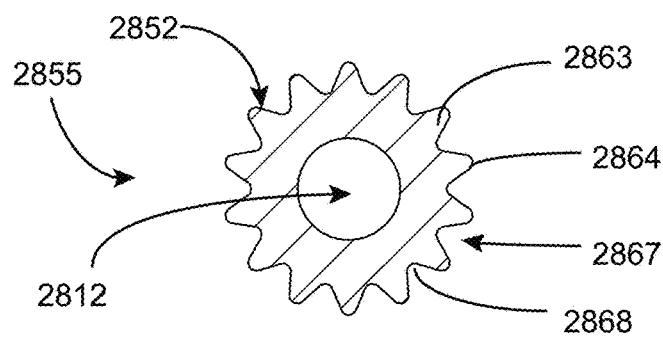
Figure 28D:
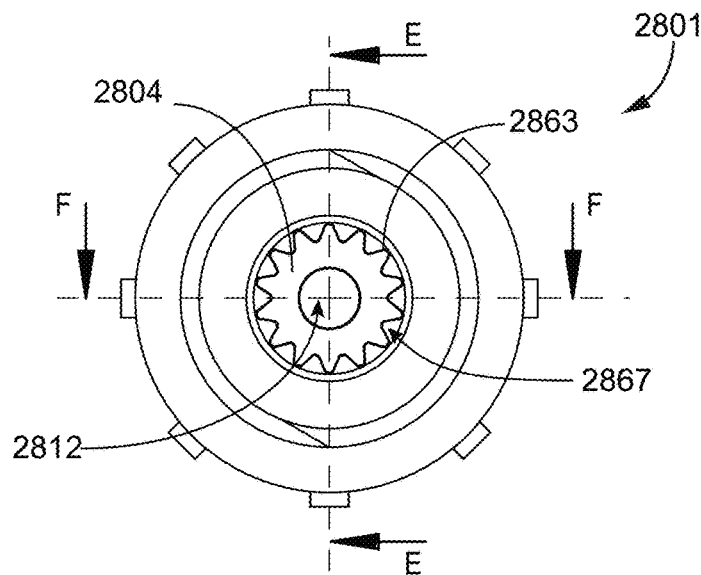
Figure 28E:
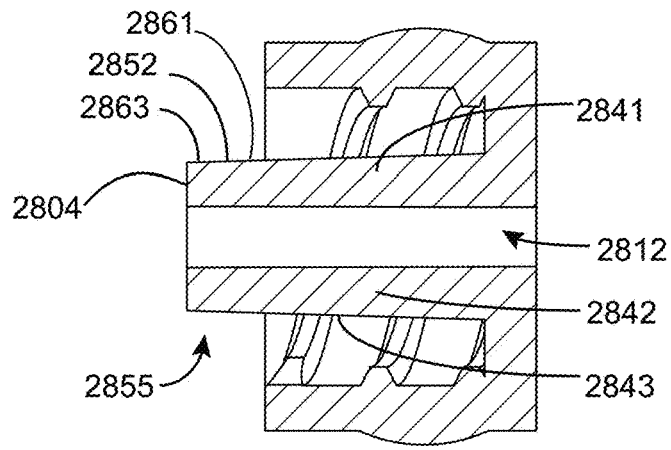

FIG. 28E is a cross-sectional view of the male luer connector of FIG. 28A along line E-E of FIG. 28D.

Figure 28F:
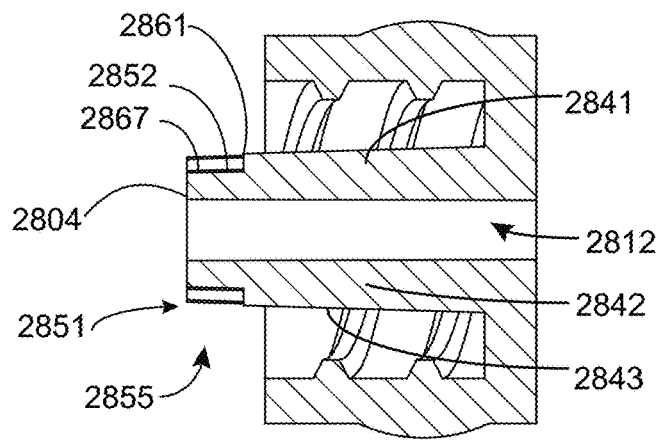

FIG. 28F is a cross-sectional view of the male luer connector of FIG. 28A along line F-F of FIG. 28D.

FIG. 29A is an isometric view of a male luer connector according to some examples.

FIG. 29B is a side view of the male luer connector of FIG. 29A.

FIG. 29C is a cross-sectional view of the male luer connector of FIG. 29A along line C-C of FIG. 29B.

FIG. 29D is a cross-sectional view of the male luer connector of FIG. 29A along line D-D of FIG. 29B.

Figure 29E:
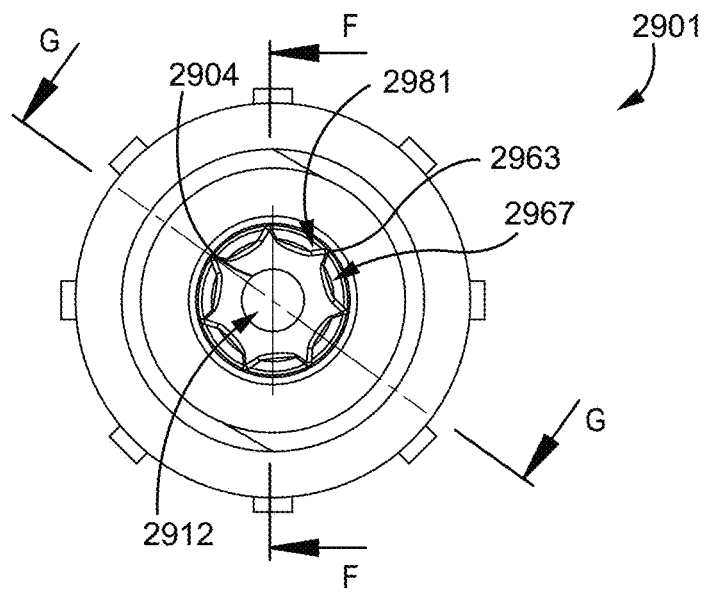

FIG. 29E is an end view of the male luer connector of FIG. 29A.

Figure 29F:
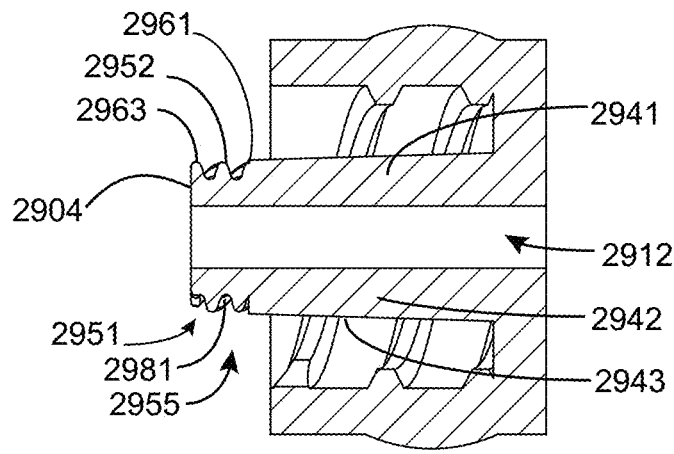

FIG. 29F is a cross-sectional view of the male luer connector of FIG. 29A along line F-F of FIG. 29E.

Figure 29G:
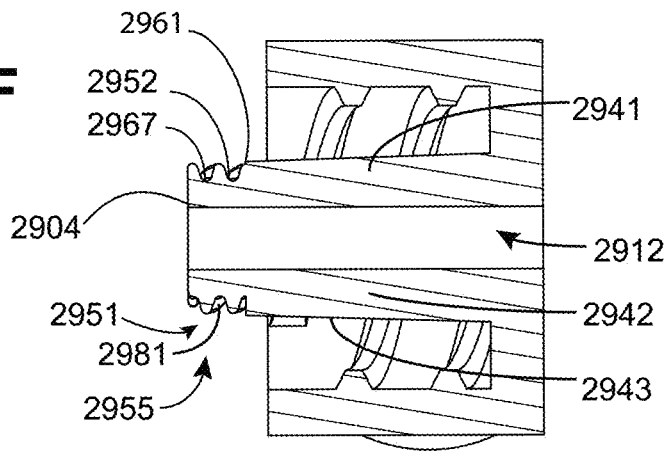

FIG. 29G is a cross-sectional view of the male luer connector of FIG. 29A along line G-G of FIG. 29E.

FIG. 30A is an isometric view of a male luer connector according to some examples.

FIG. 30B is a side view of the male luer connector of FIG. 30A.

FIG. 30C is a cross-sectional view of the male luer connector of FIG. 30A along line C-C of FIG. 30B.

FIG. 30D is a cross-sectional view of the male luer connector of FIG. 30A along line D-D of FIG. 30B.

Figure 30E:
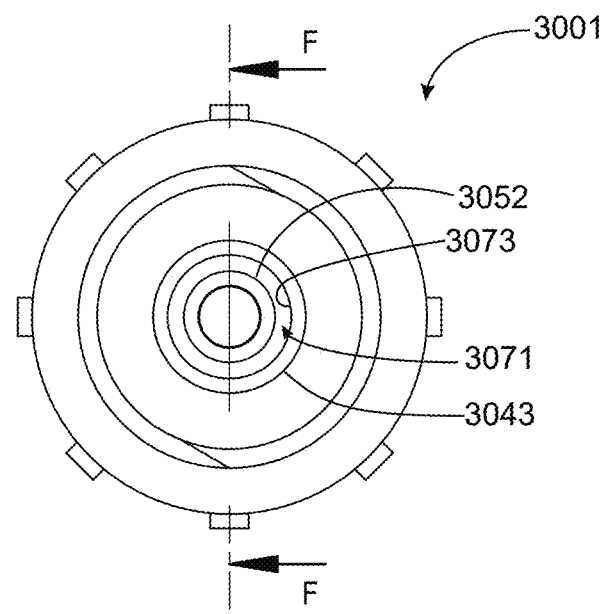

FIG. 30E is an end view of the male luer connector of FIG. 30A.

Figure 30F:
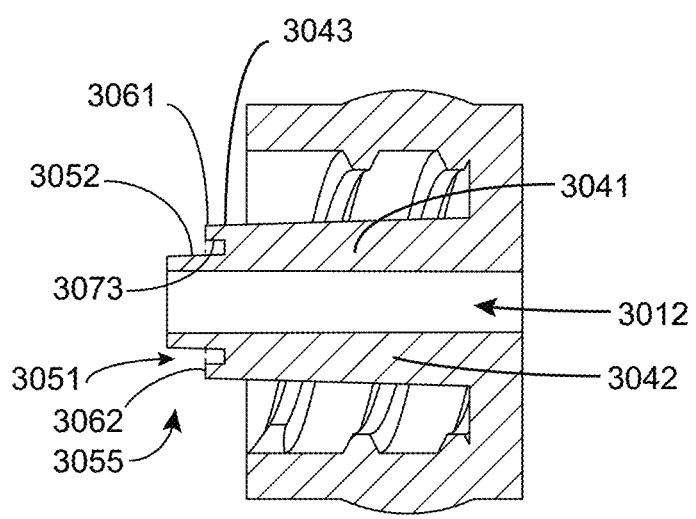

FIG. 30F is a cross-sectional view of the male luer connector of FIG. 30A along line F-F of FIG. 30E.

Figure 31A:
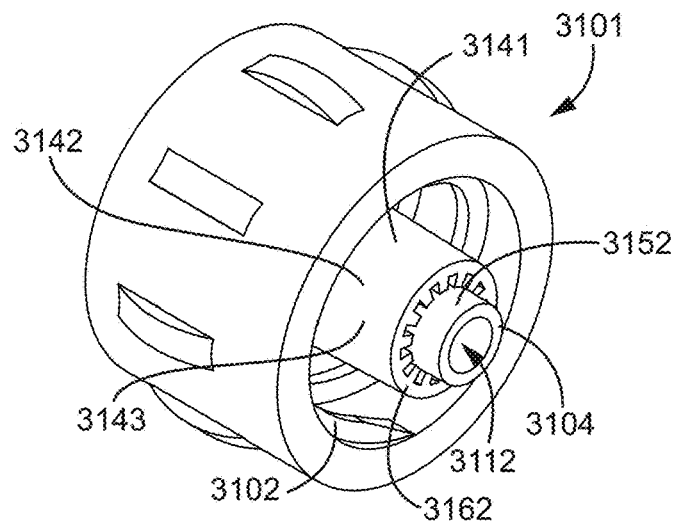

FIG. 31A is an isometric view of a male luer connector according to some examples.

Figure 31B:
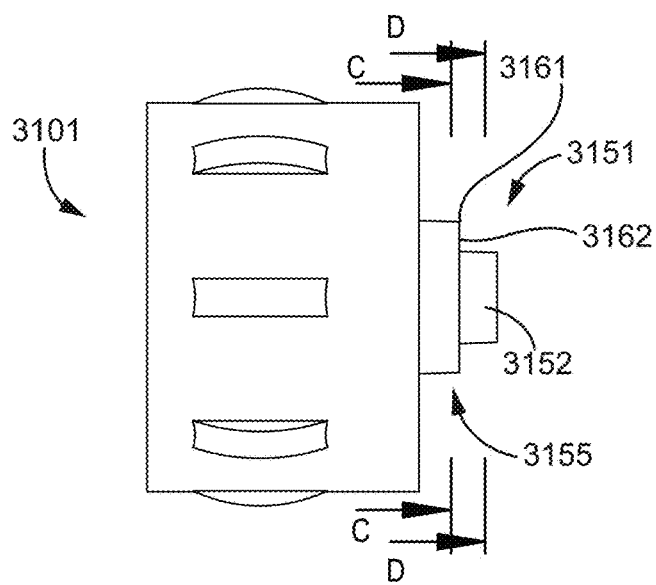

FIG. 31B is a side view of the male luer connector of FIG. 31A.

Figures 31C, 31D:
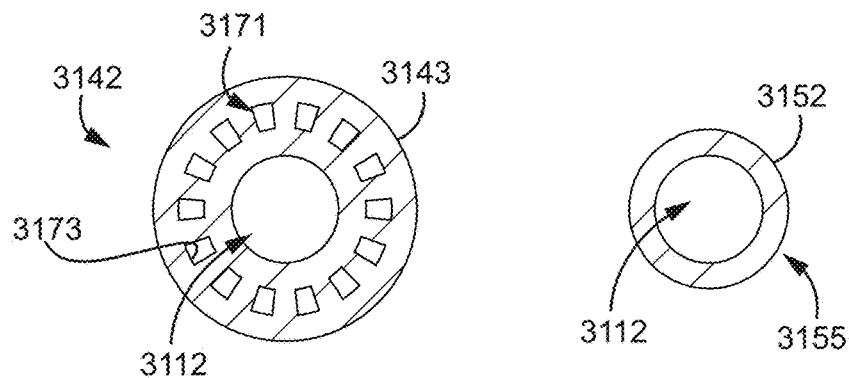

FIG. 31C is a cross-sectional view of the male luer connector of FIG. 31A along line C-C of FIG. 31B.

FIG. 31D is a cross-sectional view of the male luer connector of FIG. 31A along line D-D of FIG. 31B.

Figure 31E:
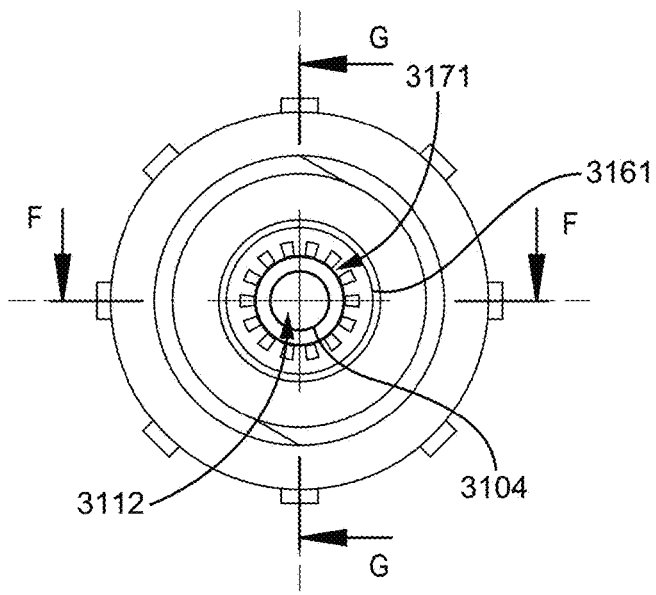

FIG. 31E is an end view of the male luer connector of FIG. 31A.

Figure 31F:
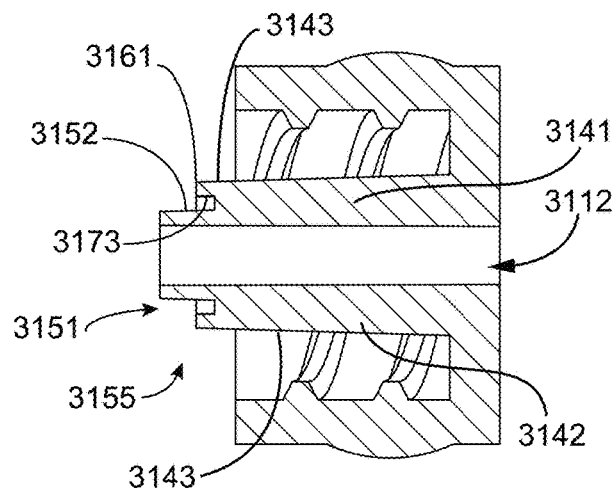

FIG. 31F is a cross-sectional view of the male luer connector of FIG. 31A along line F-F of FIG. 31E.

Figure 31G:
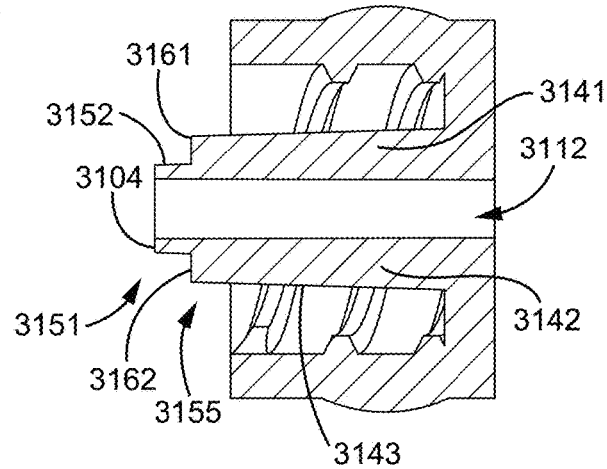

FIG. 31G is a cross-sectional view of the male luer connector of FIG. 31A along line G-G of FIG. 31E.

FIG. 32A is an isometric view of a male luer connector according to some examples.

FIG. 32B is a side view of the male luer connector of FIG. 32A.

FIG. 32C is a cross-sectional view of the male luer connector of FIG. 32A along line C-C of FIG. 32B.

FIG. 32D is a cross-sectional view of the male luer connector of FIG. 32A along line D-D of FIG. 32B.

Figure 32E:
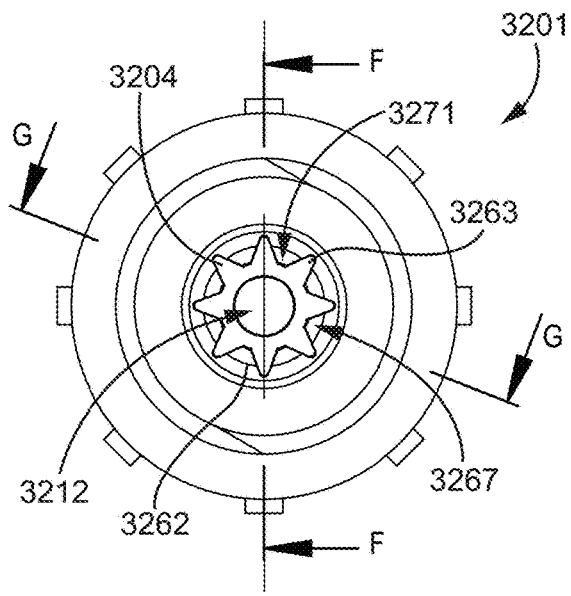

FIG. 32E is an end view of the male luer connector of FIG. 32A.

Figure 32F:
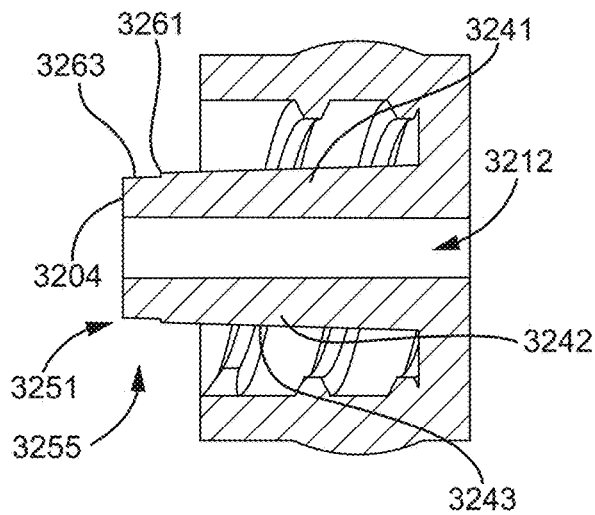

FIG. 32F is a cross-sectional view of the male luer connector of FIG. 32A along line F-F of FIG. 32E.

Figure 32G:
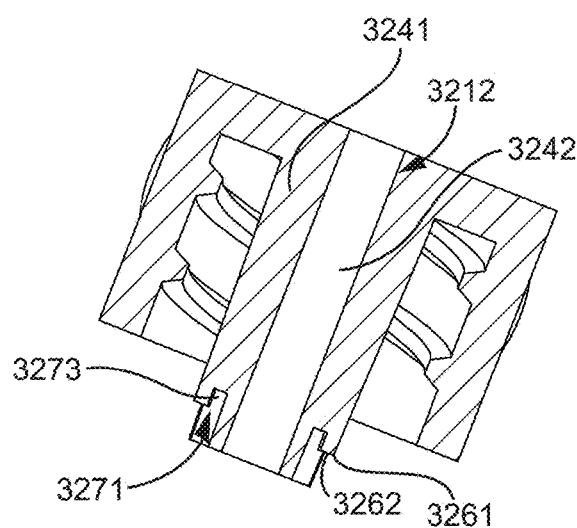

FIG. 32G is a cross-sectional view of the male luer connector of FIG. 32A along line G-G of FIG. 32E.

Figure 33A:
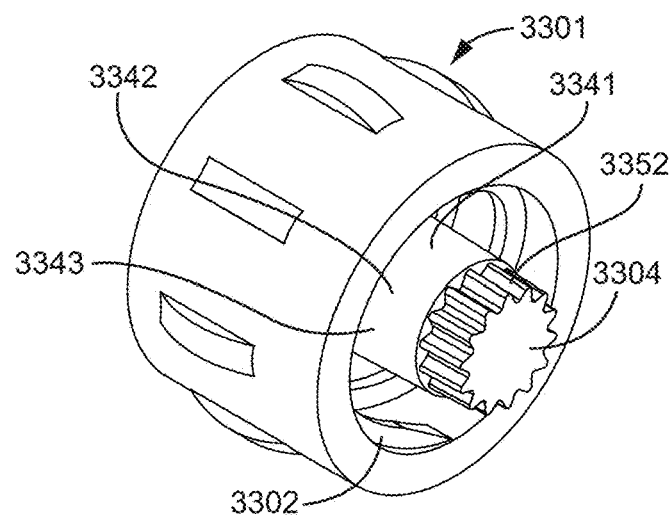

FIG. 33A is an isometric view of a male luer cap according to some examples.

Figure 33B:
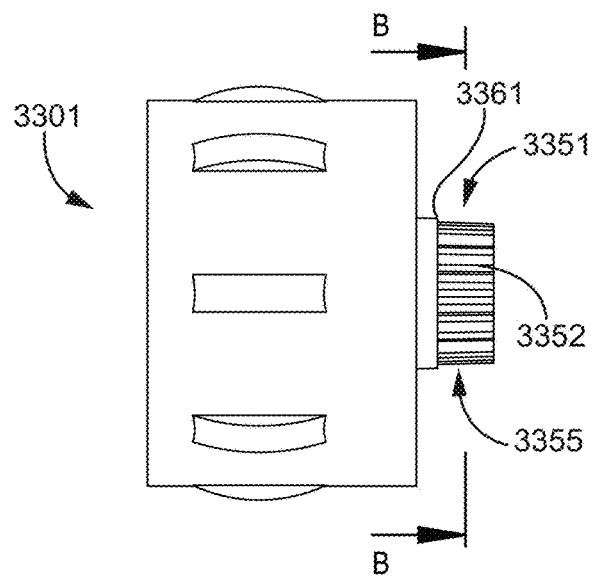

FIG. 33B is a side view of the male luer cap of FIG. 33A.

Figure 33C:
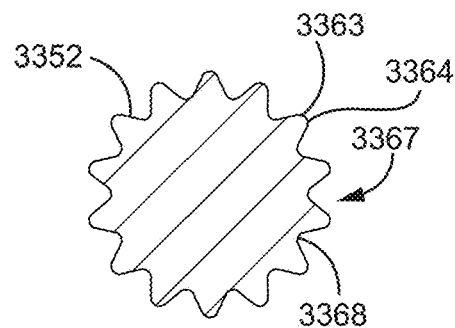

FIG. 33C is a cross-sectional view of the male luer cap of FIG. 33A along line C-C of FIG. 33B.

Figure 33D:
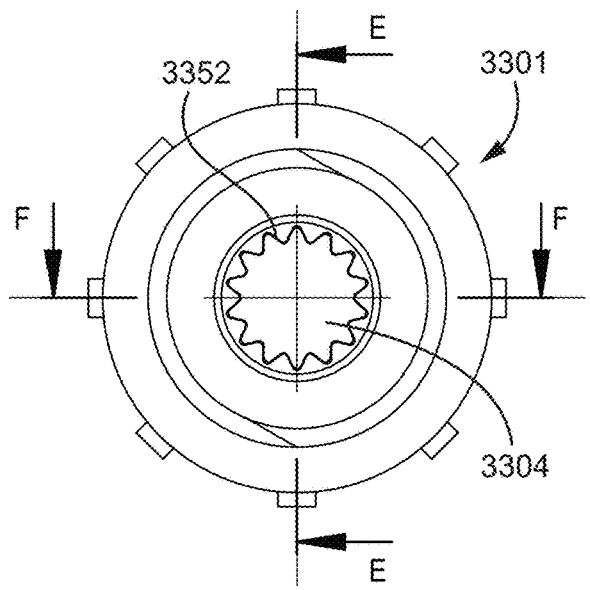

FIG. 33D is an end view of the male luer cap of FIG. 33A.

Figure 33E:
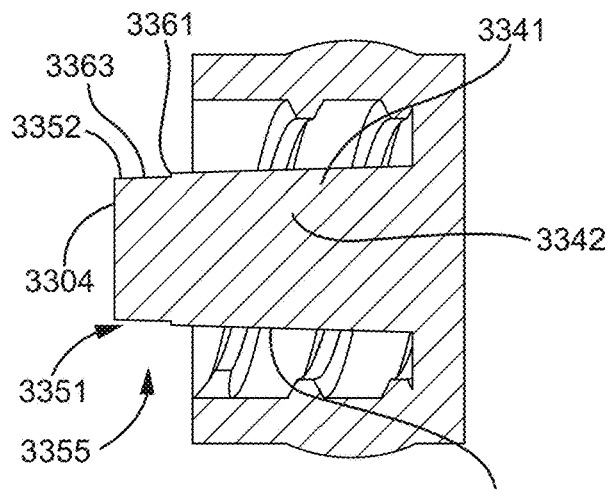

FIG. 33E is a cross-sectional view of the male luer cap of FIG. 33A along line E-E of FIG. 33D.

Figure 33F:
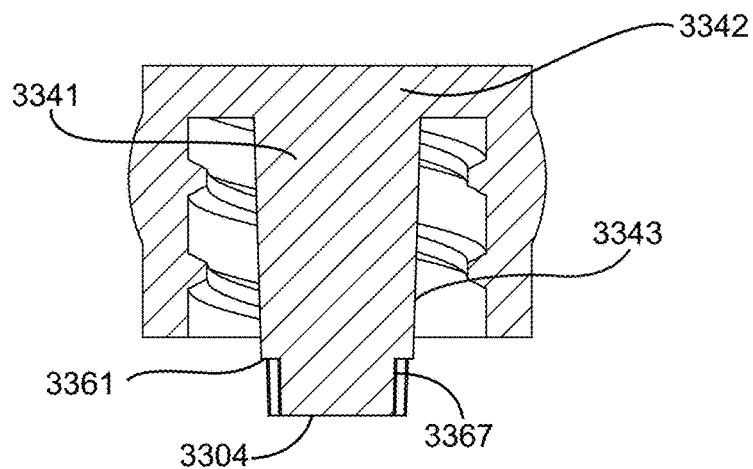

FIG. 33F is a cross-sectional view of the male luer cap of FIG. 33A along line F-F of FIG. 33D.

Figure 34A:
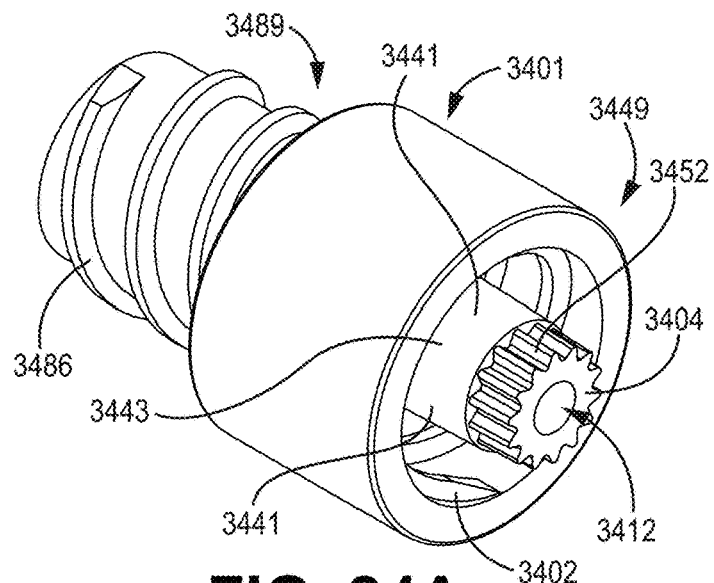

FIG. 34A is an isometric view of a luer coupler according to some examples.

Figure 34B:
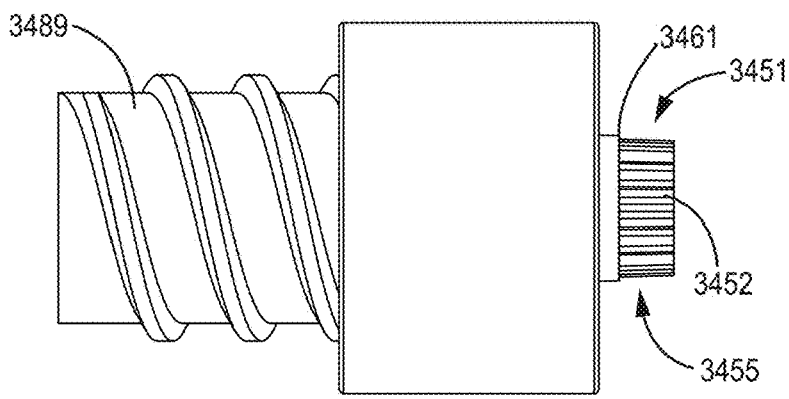

FIG. 34B is a side view of the luer coupler of FIG. 34A.

Figure 34C:
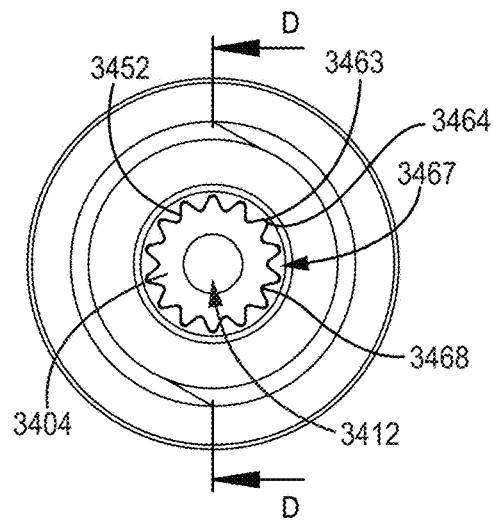

FIG. 34C is an end view of the luer coupler of FIG. 34A.

Figure 34D:
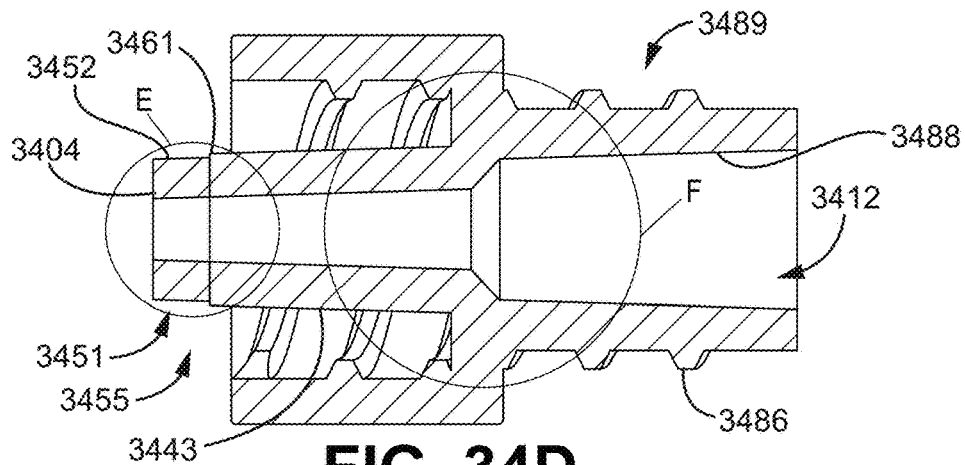

FIG. 34D is a cross-sectional view of the luer coupler of FIG. 34A along line D-D of FIG. 34C.

Figure 34E:
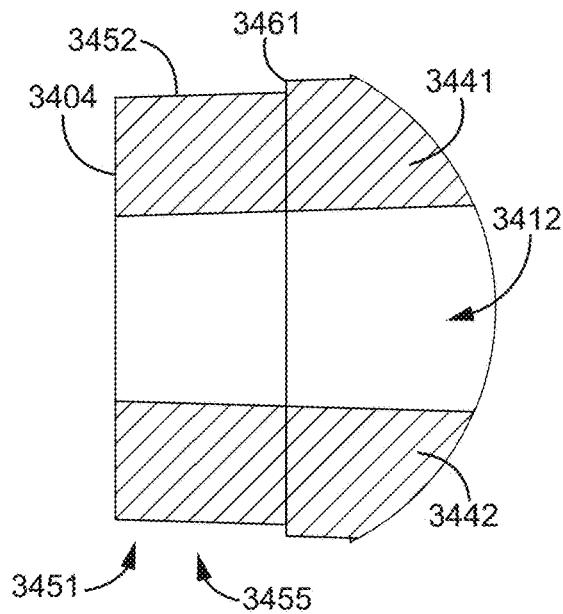

FIG. 34E is an enlarged view of FIG. 34D inside circle E.

Figure 34F:
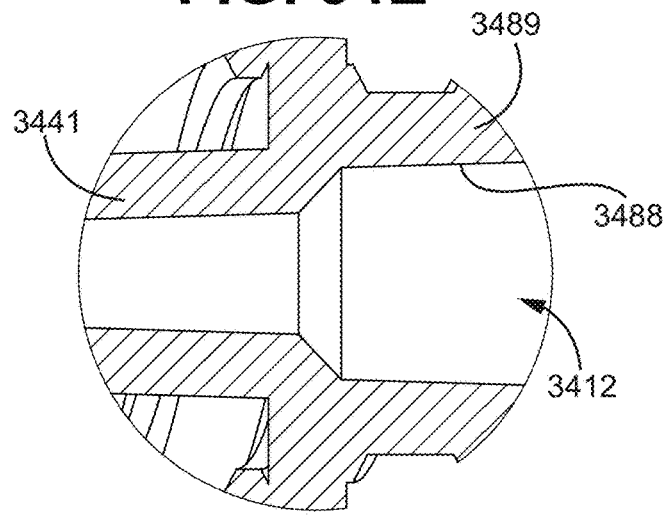

FIG. 34F is an enlarged view of FIG. 34D inside circle F.

Figure 35A:
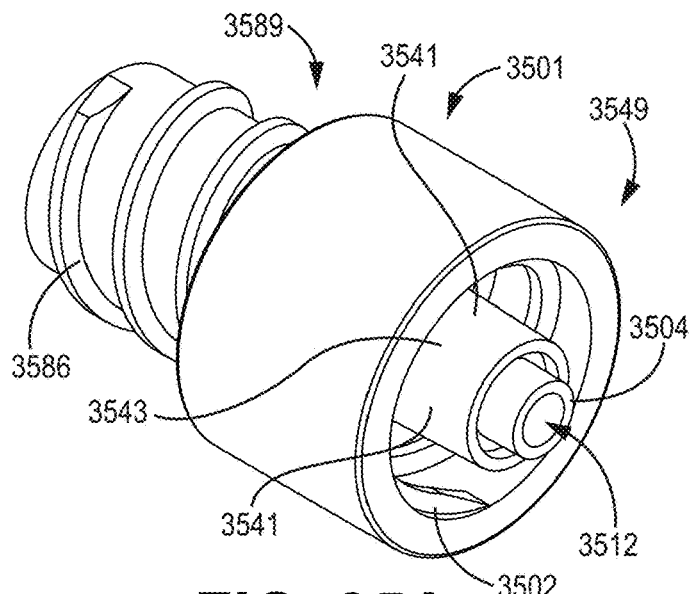

FIG. 35A is an isometric view of a luer coupler according to some examples.

Figure 35B:
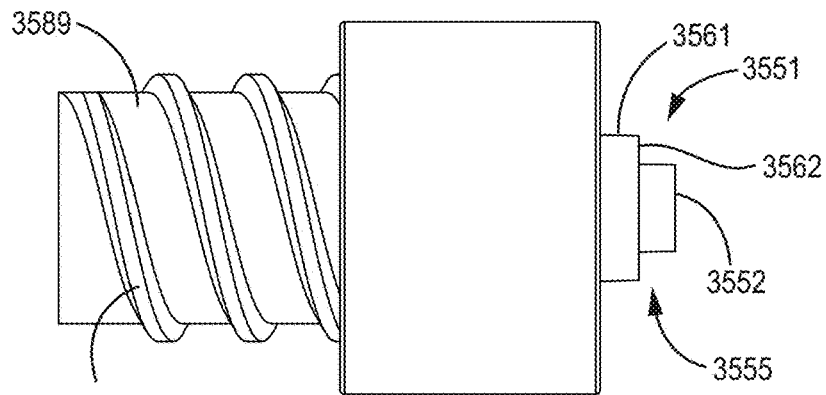

FIG. 35B is a side view of the luer coupler of FIG. 35A.

Figure 35C:
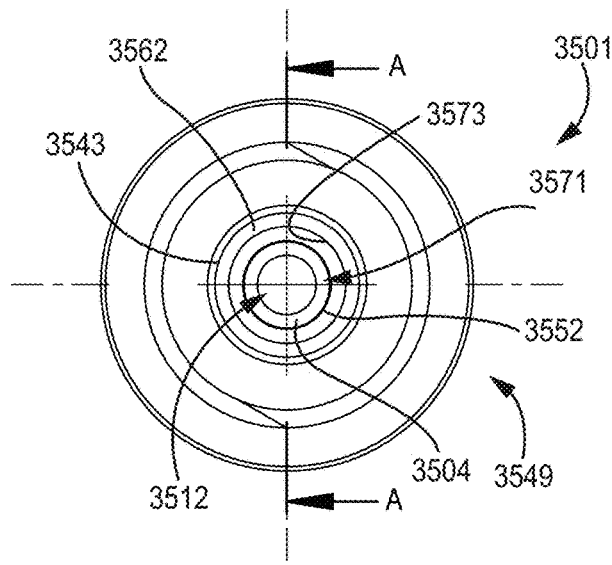

FIG. 35C is an end view of the luer coupler of FIG. 35A.

Figure 35D:
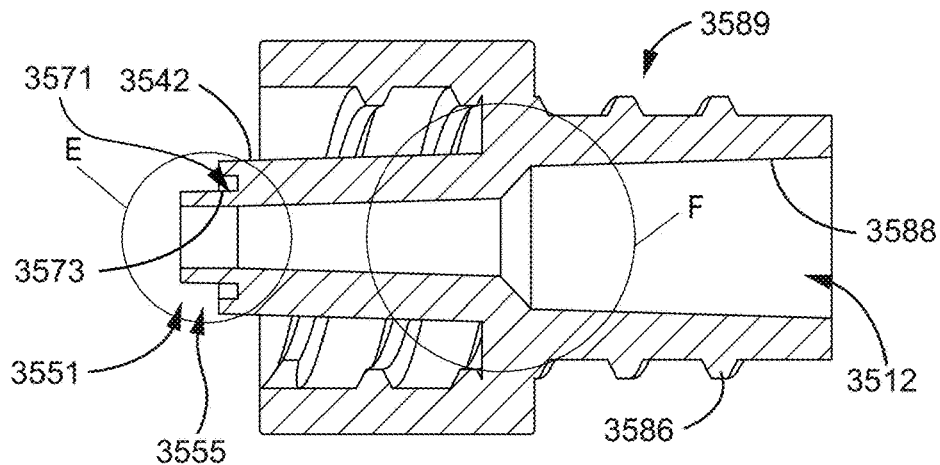

FIG. 35D is a cross-sectional view of the luer coupler of FIG. 35A along line D-D of FIG. 35C.

Figure 35E:
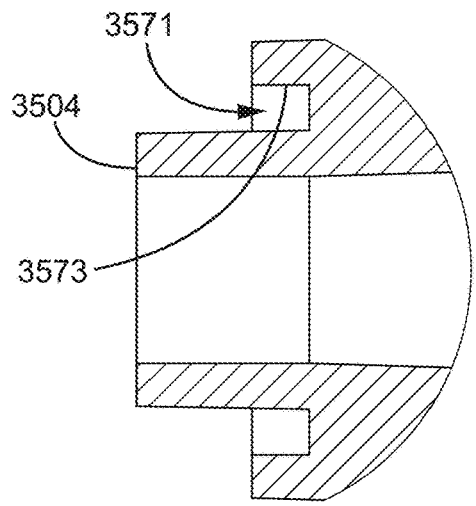

FIG. 35E is an enlarged view of FIG. 35D inside circle E.

Figure 35F:
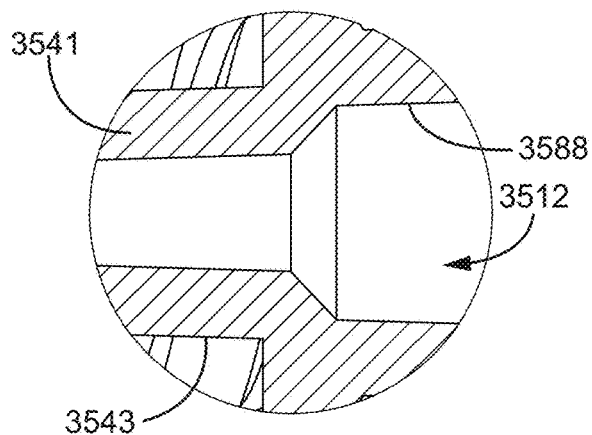

FIG. 35F is an enlarged view of FIG. 35D inside circle F.

Figure 36:
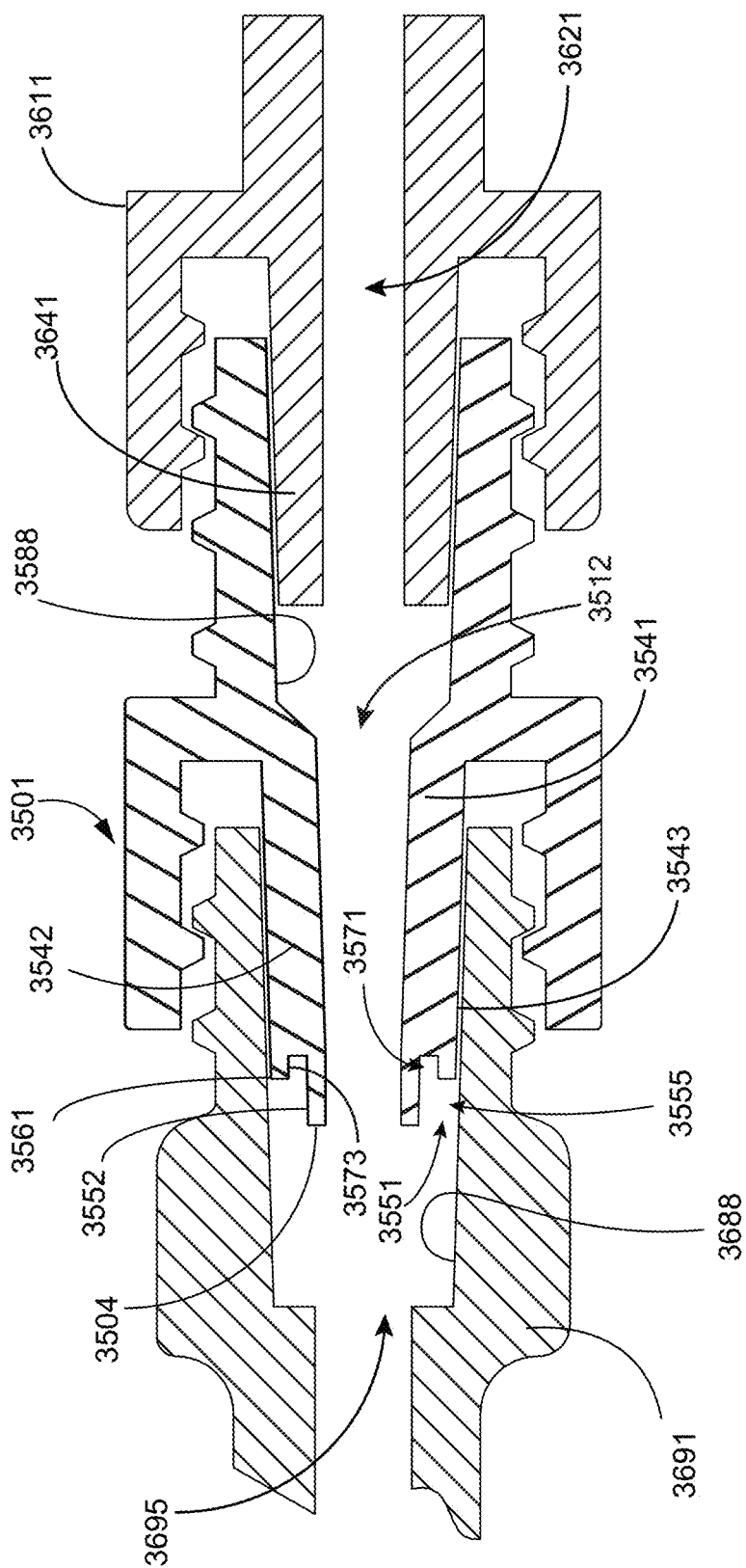

FIG. 36 is a cross-sectional view of the luer coupler of FIG. 34A installed between a female luer connector and a male luer connector according to some examples.

Figure 37:
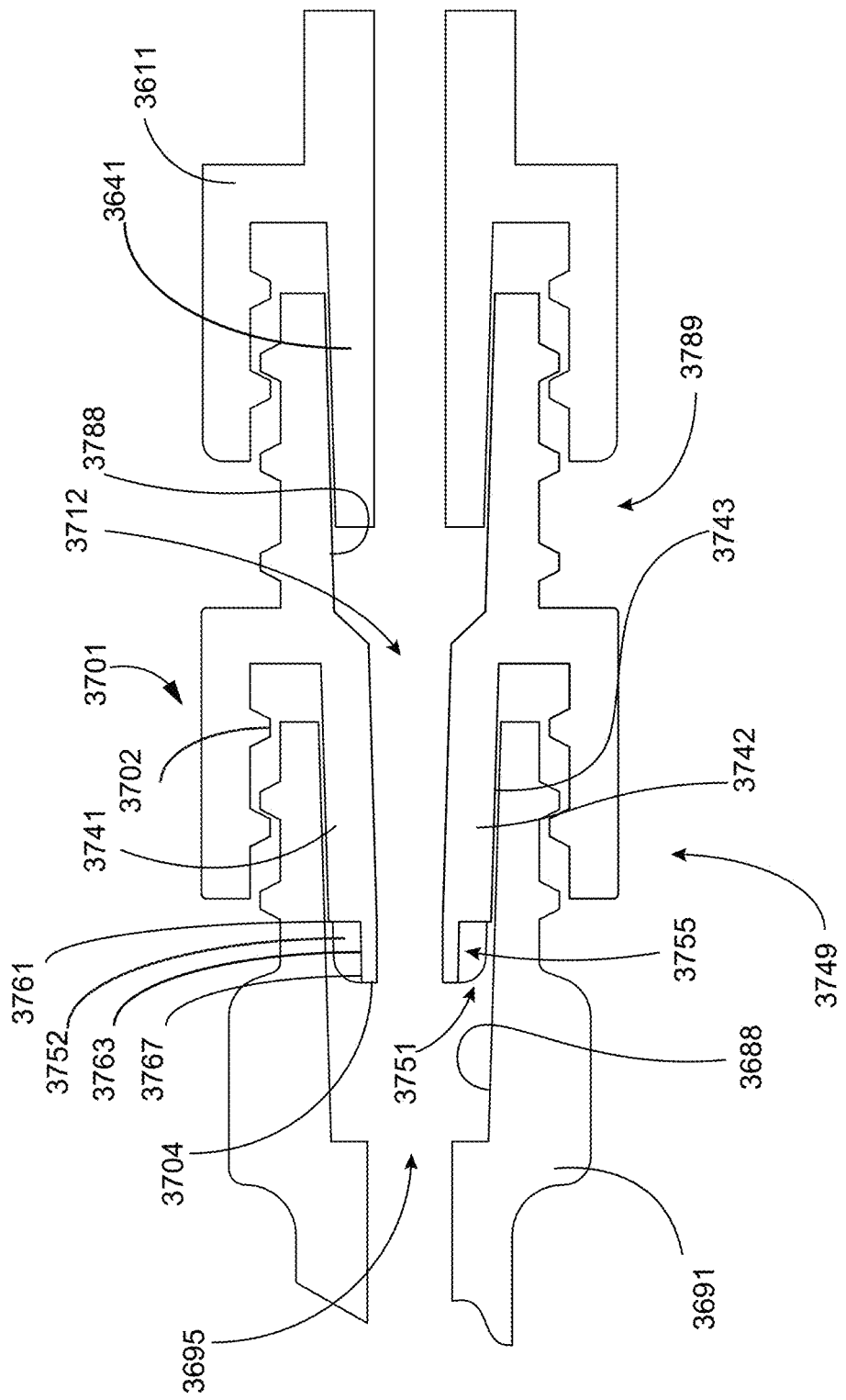

FIG. 37 is a cross-sectional view of the luer coupler of FIG. 35A installed between a female luer connector and a male luer connector according to some examples.

Figure 38:
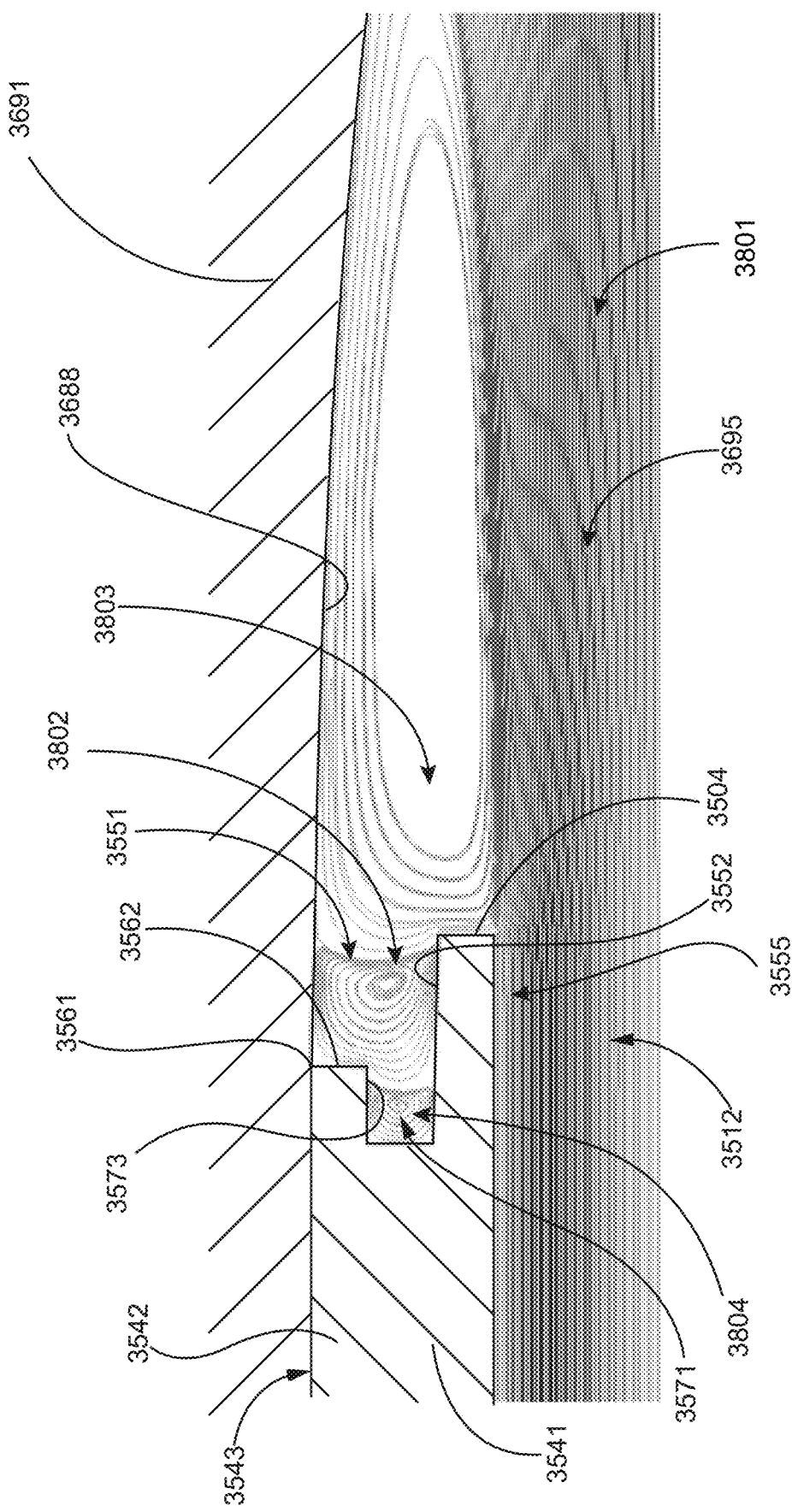

FIG. 38 is a fluid flow model showing recirculating flow within a male-female luer connection under syringe load conditions.

Figure 39:
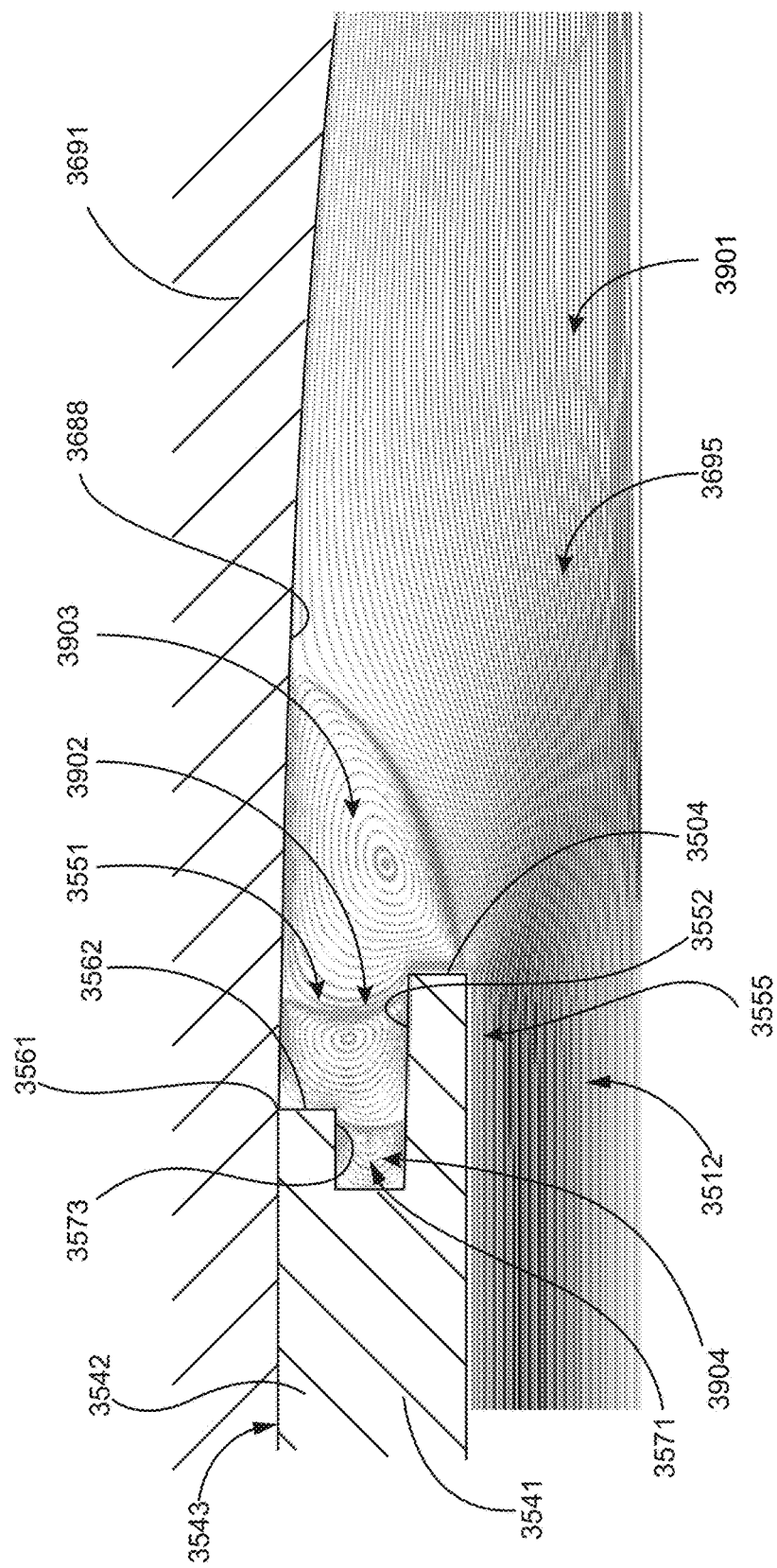

FIG. 39 is a fluid flow model showing recirculating flow within a male-female luer connection under IV drip conditions.

It will be noted that in some cross-sectional figures the illustrations have been simplified, such as removal of the background threads on the sealing cover to make the various aspects of the invention more apparent. While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein. For example, the term "infusion device" of FIG. 9 was chosen to point out that the examples are not limited to a specific infusion device. The infusion device can be a needleless connector, a bloodline, an infusion set or other infusion devices having a male connector.

DETAILED DESCRIPTION

Numerous challenges are present for safely using medical devices incorporating male and female luer connectors. For example, medical devices such as catheters used in hemodialysis, peritoneal dialysis, parenteral nutrition and chemotherapy are often worn for prolonged periods of time in the moist environment next to a patient's skin. This is an ideal environment for bacterial growth. Peripherally inserted central catheters and midline catheters will typically have dozens of connections made between a male and female luer over the course of use, and each time the device is connected it provides an opportunity for infection caused by ingress of organisms along the female luer. And every infusion device that has a female luer hub is susceptible to the fact that the interior female luer surface is not readily accessible to sanitizing wipes. Conventional sterilization methods are not able to kill microorganisms once they ingress to the female luer surface. Thus, these organisms are free to continue to ingress until reaching the bloodstream and ultimately creating a bloodstream infection. In addition, drug resistant organisms are becoming more common in hospitals and outpatient healthcare settings, which makes treatment of bloodstream infections more difficult.

Multiple ingress pathways can lead to contamination of the female luer surface. One source of female luer contamination occurs when the female luer is open, with no male luer inserted. During the time the female luer is open, it is susceptible to airborne organisms landing on the surface (such as from a person's breath or other source). Another source of female luer contamination is ingress along the threads and proximal end of the female hub, where organisms can then enter into the very small gap that exists between the proximal end of the male-female luer surfaces where the surfaces touch.

Those skilled in the art understand that organisms can ingress to the proximal end of the hub, but they are widely unaware that a gap exists between the male and female luers and that organisms can infiltrate this gap where standard cleaning procedures are ineffective. Thus, the common viewpoint is that cleaning the end of a female luer connector is sufficient to stop this route of organism ingress. The inventors have discovered that this is not sufficient; standard alcohol wiping/cleaning procedures are not effective at killing the organisms that enter the inside of the female luer. Once inside the female luer, organisms can be pushed by the tip of the male luer into the lumen of the female luer device.

For example, use of needleless connectors on infusion devices is common practice. The NCs are typically replaced every 4-7 days, thus they are prone to contamination of the inside of the female luer, as described above, which can ultimately lead to bloodstream infection.

The technology disclosed herein provides a distal recess at the tip of the male luer member. Organisms inside the female luer remain proximal to the lumen of the male luer. The distal recess region contains a concentrated amount of an antimicrobial composition that remains confined within the distal recess. Various examples provided herein create an environment that confines the antimicrobial agent near the distal end of the male luer.

Figure 1:
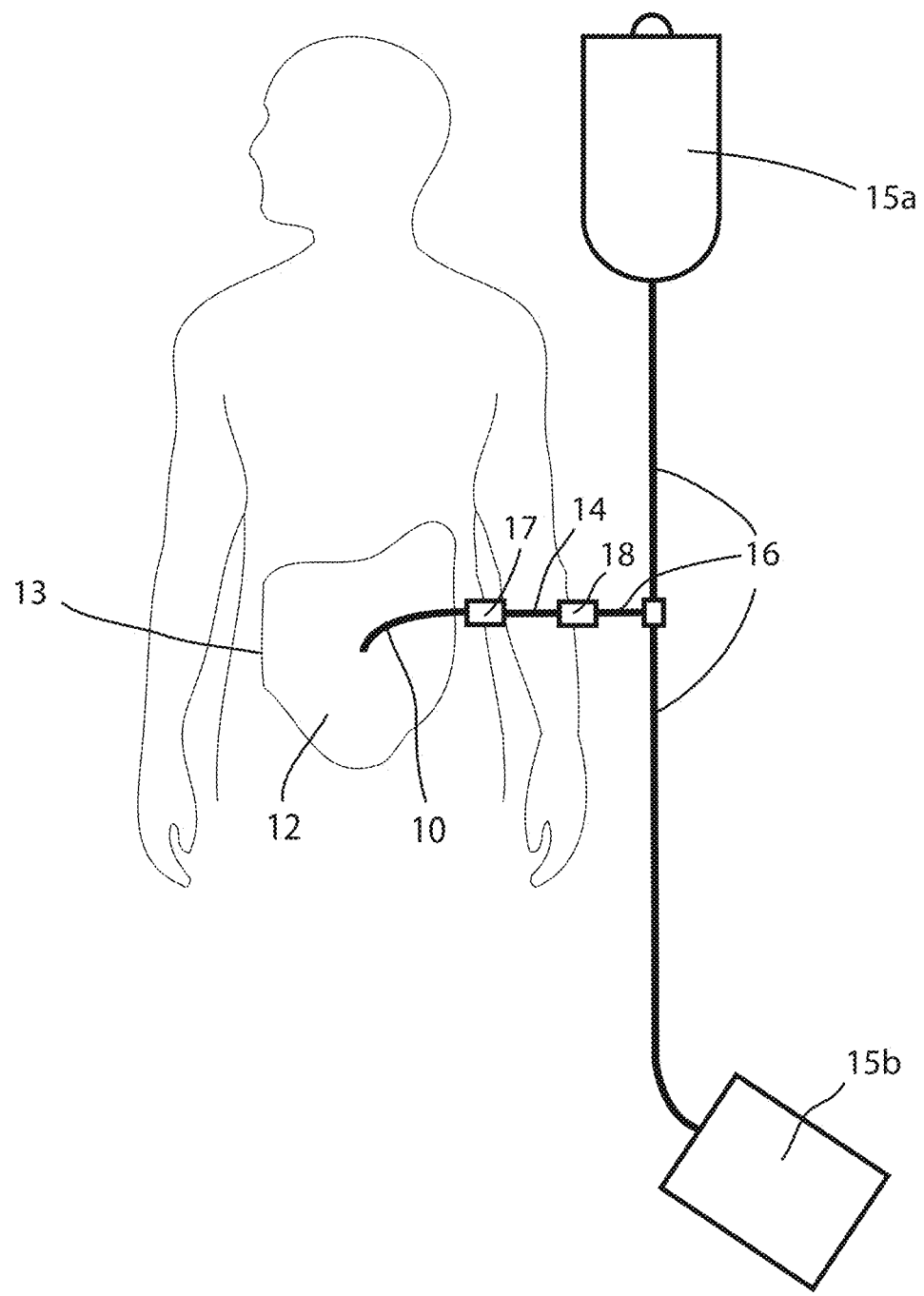
FIG. 1 is a schematic diagram of a patient undergoing peritoneal dialysis, showing a peritoneal catheter extending into a peritoneal cavity into which a dialysis solution is injected and then removed.

Referring now to the drawings, FIG. 1 is a schematic diagram of a patient undergoing peritoneal dialysis, showing a peritoneal catheter 10 extending into a peritoneal cavity 12 (surrounded by peritoneum 13) of the patient into which a dialysis solution from source bag 15a flows into the patient. The dialysis solution is then later drained into drain bag 15b. The catheter 10 is in fluid communication with the bags 15a and 15b by means of a tubular transfer set 14 and an infusion set 16. Couplings 17 and 18 are positioned on either end of the transfer set 14. Coupling 17 joins the transfer set 14 to the catheter 10, while coupling 18 joins the transfer set 14 to the infusion set 16. Generally, the catheter 10 and transfer set 14 are kept joined at coupling 17 for long periods of time (weeks and months), while the transfer set 14 and infusion set 16 are only joined at coupling 18 for the dialysis solution (dialysate) exchange process. This dialysis solution exchange process can take, for example, 30 minutes up to four times a day for continuous ambulatory peritoneal dialysis (CAPD), or overnight once a day for automated peritoneal dialysis (APD).

During the CAPD exchange process the waste dialysis solution flows from the peritoneal cavity 12 through the catheter 10, on to the coupling 17 and transfer set 14, then through coupling 18 and finally through the lower portion of the infusion set 16 into the drain bag 15b. After the exchange process is complete, the infusion set 16 is separated at coupling 18 from transfer set 14 and the female connector of transfer set 14 is capped until the next dialysis solution exchange is initiated (not shown). Thus, in typical peritoneal dialysis the exchange process is initiated by removing a male cap from the female connector of transfer set 14 and then joining to the infusion set 16 to form coupling 18; and this process is reversed at the end of the exchange process by removing the infusion set 16 at coupling 18 and installing a new male cap.

It will be appreciated that FIG. 1 has been simplified for clarity. An automated machine or different tubing arrangement may be used to transfer dialysis solution from the source bag 15a to the peritoneal cavity 12 or from the peritoneal cavity 12 to the drain bag 15b. The movement of the dialysis solution can be advanced by gravity, pumps, or other mechanisms.

Figure 2A:
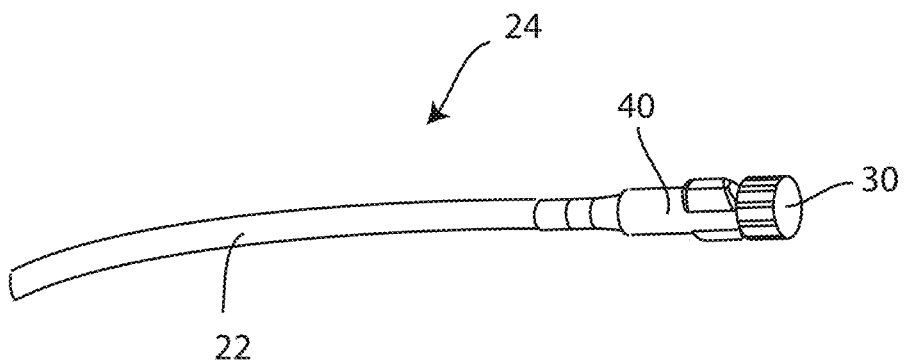
FIG. 2A is a perspective view of a proximal end of a peritoneal catheter with a male cap installed on a female connector.
Figure 2B:
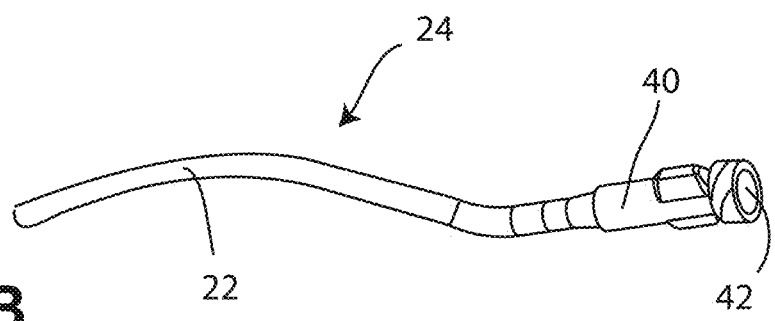
FIG. 2B is a perspective view of the proximal end of the peritoneal catheter of FIG. 2A showing the female connector after the male cap has been removed.
Figure 2C:
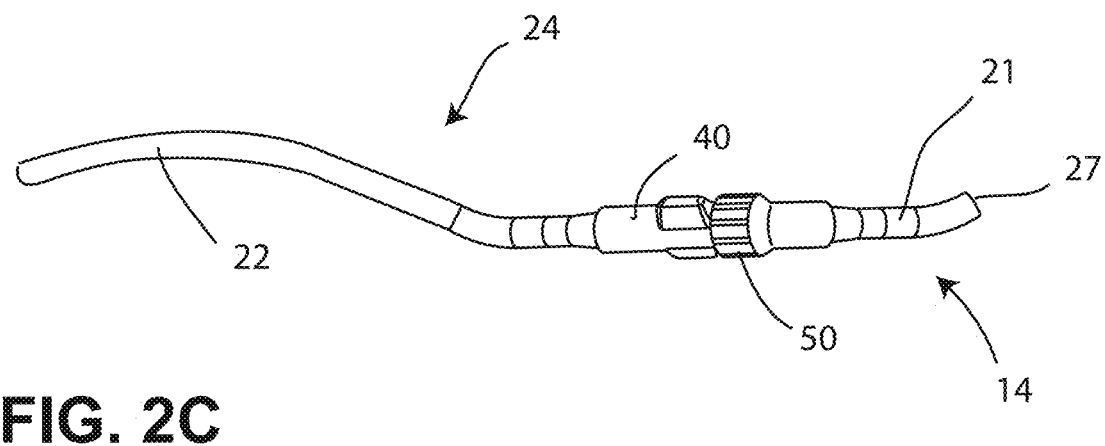
FIG. 2C is a perspective view of the proximal end of the peritoneal catheter of FIG. 2B connected to a transfer set at a coupling formed by the female connector and a male connector.

Referring now to FIG. 2A, a perspective view of the proximal end of a peritoneal catheter 24 with a male cap 30 installed on a female connector 40 is shown, while FIG. 2B is a perspective view of the proximal end of the peritoneal catheter 24 of FIG. 2A with the male cap removed, and FIG. 2C is a perspective view of the proximal end of the peritoneal catheter 24 of FIG. 2B connected to a transfer set 14. FIG. 2A specifically shows a perspective view of the proximal end of peritoneal catheter 24 having a tube 22 with a female connector 40 onto which a male cap 30 has been installed. Generally, the female connector 40 includes a female luer inside (not shown), while the male cap 30 includes a male luer (not shown). The proximal end of the peritoneal catheter 24 (that portion furthest from the patient) is shown along with female connector 40 and male cap 30. Also, the transfer set 14 of FIG. 2C is shown in a foreshortened construction for ease in illustration. Normally the transfer set 14 is from approximately 6 to 18 inches long but can be longer or shorter, and thus end 27 of tube 21 on transfer set 14 often includes an extended length before joining to a second connector (not shown) that is typically capped between dialysis treatments, but which is then uncapped and joined to an infusion set during dialysis.

FIG. 2B is a perspective view of the proximal end of the peritoneal catheter 24 of FIG. 2A with the male cap removed from the female connector 40, including a female luer 42. The female luer 42 is a volume within the interior area of the female connector 40 that receives and seals with a male luer from a male cap or male connector. FIG. 2C is a perspective view of the proximal end of the peritoneal catheter 24 of FIGS. 2A and 2B connected to a transfer set 14 by means of a male connector 50 comprising a male luer (the male luer is part of male connector 50 inside the end of the female connector 40 of peritoneal catheter 24, and not visible, but it will be understood that within the female connector 40 is a tapered male luer forming a seal with a female luer).

Figure 3C:
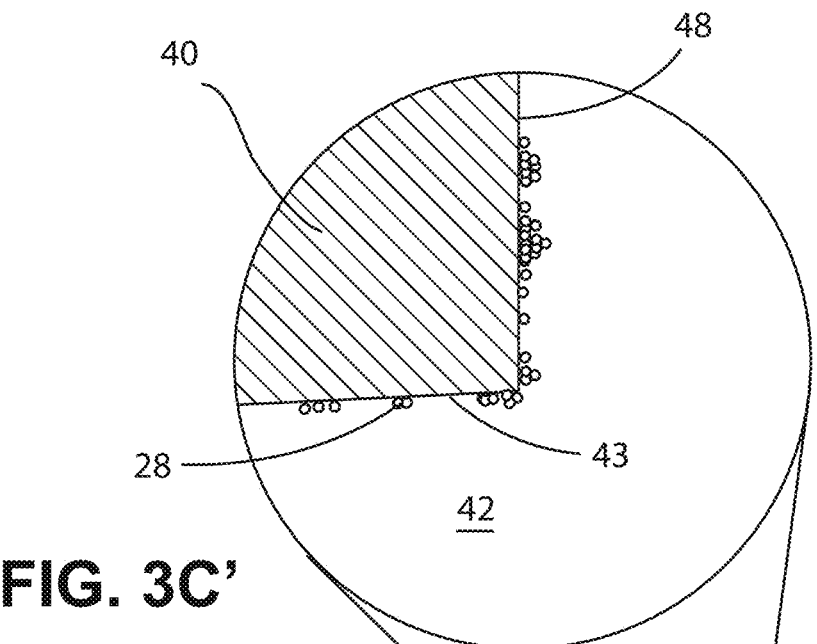
FIG. 3C is a cross-sectional sliced view of the proximal end of the peritoneal catheter, including the female connector, of FIG. 3B with the male cap having been removed.
Figure 3C:
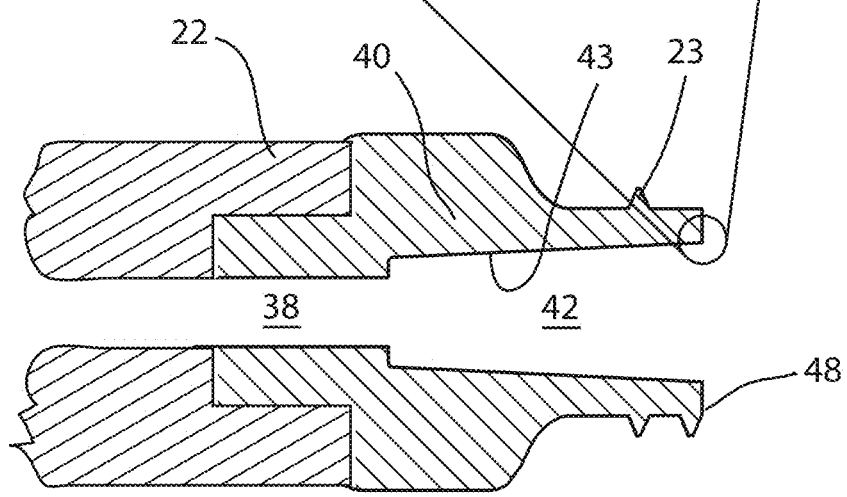

Now in references to FIGS. 3A to 3F', various stages of traditional cap and connector installation and removal are shown, along with properties of microbial growth on the cap and connector. FIG. 3A is a cross-sectional sliced view of a proximal end of a peritoneal catheter 24 with a male cap 30 installed. FIG. 3A provides an enlarged cross-sectional sliced view of the proximal end of the peritoneal catheter 24 with male cap 30 installed, corresponding for example to the construction of FIG. 2A, showing the female connector 40 with male cap 30. FIG. 3A shows directional arrows depicting the distal direction and the proximal direction (an intermediate location would be between the distal and proximal directions). FIG. 3A further shows a male cap 30, with the proximal and distal ends of the male cap 30 labeled. Thus "proximal" and "distal" are relative terms, showing the position relative to the patient and ends of a device.

As is shown in FIG. 3A, the male cap 30 includes a male luer 32 having a tapered outer surface 33, while the female connector 40 has a female luer 42 with a tapered inner surface 43 designed to seal with the tapered outer surface 33 of the male luer 32. The tip 34 of the male luer 32 (which is at the distal end of the male cap 30) is exposed to the interior of a lumen 38 (open channel) through the female connector 40. In FIG. 3A the male cap 30 is shown having threads 19, which engage with corresponding threads 23 of the female connector 40. The female connector 40 includes a female luer 42 which is a volume within the female connector 40. The female luer 42 in this embodiment includes a tapered inner surface 43. The female luer 42 of the female connector 40 and the male luer 32 of the male cap 30 form a fluid-tight connection at overlapping region 41. When the female connector 40 and male cap 30 are threaded together they still can provide an infiltration path into an interstitial space or gap 35 (and subsequently into the lumen 38) as shown in FIGS. 3A and 3A' where infiltration paths are shown, including past the threads 19, 23 to the interstitial space or gap 35 between the female connector 40 and male cap 30, more specifically (but not exclusively) between the tapered inner surface 43 of the female luer 42 of the female connector 40 and the tapered outer surface 33 of male luer 32 of the male cap 30. This interstitial space or gap 35 within the overlapping region 41 between the tapered surfaces 33, 43 of the male and female luers 32, 42 is present during installation and removal of the male cap 30 but our testing shows the gap 35 also often exists after the male cap 30 has been coupled to the female connector 40. When the male cap 30 is inserted into the female connector 40, the male and female luers 32, 42 generally form a fluid tight seal somewhere within the overlapping region 41 between them. However, the interstitial space or gap 35 commonly exists along at least a portion of the overlapping region 41, thus allowing microbes 28 to infiltrate into the gap 35 from the proximal end 48 of the female connector 40.

FIGS. 3B and 3B' show the cross-sectional sliced views of FIGS. 3A and 3A', but with microbes 28 having infiltrated past the threads 19 and 23 (the threads do not form a seal) and colonized portions of the interface between the female connector 40 and male cap 30 at gap 35. This infiltration and growth of microbes 28 is shown in schematic representation (the sizes of the microbes in reality is much smaller, and distribution can be irregular).

FIG. 3C is a cross-sectional sliced view of the proximal end of the peritoneal catheter 24 of FIGS. 3A and 3B with the male cap 30 removed, exposing the female luer 42, which is a void in the female connector 40 into which the male luer 32 of a male cap or male connector can be inserted (not shown), and FIG. 3C' is a closeup cross-sectional sliced view of a portion of the proximal end of the peritoneal catheter of FIG. 3C, specifically the proximal end 48 of the female connector 40. In FIGS. 3C and 3C' the microbes 28 are present on the proximal end 48 of the female connector 40, and even after removal of the male cap 30 many of the microbes 28 remain. Therefore, between dialysis treatments or other processes the female connector 40 often has high levels of microbes present, including on the exposed proximal end 48 and threads 23 as well as on the tapered inner surface 43 of the female luer 42 of the female connector 40. Thus, FIGS. 3C and 3C' are essentially a representation of the female connector 40 after removal of the male cap.

Figure 3D:
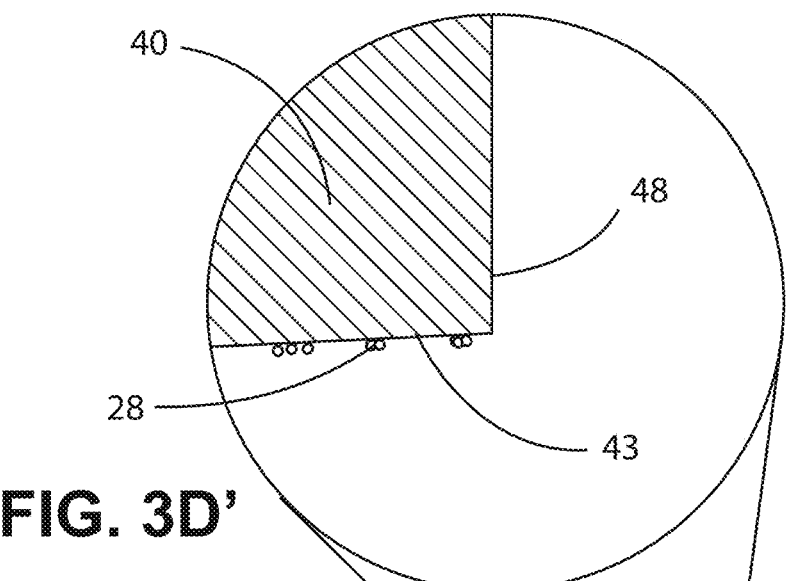
FIG. 3D is a cross-sectional sliced view of the proximal end of the peritoneal catheter, including the female connector, of FIG. 3C after cleaning.
Figure 3D:
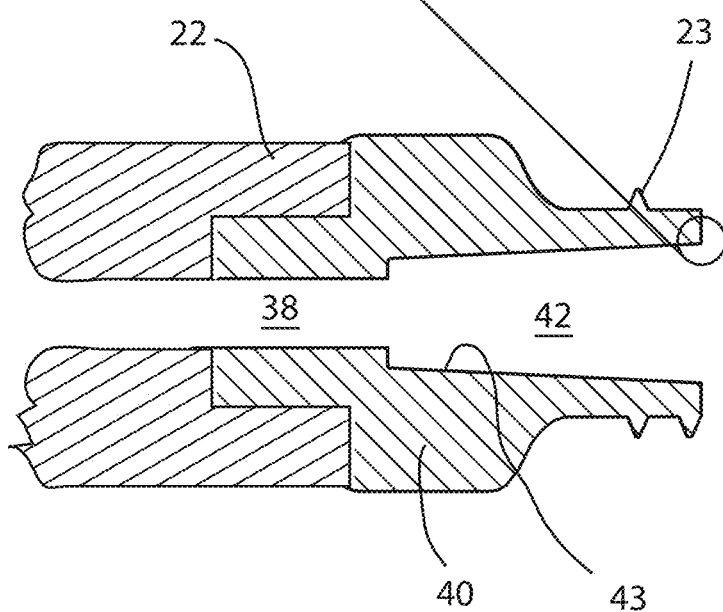

FIG. 3D is a cross-sectional sliced view of the proximal end of the peritoneal catheter of FIG. 3C with the male cap removed, and FIG. 3D' is a closeup cross-sectional sliced view of a portion of the proximal end of the peritoneal catheter of FIG. 3D. In FIGS. 3D and 3D' the female connector 40 has been cleaned, such as with an alcohol wipe, but microbes remain, in particular (in this embodiment) on the tapered inner surface 43 in the female luer 42 of the female connector 40 because the cleaning wipes do not reach sufficiently inside the female luer 42 of the female connector 40 when using industry standard cleaning procedures.

Figure 3E:
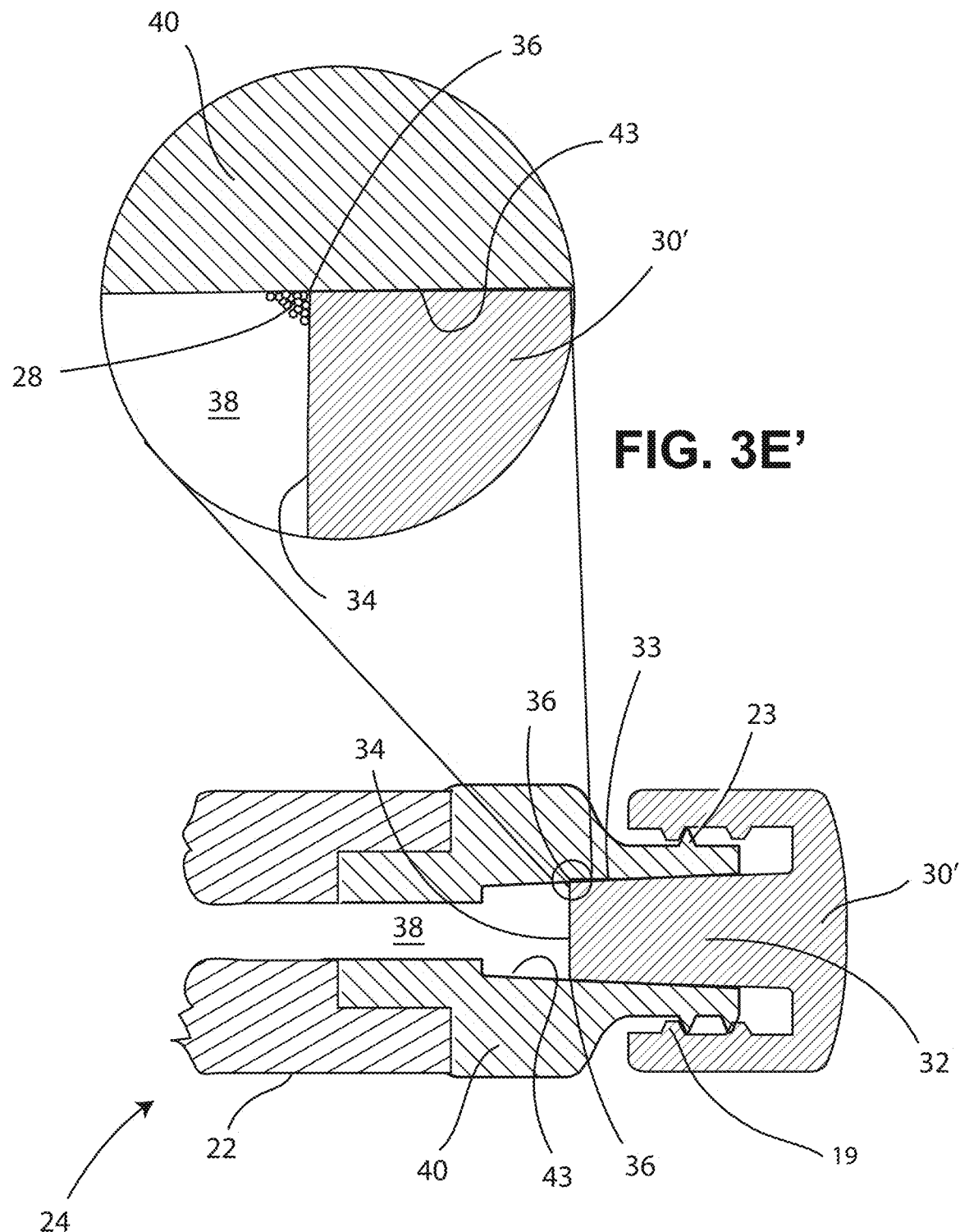
FIG. 3E is a cross-sectional sliced view of the proximal end of the peritoneal catheter of FIG. 3D with a new male cap coupled to the female connector.
Figure 3F:
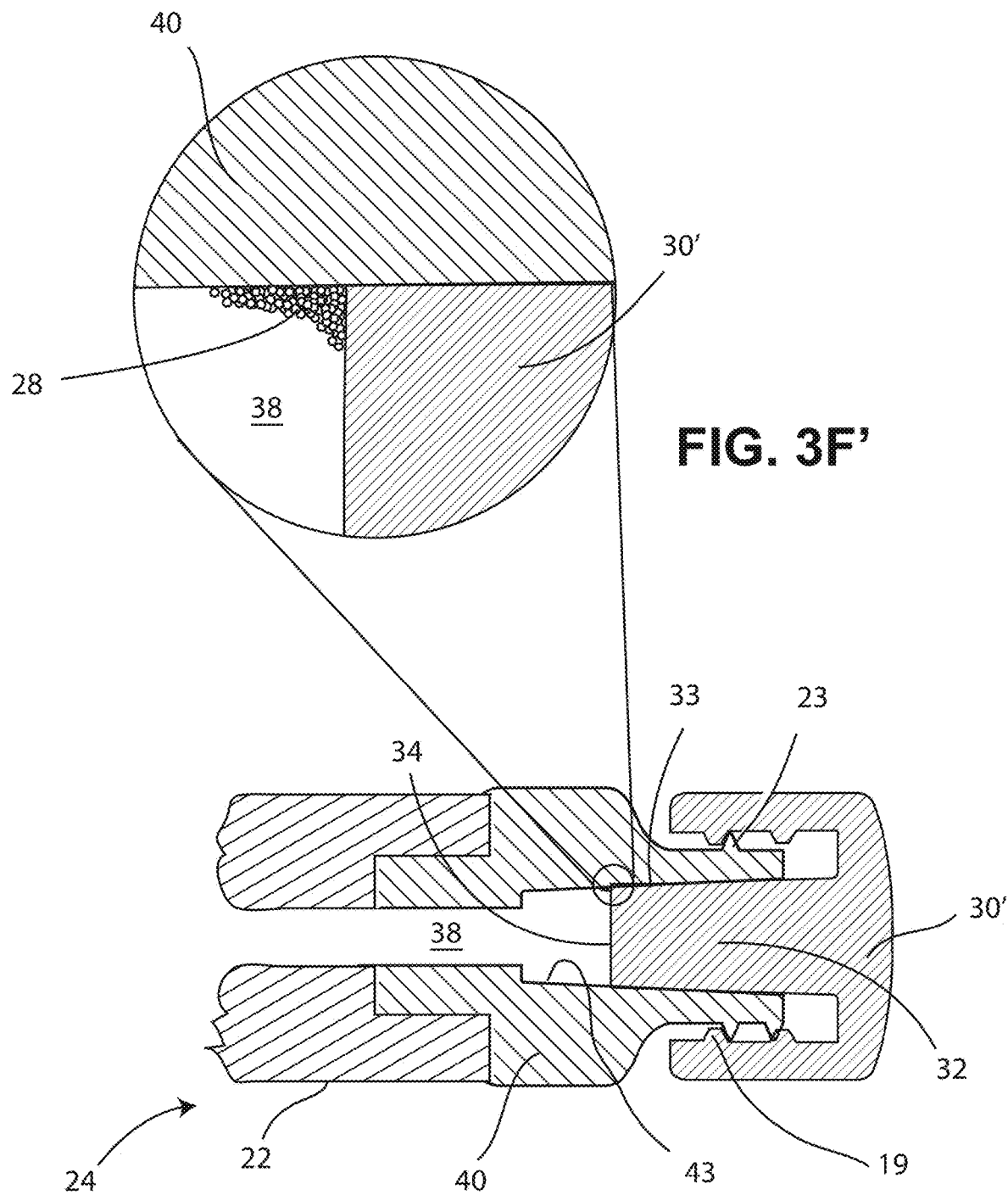
FIG. 3F is a cross-sectional sliced view of the proximal end of the peritoneal catheter with the new male cap installed of FIG. 3E after a period of time.

FIG. 3E is a cross-sectional sliced view of the proximal end of the peritoneal catheter 24 of FIG. 3D with a new male cap 30' installed, and FIG. 3E' is a closeup cross-sectional sliced view of a portion of the proximal end of the peritoneal catheter of FIG. 3E. The new male cap 30' is typically a new, sterilized cap, and not the same male cap 30 shown in FIGS. 3A and 3B because caps are not generally reused. In FIGS. 3E and 3E' it is shown how microbes 28 are pushed into the lumen 38 when a new male cap 30' is installed. This occurs, in part, because a leading edge 36 of a tip 34 of the male luer 32 on the new male cap 30' can push microbes down into the lumen 38 during installation of the male cap 30'. These microbes, which in FIG. 3D were on the tapered inner surface 43, are in FIG. 3E in a position distal to their position in FIG. 3D. The microbes are pushed in by the leading edge 36 of the male luer 32. Even if great care is taken to not scrape the walls of tapered inner surface 43 of the female luer 42, some microbes can be pressed into the lumen 38. Once the new male cap 30' is installed, the catheter or other infusion device is often left alone for hours, days or even weeks, during which time the microbes can multiply and spread further into the lumen 38, as shown in FIGS. 3F and 3F'. FIGS. 3F and 3F' show a cross-sectional sliced view of the proximal end of the peritoneal catheter 24 with the new male cap 30' installed of 3E and 3E', after a period of time during which microbes 28 have increased in population and begun colonizing down the walls of the lumen 38, where they can eventually reach into the patient either by continued growth and/or by becoming released from the walls of lumen 38 during fluid flow and thus flushed into a patient, thereby promoting infection in, and even death of, the patient.

Figure 4A:
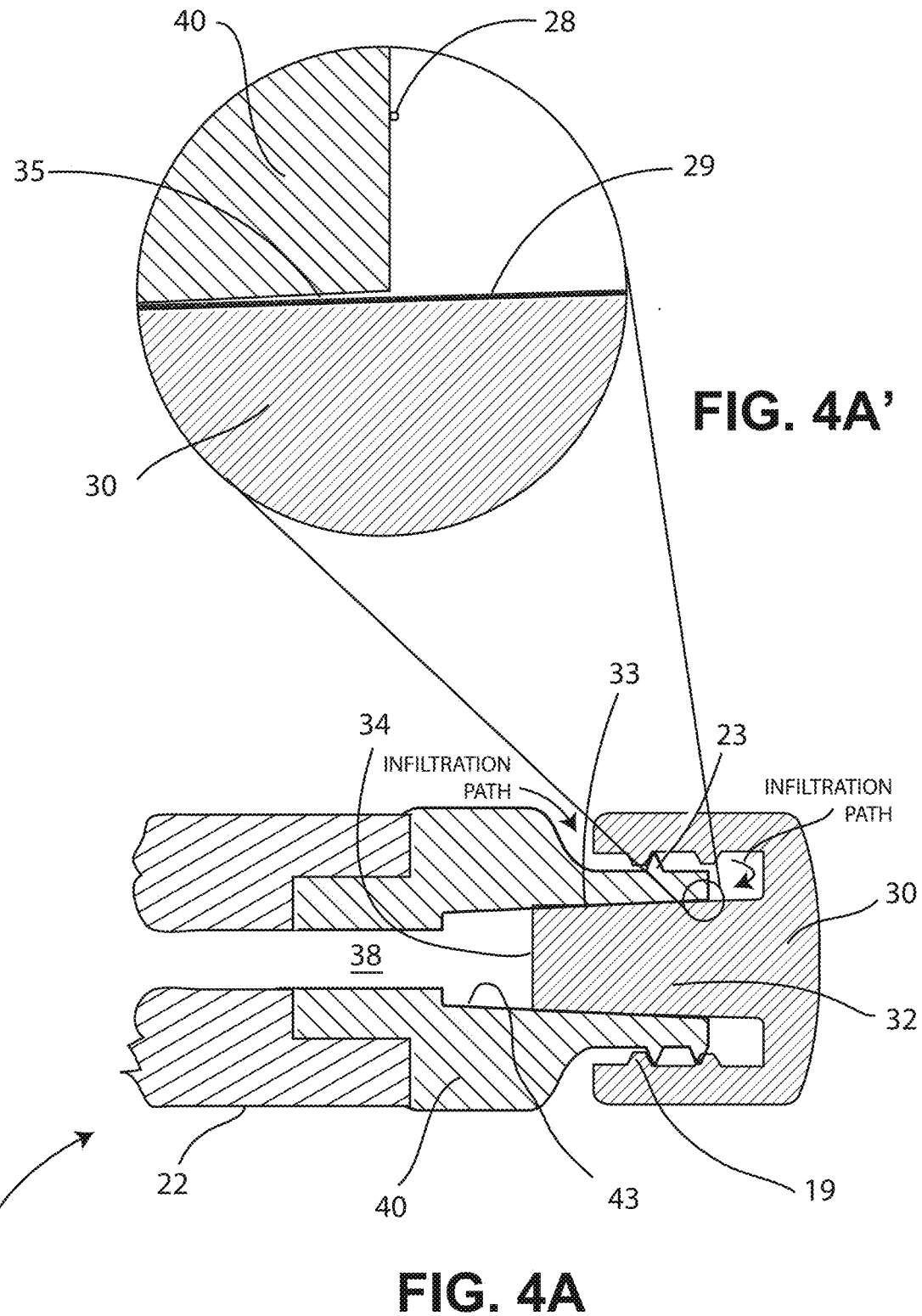
FIG. 4A is a cross-sectional sliced view of a proximal end of a peritoneal catheter with a male cap installed on a female connector.

FIG. 4A is a cross-sectional sliced view of a proximal end of a peritoneal catheter containing a female connector 40, with a male cap 30 installed on the female connector 40; the male cap 30 containing an antimicrobial agent 29 on a male luer 32 of the male cap 30. More specifically, the antimicrobial agent 29 is on the tapered surface 33 of the male luer 32. The antimicrobial agent 29 extends down into a gap 35 (similar to the gap 35 of FIGS. 3A to 3F, but now with the antimicrobial agent 29 present). FIG. 4A' is a closeup cross-sectional sliced view of a portion of the proximal end of the peritoneal catheter of FIG. 4A.

Figure 4B:
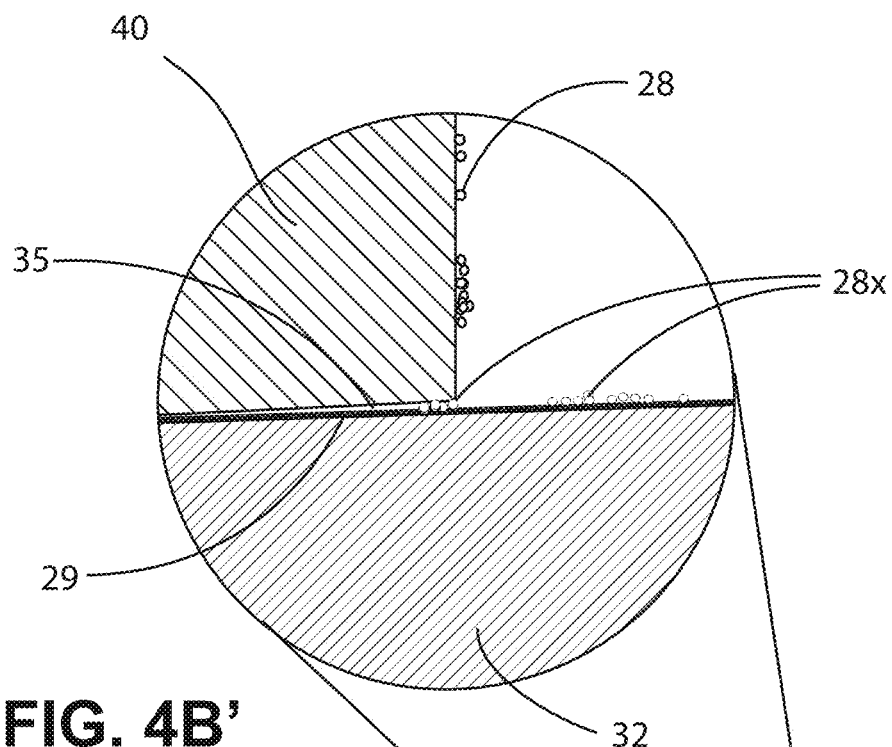
FIG. 4B is a cross-sectional sliced view of the proximal end of the peritoneal catheter, including the female connector, with the male cap installed of FIG. 4A after microbes have infiltrated along a path.
Figure 4B:
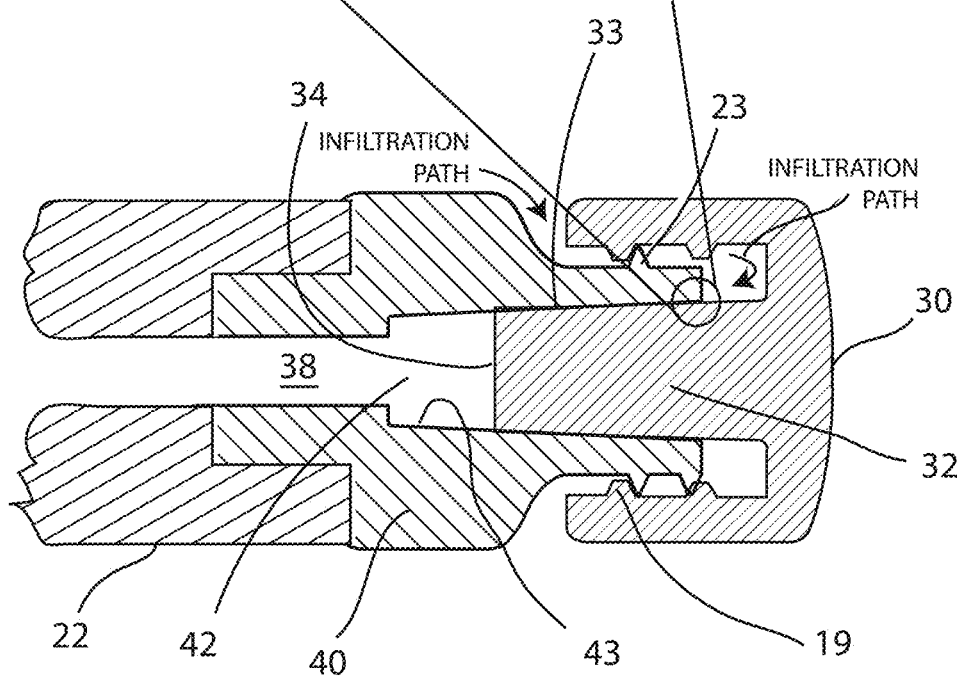

FIG. 4B is a subsequent (in time) cross-sectional sliced view of the proximal end of the peritoneal catheter of FIG. 4A with the male cap 30 installed, and FIG. 4B' is a closeup cross-sectional sliced view of a portion of the proximal end of the peritoneal catheter of FIG. 4B. In FIGS. 4B and 4B' the microbes that make contact with the antimicrobial agent 29 are represented as being dead microbes 28x. Thus, the number of surviving microbes 28 present is significantly smaller due to the antimicrobial agent 29. The microbes 28 and dead microbes 28x are shown as a schematic representation, rather than showing actual living or dead microbes drawn to scale. The dead microbes 28x thus represent either dead microbes themselves, as well as places where microbes have infiltrated and died (and possibly then fallen away or otherwise moved). Thus, FIGS. 4B and 4B' show how the presence of antimicrobial on the infiltration path can reduce microbes at the interface between the tapered surfaces of the male and female luers 32, 42, thereby preventing movement and growth of microbes down the infiltration path.

Figure 4C:
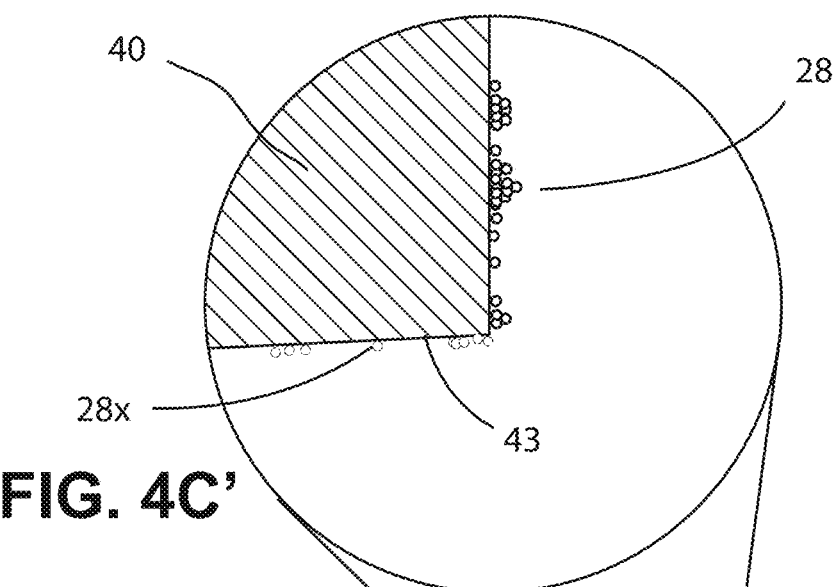
FIG. 4C is a cross-sectional sliced view of the proximal end of the peritoneal catheter, including the female connector, of FIG. 4B with the male cap removed.
Figure 4C:
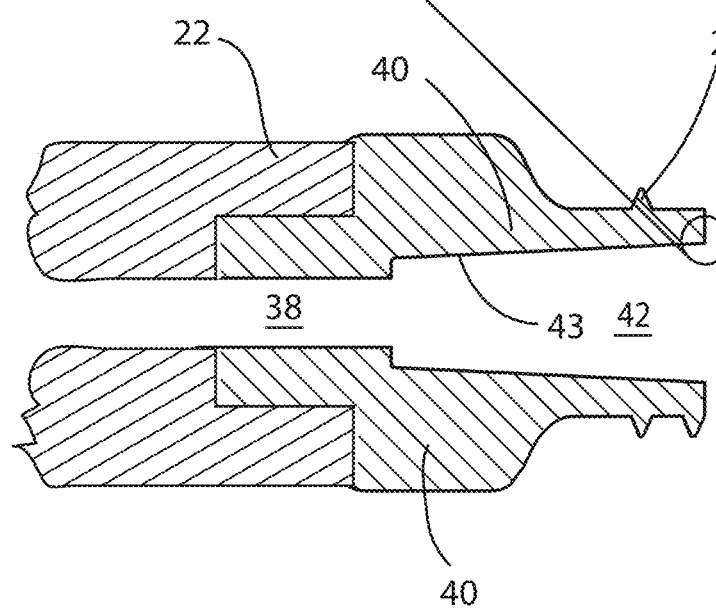

FIGS. 4C and 4C' show the end of the female connector 40 of FIGS. 4A and 4A' after removal of the male cap, showing dead microbes 28x on the tapered inner surface 43 of the female luer 42 of the female connector 40. Even though there are (in this embodiment) some microbes 28 on the proximal end of the female connector 40, the microbes on the tapered portions of the female luer 42 are shown dead (meaning they can be microbes that have been killed by the antimicrobial and/or can be places where microbes did not grow).

Figure 4D:
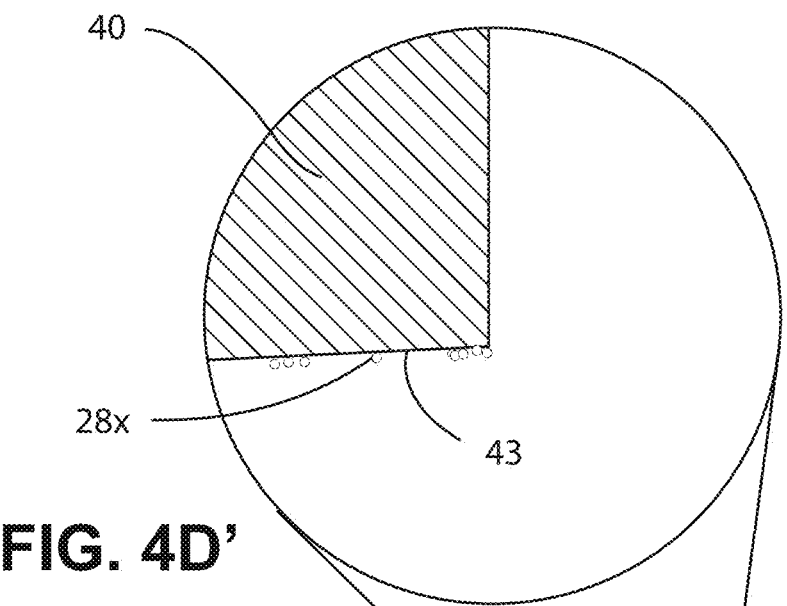
FIG. 4D is a cross-sectional sliced view of the proximal end of the peritoneal catheter of FIG. 4C, including the female connector, after cleaning.
Figure 4D:
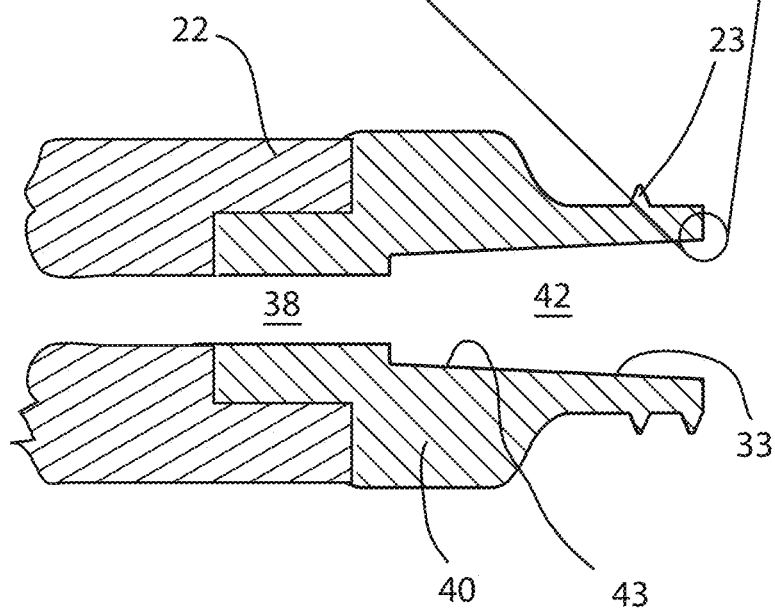
Figure 4E:
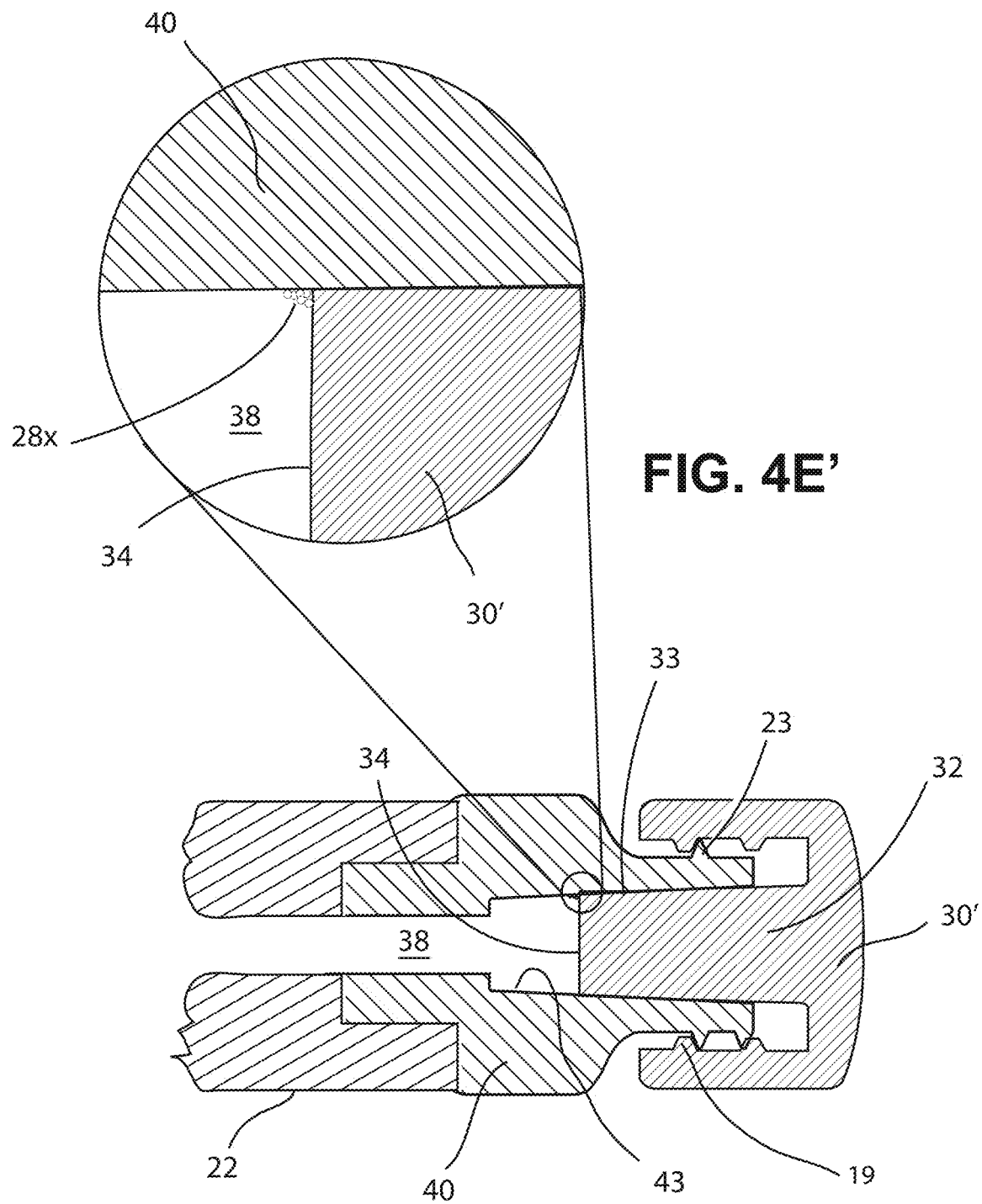
FIG. 4E is a cross-sectional sliced view of the proximal end of the peritoneal catheter of FIG. 4D, including the female connector, with a new male cap coupled to the female connector.
Figure 4F:
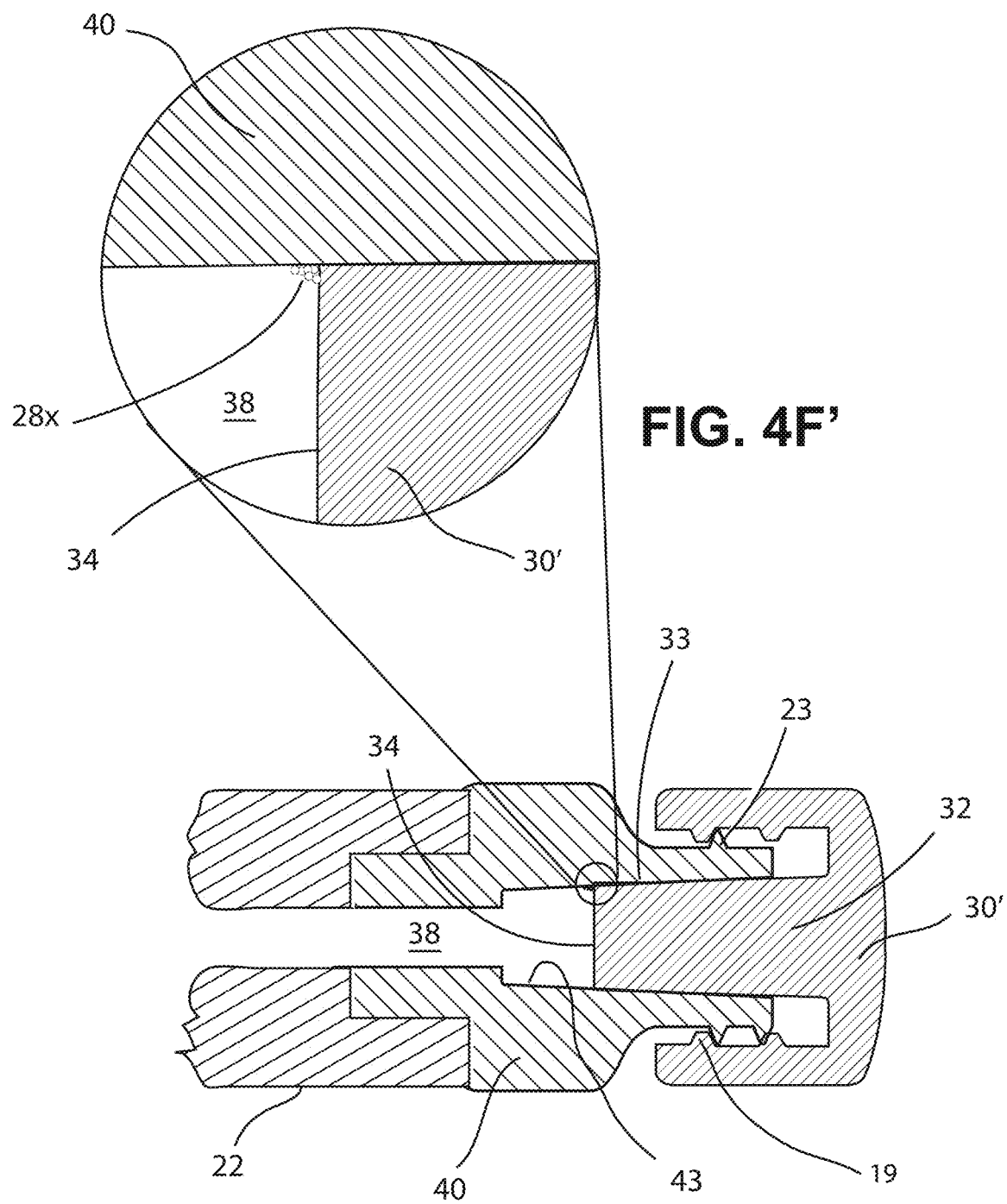
FIG. 4F is a cross-sectional sliced view of the proximal end of the peritoneal catheter with the new male cap installed of FIG. 4E after a period of time.

FIGS. 4D and 4D' show the female connector of FIGS. 4C and 4C' after cleaning the end of the female connector 40. In contrast to early FIGS. 3D and 3D', both the end and interior of the female connector 40 are free (or substantially free) of living microbes. Thereafter, upon insertion of a new male cap 30', as shown in FIGS. 4E and 4E', dead microbes 28x are pushed into the lumen 38, but these dead microbes 28x fail to grow, as shown in FIGS. 4F and 4F' (which represent a subsequent period in time, such as 48 to 72 hours, after the point shown in FIGS. 4E and 4E').

Figure 5:
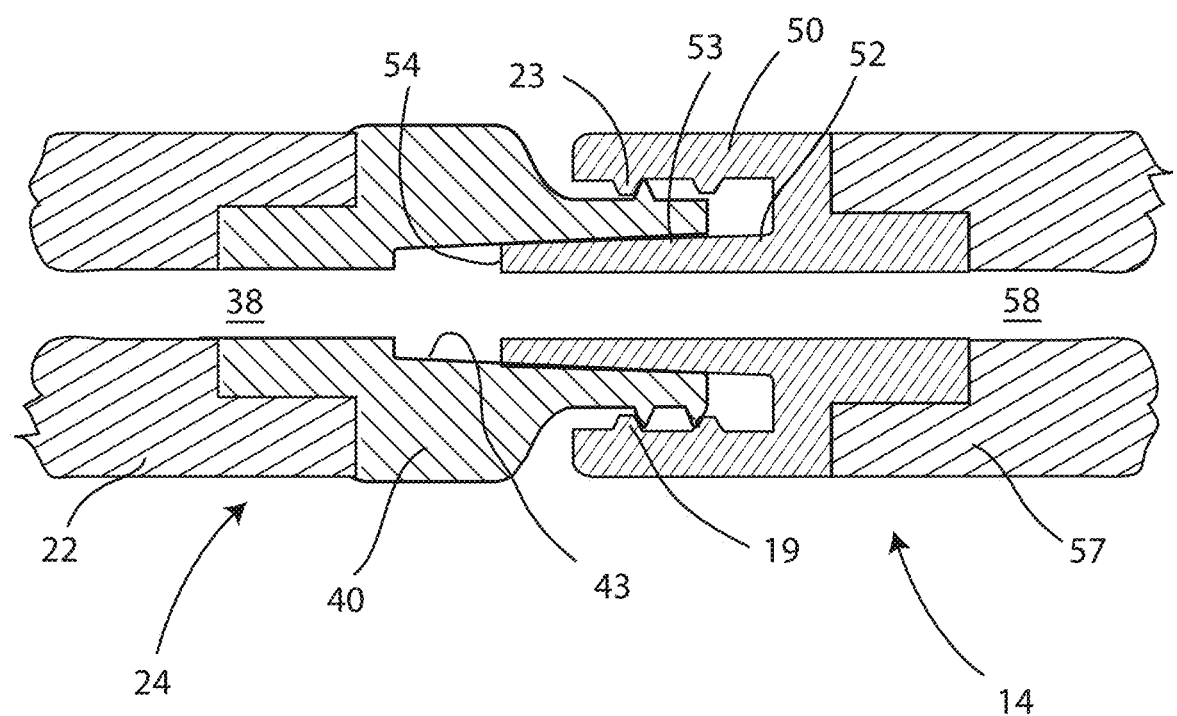
FIG. 5 is a closeup cross-sectional sliced view of a coupling showing a female connector on a proximal end of a peritoneal catheter with a male connector on a distal end of a transfer set.

FIG. 5 is a closeup cross-sectional sliced view of a proximal end of a peritoneal catheter 24 with a distal end of a transfer set 14 connected. FIG. 5 corresponds generally to the dialysis stage of FIG. 2C, wherein the transfer set allows for fluid to flow between the dialysis solution and into and out of the patient's peritoneal cavity. In FIG. 5 a female connector 40 of the peritoneal catheter 24 is joined to a male connector 50 of the transfer set 14. The transfer set 14 further comprising a tube 57 (such as a tube for transferring dialysis fluid) that is attached to male connector 50. The male connector 50 comprises a male luer 52 with a tapered outer surface 53, and threads 23. Tube 57 includes an inner lumen 58. The male luer 52 of male connector 50 includes the tapered outer surface 53 that has a truncated conical surface, along with a tip 54. This design, similar to those shown in FIG. 3A to 3F, is also subject to infiltration and ingrowth of microbes, resulting in infections in a patient.

The same principals of antimicrobial use in FIGS. 4A to 4F, in which the male luer 52 includes an antimicrobial, can be used to control microbial infiltration and growth and subsequent infections, specifically inclusion of a coating of antimicrobial agent on the outside of the male luer 52, such as at the distal end or intermediate portion of the male luer 52, or both (for example).

Figure 6A:
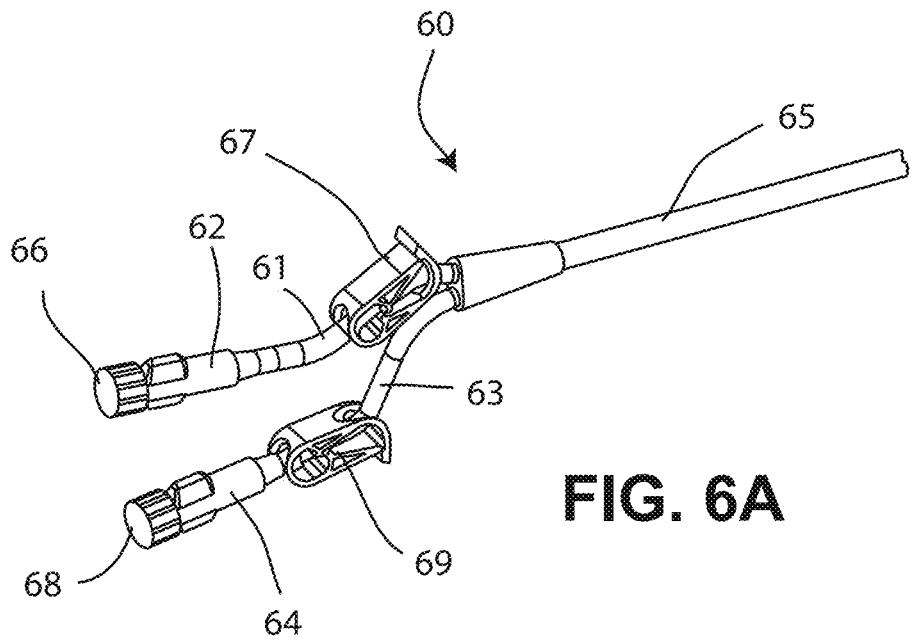
FIG. 6A is a perspective view of a hemodialysis catheter, showing the hemodialysis catheter with two female connectors to which male caps have been coupled.
Figure 6B:
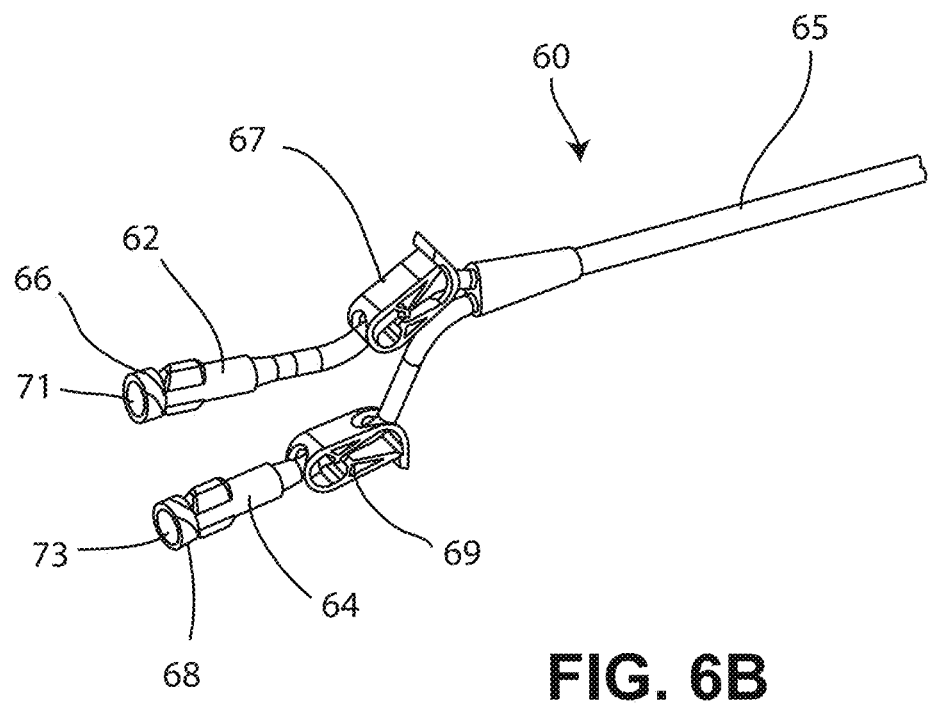
FIG. 6B is a perspective view of the hemodialysis catheter of FIG. 6A, showing the hemodialysis catheter with the two female connectors having the male caps removed.

FIGS. 6A and 6B show an alternative infusion device, in this case a proximal end of a hemodialysis catheter 60 with female connectors 62, 64 and two tubes 61, 63 containing internal lumens (not shown) that run down the main section 65 of the catheter 60. FIG. 6A is a perspective view of the hemodialysis catheter, showing the hemodialysis catheter with two female connectors 62, 64 having caps 66', 68' installed. The hemodialysis catheter 60 is also shown with clamps 67, 69, the clamps shown in a closed orientation. The clamps 67, 69 are open during dialysis, but then closed between dialysis sessions and when the caps 66 68 are being removed and inserted. FIG. 6B is a perspective view of the hemodialysis catheter 60, showing the hemodialysis catheter with two female connectors 62, 64 having caps removed. Threaded caps 66, 68 of the female connectors 62, 64 are shown, as well as female luers 71, 73.

Figure 7A:
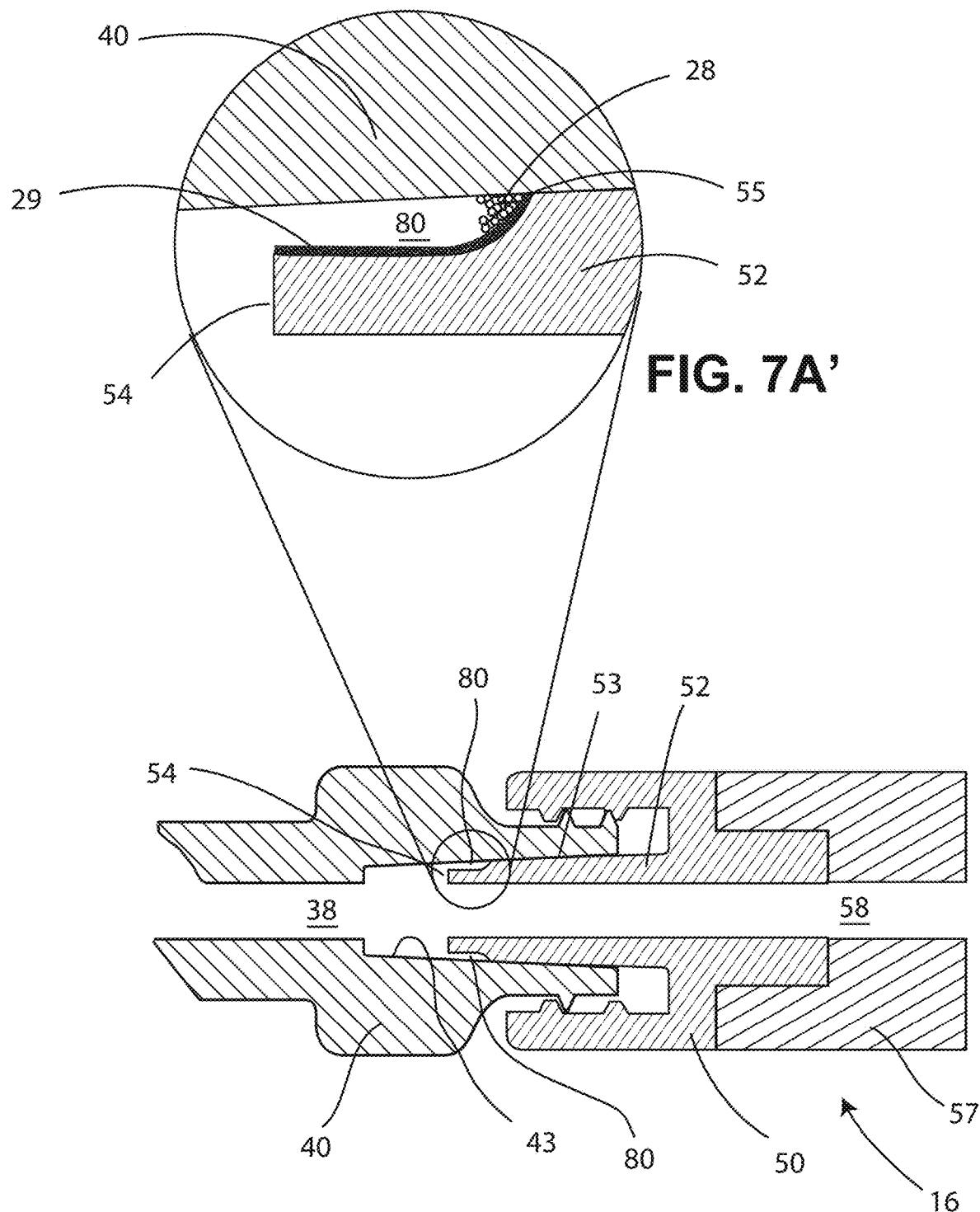
FIG. 7A is a partial cross-sectional view of a female connector having an infusion set connected, the infusion set comprising a male connector having a male luer including a distal recess configured for delivery of an antimicrobial agent.

FIG. 7A is a partial cross-sectional view of an infusion set 16 connected to a female connector 40. The infusion set 16 has a male connector 50 and a tube 57. The male connector 50 has a male luer 52, the male luer 52 includes a distal recess 80 configured for delivery of an antimicrobial agent 29 (shown in FIG. 7B'). Female connector 40 includes a lumen 38 in fluid connection to lumen 58 in tube 57. The male luer 52 includes a tapered outer surface 53 that has a partial conical surface, along with a tip 54. Near the tip 54 is a distal recess 80 containing the antimicrobial agent 29 (shown in FIG. 7A'), such as chlorhexidine. The antimicrobial agent 29 is typically a dry-antimicrobial, and provides an antimicrobial effect to the interior of the female connector 40, especially at the region in the vicinity of the distal recess 80 of the male luer 52, and the area around where it meets the tapered inner surface 43 of the female luer 42 of the female connector 40. As the male luer 52 is inserted into the female connector 40, the microbes 28 are pushed by proximal edge 55 of the distal recess 80 rather than tip 54; thus, the microbes 28 are concentrated within the distal recess 80 near proximal edge 55. The antimicrobial agent 29 may become wetted by fluid from lumens 58 and 38 when male connector 50 was connected with female connector 40. However, the fluid is (in certain embodiments) substantially retained within the distal recess 80 even when fluid flows through the male connector 50 (which includes the male luer 52) because the distal recess 80 only has one opening (at the distal end of the distal recess 80 near tip 54). This results in a high concentration of antimicrobial agent in the fluid in the distal recess 80 without substantially depleting the antimicrobial agent 29 from the male luer 52. Thus, the antimicrobial agent within the fluid in the distal recess 80 is at a lethal concentration for a sufficient time to kill the microbes 28.

FIG. 7B is a partial cross-sectional view of the male connector and female connector of 7A after a period of time. FIG. 7B' is a closeup cross-sectional sliced view of a portion of the male and female luers of FIG. 7B. The microbes 28x are dead after being in contact with the antimicrobial agent 29 within the distal recess 80 for the period of time. The dead microbes 28x will not multiply and will not cause an infection to a patient.

FIG. 8 is a partial cross-sectional view of an infusion set 16; the infusion set 16 including a male connector 50 and a tube 57, the male connector 50 comprising a male luer 52 including a distal recess 80, a tip 54 and an intermediate recess 82 configured for delivery of an antimicrobial agent. FIG. 8' is a close-up of an intermediate recess 82 of the male luer 52. The male luer 52 includes a tapered outer surface 53 that has a truncated conical surface. Near the tip 54 is the distal recess 80 containing an antimicrobial agent 29, and the intermediate recess 82 set back proximal from the tip 54. The antimicrobial agent 29 is typically a dry-antimicrobial. FIG. 8' shows the intermediate recess 82, along with edges 83 and 84 of the recess. In some implementations the edges 83, 84 are smooth transitions with the tapered outer surface 53 of the male luer 52, while in other implementations the edges 83, 84 are more pronounced and defined, as shown in FIG. 8'. In one embodiment, edge 83 is removed and intermediate recess 82 continues distally until reaching the unmodified tapered outer surface 53; this is for ease of injection molding. The infusion set 16 may be used to connect to a female connector (not shown); thus providing similar infection prevention benefits described elsewhere herein.

FIG. 9 is a partial cross-sectional view of a portion of an infusion device 20 connected to a female connector 40. The infusion device 20 including a tube 57 joined to a male connector 50; the male connector 50 comprising a male luer 52 having a tapered outer surface 53. The male luer 52 of the male connector 50 includes an intermediate recess 82 in the tapered outer surface 53 containing an antimicrobial agent 29 and configured for delivery of the antimicrobial agent (intermediate recess referring to the recessed portion situated between the distal end and the proximal end of the tapered outer surface 53). The male luer 52 also includes a distal recess 80 at its distal end containing antimicrobial agent 29. FIG. 9' is a closeup partial cross-sectional view of the male luer 52 and female connector 40 of FIG. 9, showing an enlargement of the distal recess 80 of the male luer 52 and female connector 40. Female connector 40 includes a lumen 38 in fluid connection to lumen 58 on tube 57 of the infusion set. The male luer 52 includes a tapered outer surface 53 that has a partial conical surface (a surface that corresponds substantially to the bottom of a cone), along with a tip 54. Near the tip 54 is the distal recess 80 containing antimicrobial agent 29.

FIG. 9" is a closeup partial cross-sectional view of the male luer 52 and the proximal end of the female connector 40 and the intermediate recess 82 of the male luer 52. In FIG. 9" the proximal edge 84 of intermediate recess 82 is shown. This proximal edge 84 can be, for example, a defined indent or a simple taper. The intermediate recess 82 extends both proximally and distally from a proximal-most end of the tapered inner surface 43 of the female connector 40; thus providing a region for retaining a high concentration of the antimicrobial agent, which is retained by surface tension while the antimicrobial agent is in a dissolved state (or partially dissolved state) in a fluid. The antimicrobial reverts back to a dry-antimicrobial after the fluid had dried, with at least a portion of the antimicrobial agent being retained in the intermediate recess.

The antimicrobial agent is typically a dry-antimicrobial, and provides an antimicrobial effect to the interior of the female connector 40, especially at the region in the vicinity of the distal recess 80 of the male luer 52, the intermediate recess 82, and the overlapping region 41 (overlap of the tapered inner surface 43 and the tapered outer surface 53). When the male luer 52 of the male connector 50 is inserted into the female luer 42 of the female connector 40, the microbes 28 are pushed by proximal edge 55 of the distal recess 80 rather than tip 54; thus the microbes 28 are concentrated within the distal recess 80. The antimicrobial agent 29 may become wetted by fluid in lumens 38 and 58 as the fluid flows into the recess while connecting male connector 50 to female connector 40. However, after connection, the fluid is substantially retained within the distal recess 80 even when fluid flows through the male connector 50 because the distal recess 80 only has one opening (at the distal end of the recess). This results in a high concentration of antimicrobial agent in the fluid in the distal recess 80 without substantially depleting the antimicrobial agent 29 from the male connector 50. Thus, the antimicrobial agent within the fluid is at a lethal concentration for a sufficient time to kill the microbes 28. The proximal edge 84 of intermediate recess 82 is located proximal to the proximal end of tapered inner surface 43, but can optionally be located distal to the proximal end of the tapered inner surface 43 of the female luer 42. Some benefits of intermediate recess 82 as shown in FIG. 9 are it provides a reservoir of antimicrobial agent 29 at the proximal end of the female connector 40 (killing the microbes where they enter) and, at the same time, it reduces the stress on the proximal end of the female connector 40, thus preventing stress cracking of the female connector.

In an example embodiment, the antimicrobial agent is located along the entire tapered outer surface 33, in the recesses 80, 82 and along male connector threaded surface 39 of a male connector 50 (the male connector threaded surface 39 including the proximal most surface that is adjacent to the proximal end of the tapered outer surface 33). The flow of a fluid in the lumen 38 is stopped by activating a first clamp, valve or other flow-stopping means (not shown) located distal to the female connector 40, and flow of a fluid in the lumen 58 is stopped by activating a second clamp, valve or other flow-stopping means (not shown) located proximal to the male connector 50. Prior to connecting the male connector 50 to the female connector 40, the first and second clamps are activated to prevent fluid flow within the lumens 38, 58. After activating the clamps, and as the male luer 52 is inserted into the female luer 42, the fluid inside the lumens 38, 58 is displaced creating an outward flow of the fluid between the tapered surfaces 43, 53 and into a channel 59 located outside the female connector 40 and inside the male connector threaded surface 39. As the fluid flow contacts the antimicrobial agent, a portion of the antimicrobial agent is dissolved and incorporated into the fluid; thus creating an antimicrobial fluid. The antimicrobial fluid then flows into the channel 59 where it contacts the proximal end 48 and the female connector threaded surface 49, which subsequently kills microbes (not shown in FIG. 9, but similar to the microbes 28 shown in FIGS. 3B', 3C' and 4C') on the female connector proximal end 48 and threaded surface 49. This is beneficial for killing microbes that may remain after cleaning the female connector proximal end 48 and threaded surface 49 with a wipe as described in the narrative of FIGS. 3D' and 4D'. Over time, the antimicrobial fluid will dry, leaving a dry antimicrobial agent coating on the female connector 40 at the female connector proximal end 48 and threaded surface 49; thus creating an antimicrobial female connector in-situ. The antimicrobial is, for example, chlorhexidine acetate, which is dry and has a persistent antimicrobial effectiveness. In comparison, an alcohol antimicrobial, as found in many prior art devices, typically has no persistent antimicrobial effectiveness after the alcohol antimicrobial dries. As saline contacts chlorhexidine acetate, some of the chlorhexidine acetate is converted to chlorhexidine dihydrochloride, which adheres to the surfaces of the female connector; thus providing antimicrobial properties to the female connector in-situ.

In some embodiments it is desirable to apply a slowly dissolving ("time-release") coating on top of the antimicrobial agent to delay or slow the time for the antimicrobial agent to dissolve. A time-release coating, especially when applied to distal recess 80, is advantageous for ensuring a precise dose of antimicrobial agent is available within the distal recess 80 after the connectors 40, 50 have been coupled together. In another embodiment it is desirable to use an antimicrobial mixture to slow the antimicrobial mixture's dissolution rate; the antimicrobial mixture comprising the antimicrobial agent and a material that dissolves slower, such as a hydrophilic water-soluble polymer. In yet another embodiment it is desirable to use chlorhexidine base with a chlorhexidine salt (such as chlorhexidine acetate) to achieve the intended dissolution rate; thus providing a means and method to control the amount of antimicrobial agent being removed from the recesses 80, 82 and tapered outer surface 53, transferring a portion of the antimicrobial agent to the female connector proximal end 48 and female connector threaded surface 49, where upon drying, a portion of the antimicrobial agent remains on the female connector proximal end 48 and female connector threaded surface 49. The benefit is this provides a persistent antimicrobial agent along the infiltration path (as shown in FIG. 3A) to prevent microbe ingress and subsequent infections.

Figure 10:
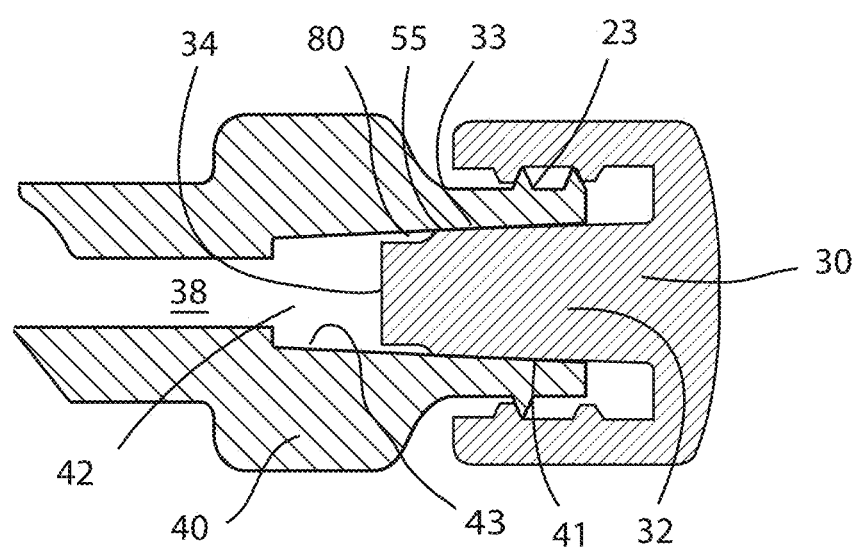
FIG. 10 is a partial cross-sectional view of a female connector having a male cap installed, the male cap comprising a male luer including a distal recess containing an antimicrobial agent and configured for delivery of the antimicrobial agent.

FIG. 10 is a partial cross-sectional view of a female connector 40 having a male cap 30 installed; the male cap 30 comprising a male luer 32 including a distal recess 80 containing an antimicrobial agent; the male cap 30 configured for delivery of the antimicrobial agent. Female connector 40 includes a lumen 38. The male luer 32 includes a tapered outer surface 33 that has a truncated conical surface, a tip 34, and near the tip 34 is a distal recess 80 containing the antimicrobial agent, such as chlorhexidine. In one embodiment, the distal recess 80 is a truncated conical surface that is recessed 0.001" to 0.015" below a projection of the tapered outer surface 33. The antimicrobial agent is typically a dry-antimicrobial that is water soluble, and provides an antimicrobial effect to an overlapping region 41 (overlap of a tapered outer surface 33 of a male luer 32 of the male cap 30 and the tapered inner surface 43 of a female luer of the female connector), especially at the region in the vicinity of the distal recess 80 of the male luer 32. As the male luer 32 is inserted into the female luer 42 of the female connector 40, microbes are pushed by the proximal edge 55 of the distal recess 80 rather than tip 34; thus the microbes are concentrated within the distal recess 80. The antimicrobial agent in distal recess 80 may become wetted by fluid in lumen 38 being displaced as male luer 32 is inserted into female luer 42. The fluid is substantially locked within the distal recess 80 in some embodiments because the distal recess 80 only has one opening (at the distal end of the recess) after the male luer 32 is fully inserted into the female connector 40. This results in a high concentration of antimicrobial agent in the fluid in the distal recess 80 without substantially depleting the antimicrobial agent. Thus, the antimicrobial agent within the fluid is at a lethal concentration for a sufficient time to kill the microbes and prevent ingrowth of microbes.

Figure 11:
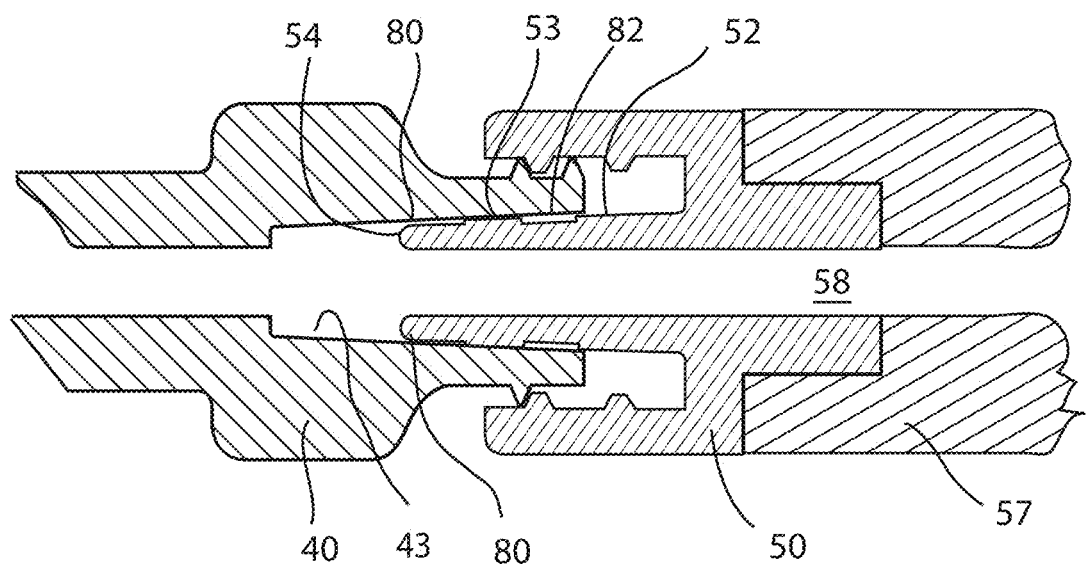
FIG. 11 is a partial cross-sectional view of a female connector having an infusion set connected, the infusion set comprising a male connector with a male luer including a distal recess containing an antimicrobial agent and an intermediate recess containing an antimicrobial agent.

FIG. 11 is a partial cross-sectional view of a female connector 40 having an infusion set connected, the male connector 50 having a male luer 52 including a portion of tapered surface 53 having an intermediate recess 82 containing an antimicrobial agent 29 and configured for delivery of the antimicrobial agent. Near the tip 54 is the distal recess 80 containing an antimicrobial agent, and the intermediate recess 82 is set back proximal from the tip 54 and also contains an antimicrobial agent.

Figure 12:
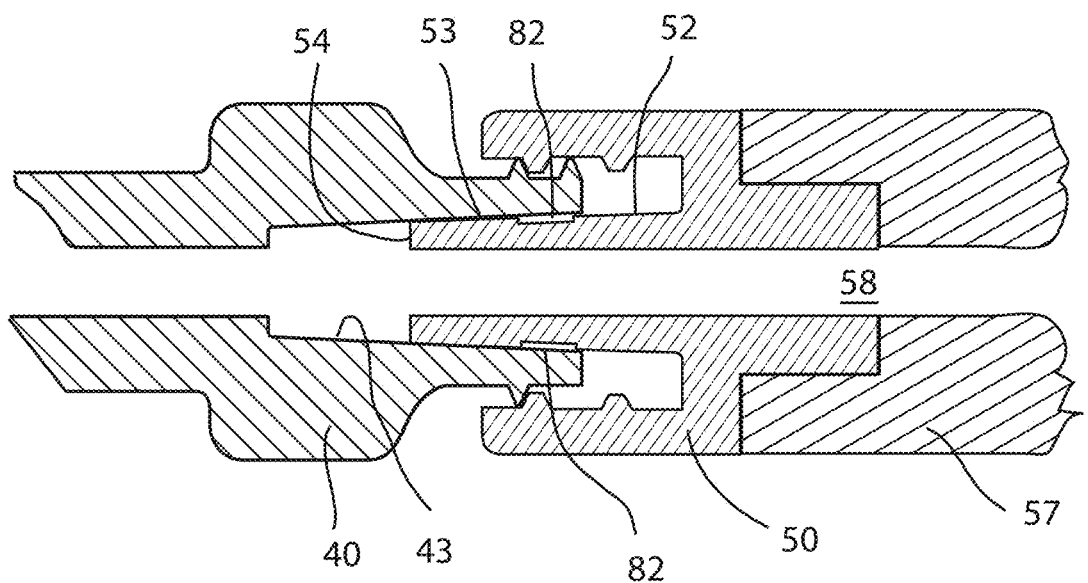
FIG. 12 is a partial cross-sectional view of a female connector having an infusion set connected, the infusion set having a male connector with a male luer including an intermediate recess containing an antimicrobial.

FIG. 12 is a partial cross-sectional view of a female connector 40 having an infusion set connected. The male luer 52 of the male connector 50 includes a tapered outer surface 53 that has a partial conical surface, along with a tip 54. The male luer including an intermediate portion containing an antimicrobial. The intermediate portion of the tapered surface 53 also has an intermediate recess 82 containing an antimicrobial composition; the male luer 52 configured for delivery of the antimicrobial agent (the "intermediate portion" refers to the tapered portion between the distal end of the tapered outer surface 53 and the proximal end of the tapered outer surface 53).

Figure 13:
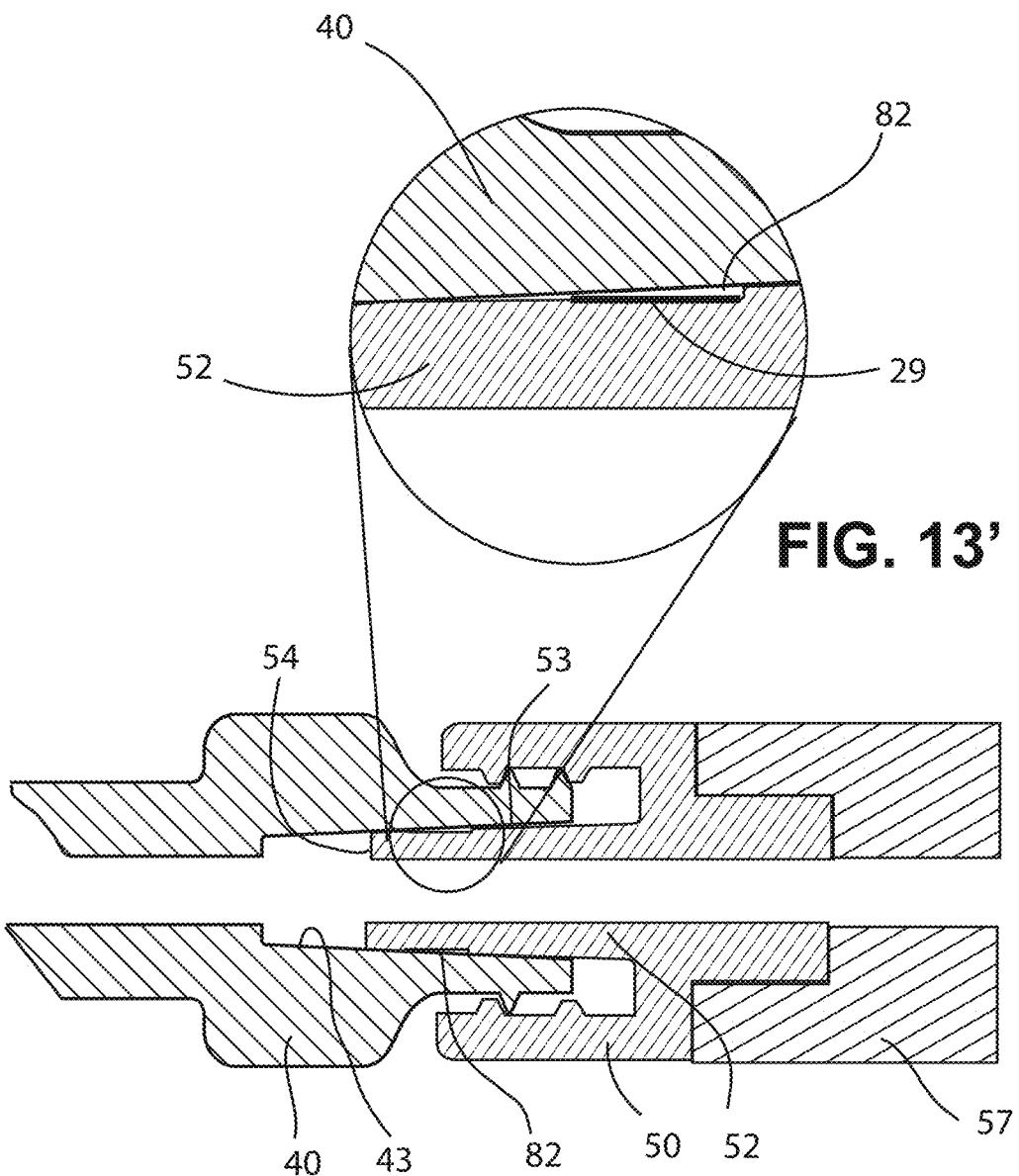
FIG. 13 is a partial cross-sectional view of a female connector having an infusion set connected, the infusion set having a male connector with a male luer including an intermediate recess containing an antimicrobial.
Figure 15E:
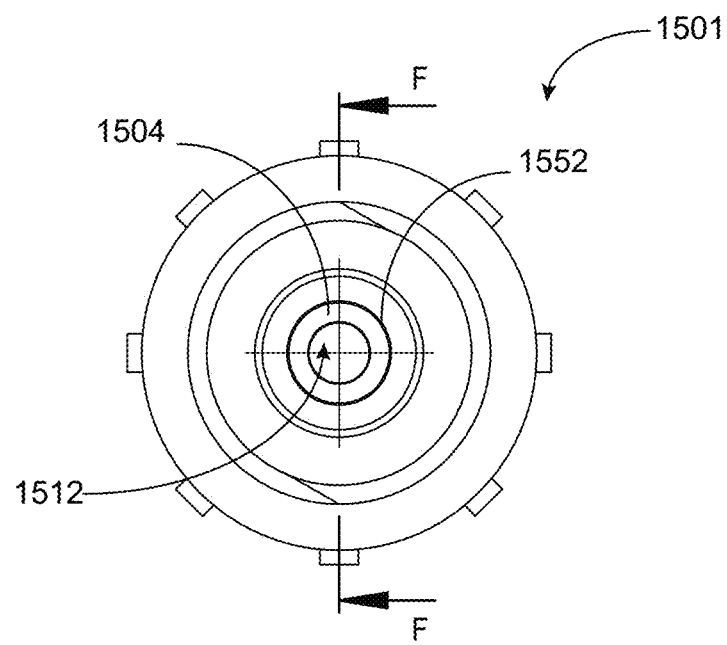
FIG. 15E is an end view of the male luer connector of FIG. 15A.
Figure 15F:
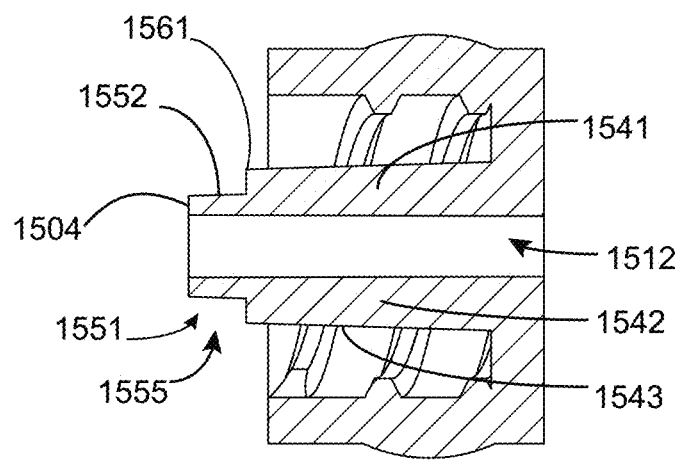
FIG. 15F is a cross-sectional view of the male luer connector of FIG. 15A along line F-F of FIG. 15E.

FIG. 13 is a partial cross-sectional view of an infusion set connected to a female connector 40, a male luer 52 of a male connector 50 of the infusion set including an intermediate recess 82 of a tapered outer surface 53 containing an antimicrobial agent 29 and configured for delivery of the antimicrobial agent. The tapered outer surface 53 also contains the antimicrobial. FIG. 13' is a closeup partial cross-ssectional view of the female connector 40 connected to the infusion set of FIG. 13, showing an enlargement of the female connector 40 and an intermediate recess 82 of the male luer 52. Female connector 40 includes a lumen in fluid connection to a lumen on tube 57. The male luer 52 includes a tapered outer surface 53 that has a truncated conical surface, along with a tip 54. The intermediate recess 82 is set back proximal from the tip 54 and includes an antimicrobial agent 29, as shown in FIG. 13'.

It will be noted that in some cross-sectional figures the illustrations have been simplified, such as removal of the background threads on the sealing cover to make the various aspects of the invention more apparent.

It will be appreciated that this is just an illustrated example, and that alternative peritoneal dialysis configurations are possible. Also, it will be appreciated that peritoneal dialysis is just one example of a use for the infusion connectors and systems disclosed herein, and that alternative uses and systems include hemodialysis catheters, peripherally inserted central catheters, midline catheters, drainage catheters, needleless connectors, intravenous (IV) administration sets, peritoneal dialysis lines, bloodlines, syringes, valves and filters.

In an embodiment, the antimicrobial agent is chlorhexidine acetate, with the male luer having distal and intermediate recesses containing approximately 25 to 250 µg of chlorhexidine acetate on the male luer. This invention provides benefit over prior art from a safety standpoint because, by delivering the antimicrobial agent between the luer surfaces, only a small amount of antimicrobial agent is required to kill microbes. The concentration of antimicrobial agent is high (note: a concentration of >200 µg/mL of chlorhexidine acetate is desired to quickly kill most microbes, including gram positive, gram negative and fungi), but the total dose is low because there is a very small gap between the luer surfaces and little to no flow/loss of the antimicrobial away from this region. A low dose is required for safety because it reduces patient risk in the event antimicrobial is injected into the body. For example, chlorhexidine acetate dose of 500 µg or higher may be considered safe for direct injection into a 60 kg person's bloodstream; a dose significantly below this level is desirable for additional safety or for use in neonates. In addition, in an embodiment the depth of the recess is approximately 0.005" and is approximately 0.020" to 0.040" long, which creates a volume of approximately 1 µL. If 10 µg is in a 1 µL volume, the antimicrobial concentration is 10,000 µg/mL, which is well above the minimum desired level of 200 µg/mL. This demonstrates how the invention can create very high microbe kill efficacy (10,000 µg/mL is 50× higher than the desired minimum of 200 µg/mL) while at the same time providing excellent patient safety (50 µs on the entire male luer is 10× lower than the maximum dose of 500 µg that is desired for patient safety).

The antimicrobial compositions should kill and/or provide stasis of Gram-positive and Gram-negative bacteria and fungi. The agents may also have efficacy at killing organisms within an established biofilm and/or degrading the extracellular matrix of the film. However, this is not necessary for the invention to be beneficial because the invention is designed to kill organisms before they have an opportunity to form a biofilm. The antimicrobial composition can be chlorhexidine acetate, also known as chlorhexidine diacetate. Other compounds containing chlorhexidine may be used (such as chlorhexidine free base, chlorhexidine gluconate and chlorhexidine with dyes). Chlorhexidine acetate has an advantage over chlorhexidine gluconate because the risks associated with para chloroaniline may be minimized. Other suitable antimicrobial compositions may also be used. In general, the antimicrobials are soluble in water, they have a history of clinical use with a demonstrated safety profile, they are antibiotic-free, they can be applied onto a medical device, and they can be subsequently dissolved into a composition having an effective concentration to inhibit growth of bacterial and fungal organisms. Suitable materials include chlorhexidine, chlorhexidine salts (such as chlorhexidine acetate or chlorhexidine gluconate), tetrasodium ethylenediaminetetraacetic acid (tetrasodium EDTA), sodium citrate (yielding a concentration of 30% or higher), iodine, taurolidine, disodium EDTA, silver compounds (including silver nanoparticles and ions), silver sulfadiazine, and, triclosan.

While one drug or antimicrobial composition may provide relief from a wide range of challenging organisms that could potentially lead to catheter-related bloodstream infection, two or more agents may be used to increase efficacy against a broad range of infectious organisms (bacteria and fungi).

In particular, catheter-related infections arise from three broad classes of organisms: fungi, Gram-negative bacteria, and Gram-positive bacteria. If an antimicrobial composition can be identified that would abate one or two of these types of organisms, while this would certainly be beneficial, it would leave the patient vulnerable to the remaining type(s). By pairing agents with different modes of action, infections by an increased spectrum of organisms can be prevented. This synergy would likely lead to further decreases in catheter-related morbidity and mortality, lessening the impact of the implanted catheter on the patient's quality of life. Example combinations of antimicrobial compositions are chlorhexidine acetate and EDTA, silver sulfadiazine and chlorhexidine acetate, and silver sulfadiazine and methylene blue.

In principle, antibiotics (rifampin, minocycline, etc.) can be incorporated into or onto the male luer or similar device and be as effective as non-antibiotic antimicrobials. However, continuous exposure to one antibiotic can lead to antibiotic resistant bacteria strains, for example, methicillin resistant *S. aureus* (MRSA). Therefore, an example embodiment uses an antimicrobial composition selected from the subset of those which are not antibiotics. If, for some reason, an antibiotic is used, the risk of developing antibiotic resistant strains of bacteria may be mitigated by preparing a second, complimentary, device containing a different antibiotic. By using the two devices in an alternating fashion with successive uses, infectious organisms that are resistant to one antibiotic may be killed by the other.

Needleless Connector (FIGS. 14A-C)

In another aspect described in relation to FIGS. 14A-14C, one implementation of the disclosed technology provides a needleless connector 1411 having a male luer 1441 at a distal end 1408 of the needleless connector 1411. The male luer 1441 includes a tapered sealing member 1442 with a tapered sealing surface 1443. The needleless connector 1411 has a lumen 1412 extending through the needleless connector 1411 through which fluid can flow. At the proximal end 1407 of the needleless connector 1411, threads 1405 are provided for connecting the needleless connector 1411 to another medical device, such as a syringe. At the distal end 1408 of the needleless connector 1411, threads 1402 are provided for coupling the male luer 1441 with a medical device having a female luer, such as the proximal end of a catheter for hemodialysis, peritoneal dialysis, parenteral nutrition, or chemotherapy. The distal tip 1455 also includes a distal tip surface 1433 and a distal end face 1404. The tapered sealing member 1442 has a tapered surface distal edge 1461 adjacent and proximal to the distal tip 1455.

As will be discussed further below, the male luer 1441 includes a distal recess 1451, and the distal tip 1455 has a surface 1452. The surface 1452 can include an antimicrobial agent as described above. As used herein, a distal recess is a void created at the distal tip 1455 of the male luer 1441. The distal tip 1455 is recessed inside the line of taper of the tapered sealing member 1442. As used herein, a line of taper is a representation of an imaginary conical surface defining a conical taper extending beyond the tapered surface distal edge of the male luer.

In the example of FIGS. 14A-14C, the male luer 1441 further includes a plurality of blades 1463 at the distal tip 1455. Between the blades 1463 are a plurality of channels 1467. Blades and channels will be discussed further below.

A number of examples of male luer connectors will now be described in relation to FIGS. 15A-32G. It should be understood that each example below could combined with the proximal end 1407 to create the needleless connector 1411. In addition, each of the male luer connectors described below are not limited to needleless connectors, and could be combined with other medical devices using luer couplings.

Male Luer Connector with Distal recess (FIGS. 15A-F & 16)

Figure 16:
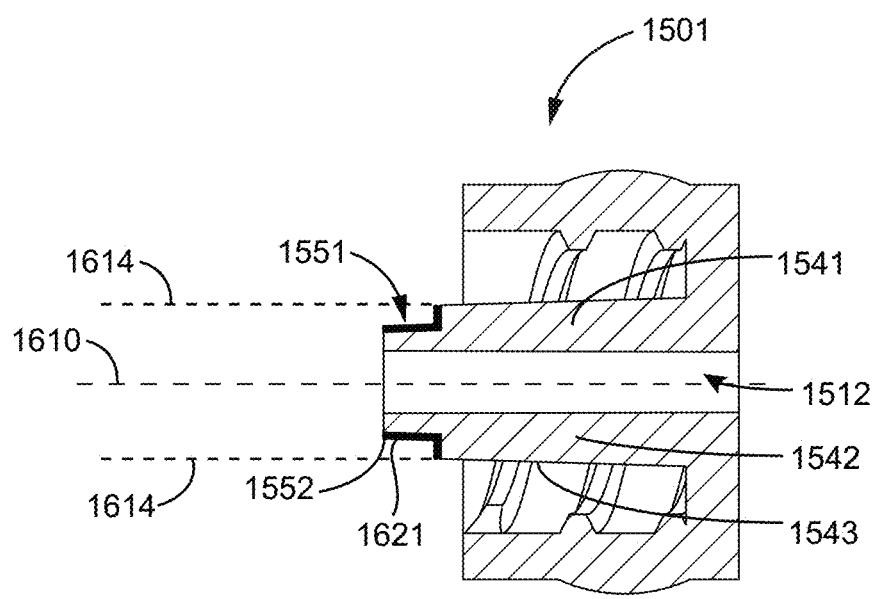
FIG. 16 is a cross-sectional view of a male luer connector according to some examples.

Turning now to FIGS. 15A-16, a male luer connector 1501 includes a male luer 1541. The male luer 1541 comprises a tapered sealing member 1542. The tapered sealing member 1542 has a frustoconical shape that tapers from a larger outer diameter at the proximal portion of the tapered sealing member 1542 to a smaller outer diameter at the distal portion of the tapered sealing member near the tapered surface distal edge 1561. The tapered sealing member 1542 has a tapered sealing surface 1543 that is configured to mate with a female luer to create a fluid tight fit. The male luer connector 1501 further includes threads 1502 that allow the male luer connector 1501 to couple with a female luer connector. A lumen 1512 runs through the male luer connector 1501.

The male luer 1541 includes a distal tip 1555 with an end face 1504. The distal tip 1555 of the male luer 1541 is recessed from the distal line of taper of the tapered sealing member 1542. FIG. 16 is a cross-section of the male luer connector 1501. FIG. 16 illustrates a distal line of taper 1614 extending in a straight line from the tapered sealing surface

1543. The distal line of taper 1614 of the tapered sealing member 1542 is a representation of an imaginary conical surface defining a conical taper extending beyond the tapered surface distal edge 1561 of the male luer 1541. The tapered sealing surface 1543 has a taper angle. In some examples, the taper angle of the tapered sealing member is between about 1.5 degrees and about 2 degrees relative to a central longitudinal axis 1610 of the male luer 1541. In some examples, the taper angle about 1.72 degrees relative to the central longitudinal axis 1610 of the male luer 1541 of the male luer connector 1501. The conical taper defined by the distal line of taper 1614 surrounds the central longitudinal axis 1610 symmetrically.

The distal line of taper 1614 defines an outer diameter of the extension of the tapered sealing surface 1543. A distal recess 1551 is a radially recessed portion of the distal tip 1555, meaning that the distal tip surface 1552 of the distal tip 1555 defines an outer diameter that is smaller than the outer diameter of the extension of the tapered sealing surface 1543. The distal recess 1551 defines a void in the space that is inside of the distal line of taper 1614.

FIG. 16 further shows an antimicrobial composition 1621 coating the distal tip surface 1552 of the distal tip 1555. When the male luer 1541 is coupled with a female luer, the distal tip surface 1552 of the distal tip 1555 does not make contact with the inside surface of the female luer, and a cavity is formed between the distal tip surface 1552 and the female tapered surface, similar to that shown in FIG. 7A. In this cavity, the antimicrobial composition 1621 is able to disperse within the volume created between the distal tip surface 1552 and the female tapered surface.

The male luer 1541 includes a tapered surface distal edge 1561 that defines a proximal edge of the distal tip 1555. When the male luer 1541 is inserted into a female luer, the tapered surface distal edge 1561 of the tapered sealing member 1542 is capable of capturing microbes that may have infiltrated the inner surface of the female luer. As described above in relation to FIG. 7A, antimicrobial agent 1621 kills the microbes within the void between the surface of the female luer and the distal tip surface 1552. In some examples, an antimicrobial agent 1621 is applied to the distal tip surface 1552 by coating, spraying, or dipping the distal tip 1555, although other methods of applying antimicrobial agent are contemplated and are within the scope of the technology. In some examples, antimicrobial agent 1621 is also applied to the tapered sealing surface 1543.

The distal recess 1551 is designed to confine the antimicrobial agent between the inner surface of a female luer and the distal tip surface 1552 so that microbes are exposed to a high antimicrobial concentration. Confinement is a way to keep the antimicrobial agent within the distal recess region during use, while fluid is flowing through the lumen 1512. The distal recess 1551 decreases fluid transfer between the lumen 1512 and the distal tip surface 1552.

Male Luer Connector with Blades (FIGS. 17A-F)

Turning now to FIGS. 17A-F, a male luer connector 1701 includes a male luer 1741. The male luer 1741 comprises a tapered sealing member 1742. The tapered sealing member 1742 has a tapered sealing surface 1743 that is configured to mate with a female luer to create a fluid tight fit. The male luer connector 1701 further includes threads 1702 that allow the male luer connector 1701 to couple with a female luer connector. A lumen 1712 runs through the male luer connector 1701.

The male luer 1741 includes a distal tip 1755 with an end face 1704. The distal tip 1755 of the male luer 1741 is recessed from the distal line of taper of the tapered sealing member 1742. A distal recess 1751 is formed by a recessed portion of the distal tip 1755. When the male luer 1741 is sealed against a female luer and the tapered sealing surface 1743 forms a fluid tight fit with the inside surface of the female luer, the distal tip surface 1752 of the distal tip 1755 does not make contact with the inside surface of the female luer.

The male luer 1741 includes a tapered surface distal edge 1761 that defines a proximal edge of the distal tip 1755. When the male luer 1741 is inserted into a female luer, the tapered surface distal edge 1761 of the tapered sealing member 1742 is capable of capturing microbes that may have infiltrated the inner surface of the female luer.

In some examples, an antimicrobial agent is applied to the distal tip surface 1752 by coating, spraying, or dipping the distal tip 1755 with an antimicrobial agent, although other methods of applying antimicrobial agent are contemplated and are within the scope of the technology. In some examples, antimicrobial agent is also applied to the tapered sealing surface 1743. As described above in relation to FIG. 7A, an antimicrobial agent on the distal tip surface 1752 of the distal tip 1755 kills microbes within the distal recess 1751 between the surface of the female luer and the distal tip surface 1752.

The male luer 1741 further includes multiple blades 1763 arrayed around the distal tip 1755 of the male luer 1741. Between the blades 1763 are a plurality of channels 1767. In the example of FIG. 17, the blades 1763 are elongated projections arranged around the axis of the tapered sealing member 1742, and the channels 1767 are elongated recesses disposed between the blades 1763 and running parallel to the lumen 1712. The blades 1763 and channels 1767 form alternating apexes 1764 and troughs 1768. The distal tip surface 1752 of the distal tip 1755 is defined by the blades 1763 and channels 1767. Furthermore, an antimicrobial agent on the distal tip surface 1752 can be stored within the volumes between the blades 1763. This can increase the amount of antimicrobial agent that can be stored on the distal tip 1755 of the male luer 1741.

In some examples, the distal tip 1755 has a length of about 0.060 inches (1.52 mm). The length of the distal tip 1755 is measured perpendicular to the diameter of the distal tip 1755. In some examples, the lumen 1712 has an inner diameter of about 0.065 inches (1.65 mm). In some examples, the distal tip 1755 has an outer diameter of about 0.095 inches (2.41 mm). In some examples, the wall of the distal tip 1755 has a thickness of about 0.015 inches (0.38 mm). In some examples, the tapered surface distal edge 1761 has an outer diameter of about 0.155 inches (3.94 mm).

At the apex 1764 of the blades 1763, the distal tip 1755 has an outer diameter of between about 0.148 inches and 0.152 inches. At the trough 1768 of the channels 1767, the distal tip 1755 has an outer diameter of between about 0.0118 inches and 0.0121 inches. Thus the difference in outer diameter from the trough 1768 to the apex 1764 is approximately 0.030 inches in this example. The distal tip 1755 has a tip length as shown in FIGS. 17A-F is 0.060 inches. In other examples the tip length is between about 0.025 and 0.125 inches; in another example the tip length is between 0.050 and 0.090 inches. The distal tip surface 1752 (which includes the surface of the blades) of the distal tip 1755 has a surface area of between about 0.0390 inches squared and 0.0370 inches squared. A male luer distal tip 1755 without blades 1763 and an outer diameter equal to the trough diameter has a surface area between about 0.0235 inches squared and 0.0215 inches squared. Thus, the blades 1763 and channels 1767 increase the surface area of the distal tip 1755 by about 68 percent. In some examples, increasing the distal tip surface 1752 can decrease the amount of antimicrobial that is removed from the distal tip surface 1752 when the connector is being inserted into an infusion device.

During insertion of the male luer 1741 into a female luer, portions of the distal tip 1755 may come in contact with the inside surface of the female luer. The apex 1764 of each blade 1763 may come in contact with the female luer surface, but the troughs 1768 of the channels 1767 will not come in contact with the female luer surface. Thus, in comparison to the tapered surface distal edge 1761, the blades 1763 have a relatively smaller contacting surface area near the end face 1704 of the distal tip 1755. This minimizes the amount of ingress of microbes that can be attributed to microbes being pushed into the body of the female luer by the blades 1763 compared to the tapered surface distal edge 1761 of the male luer 1741. Thus in some situations there is a greater probability of the microbes being located at the tapered surface distal edge 1761 compared to the end face 1704. This is desirable because the concentration of antimicrobial composition will be greater (it will be at a lethal concentration to kill microbes) at the tapered surface distal edge 1761 than the end face 1704.

Figure 17A:
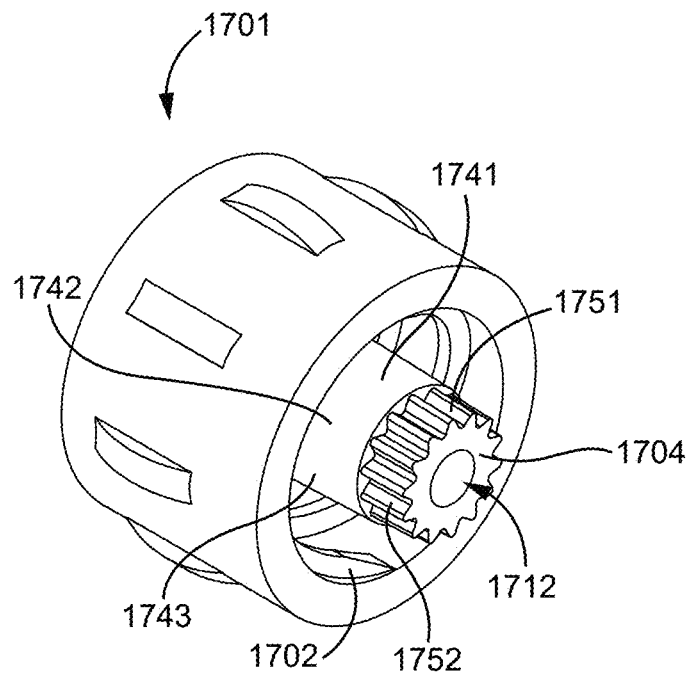
FIG. 17A is an isometric view of a male luer connector according to some examples.
Figure 17C:
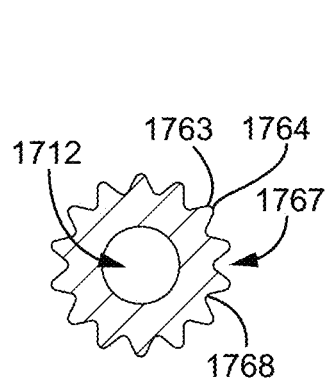
FIG. 17C is a cross-sectional view of the male luer connector of FIG. 17A along line C-C of FIG. 17B.
Figure 17B:
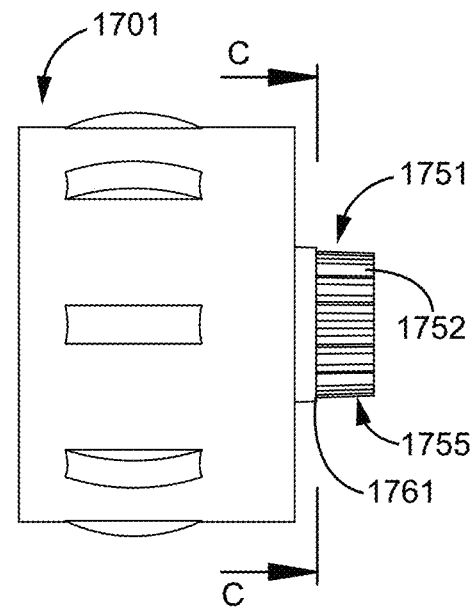
FIG. 17B is a side view of the male luer connector of FIG. 17A.
Figure 17D:
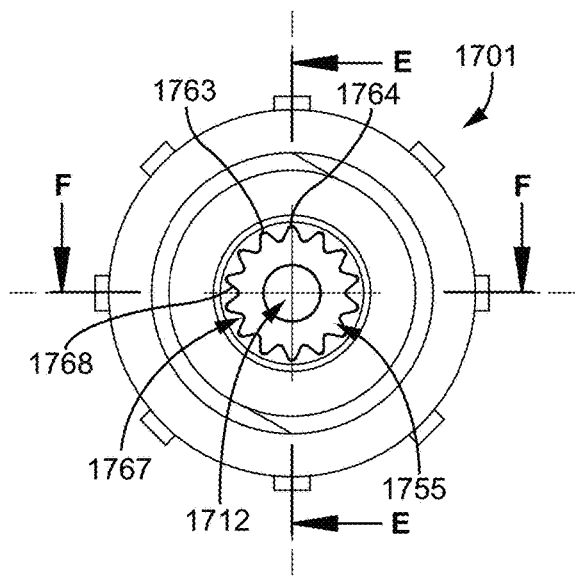
FIG. 17D is an end view of the male luer connector of FIG. 17A.
Figure 17E:
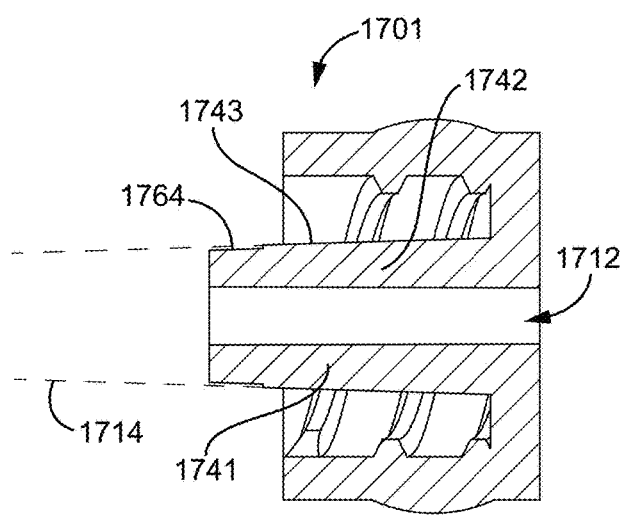
FIG. 17E is a cross-sectional view of the male luer connector of FIG. 17A along line E-E of FIG. 17D.
Figure 17F:
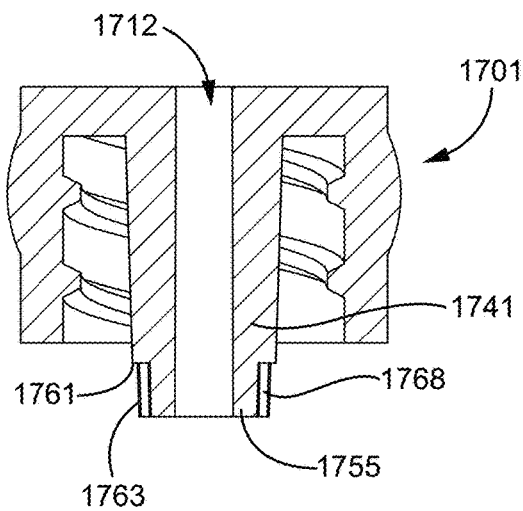
FIG. 17F is a cross-sectional view of the male luer connector of FIG. 17A along line F-F of FIG. 17D.

The channels 1767 affect confinement of microbes within the distal recess 1751 because the channels 1767 provide a restricted space in which microbes can be trapped between the distal tip surface 1752 and an inside surface of a female luer. The apex 1764 of the blades 1763 provide a maximum outer diameter of the distal tip 1755, and the troughs 1768 of the channels 1767 provide a minimum outer diameter of the distal tip 1755. Although some fluid flow between adjacent channels 1767 is possible when the male luer 1741 is coupled with a female luer, the blades 1763 provide a partial physical barrier. As seen in FIGS. 17D-F, the distal tip 1755 has an outer diameter that is smaller than the outer diameter of the tapered sealing member 1742 at the tapered surface distal edge 1761, and the outer diameter of the distal tip 1755 is smaller than the outer diameter of the distal taper line 1714 defined by the conical tapered sealing member 1742.

Male Luer Connector with Elongated Blades (FIGS. 18A-F)

Turning now to FIGS. 18A-F, a male luer connector 1801 includes a male luer 1841. The male luer 1841 comprises a tapered sealing member 1842. The tapered sealing member 1842 has a frustoconical shape that tapers from a larger outer diameter at the proximal portion of the tapered sealing member 1842 to a smaller outer diameter at the distal portion of the tapered sealing member near the tapered surface distal edge 1861. The tapered sealing member 1842 has a tapered sealing surface 1843 that is configured to mate with a female luer to create a fluid tight fit. The male luer connector 1801 further includes threads 1802 that allow the male luer connector 1801 to couple with a female luer connector. A lumen 1812 runs through the male luer connector 1801.

The male luer 1841 includes a distal tip 1855 with an end face 1804. The distal tip 1855 of the male luer 1841 is recessed from the distal line of taper of the tapered sealing member 1842. A distal recess 1851 is formed by a recessed portion of the distal tip 1855. The distal tip surface 1852 of the distal tip 1855 defines an outer diameter that is smaller than the outer diameter of the extension of the tapered sealing surface 1843.

The male luer 1841 includes a tapered surface distal edge 1861 that defines a proximal edge of the distal tip 1855. In some examples, an antimicrobial agent is applied to the distal tip surface 1852 by coating, spraying, or dipping the distal tip 1855 with an antimicrobial agent, although other methods of applying antimicrobial agent are contemplated and are within the scope of the technology. In some examples, antimicrobial agent is also applied to the tapered sealing surface 1843. An antimicrobial agent on the distal tip surface 1852 of the distal tip 1855 kills microbes within the distal recess 1851 between the surface of the female luer and the distal tip surface 1852. The distal recess 1851 is designed to confine the antimicrobial agent between the inner surface of a female luer and the distal tip surface 1852 so that microbes are exposed to a high antimicrobial concentration.

The male luer 1841 further includes multiple blades 1863 arrayed around the distal tip 1855 of the male luer 1841. Between the blades 1863 are a plurality of channels 1867. In the example of FIG. 18, the blades 1863 are elongated projections arranged around the axis of the tapered sealing member 1842, and the channels 1867 are elongated recesses disposed between the blades 1863 and running parallel to the lumen 1812. The blades 1863 and channels 1867 form alternating apexes 1864 and troughs 1868. The distal tip surface 1852 of the distal tip 1855 is defined by the blades 1863 and channels 1867. An antimicrobial agent on the distal tip surface 1852 can be stored within the volumes between the blades 1863.

During insertion of the male luer 1841 into a female luer, portions of the distal tip 1855 may come in contact with the inside surface of the female luer. The apex 1864 of each blade 1863 may come in contact with the female luer surface, but the troughs 1868 of the channels 1867 will not come in contact with the female luer surface. Thus, in comparison to the tapered surface distal edge 1861, the blades 1863 have a relatively smaller surface area near the end face 1804 of the distal tip 1855. This minimizes the amount of ingress of microbes that can be attributed to microbes being pushed into the body of the female luer by the male luer 1841.

Figure 18D:
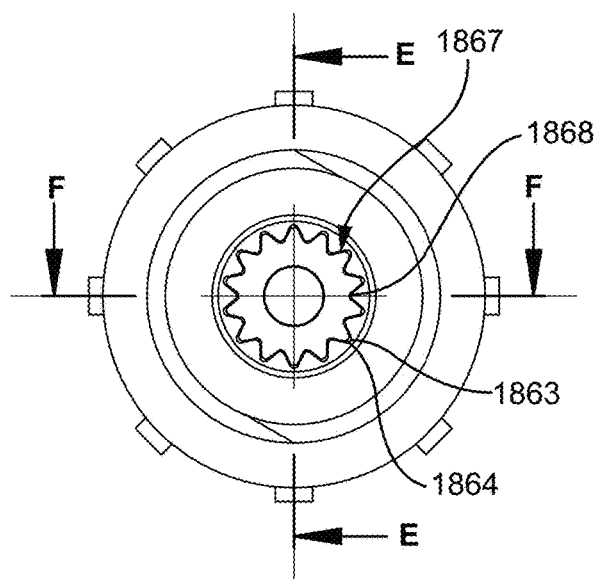
FIG. 18D is an end view of the male luer connector of FIG. 18A.
Figure 18E:
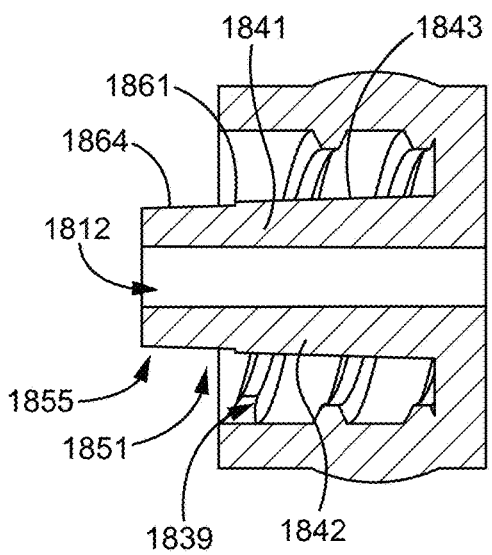
FIG. 18E is a cross-sectional view of the male luer connector of FIG. 18A along line E-E of FIG. 18D.
Figure 18F:
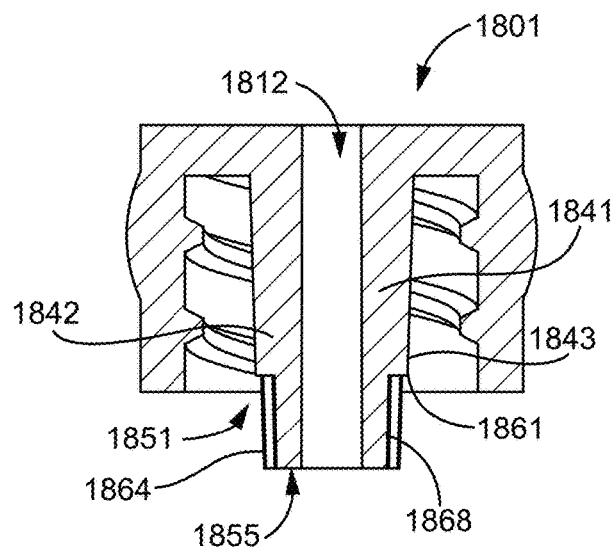
FIG. 18F is a cross-sectional view of the male luer connector of FIG. 18A along line F-F of FIG. 18D.

The channels 1867 affect confinement of microbes within the distal recess because the channels 1867 provide a restricted space in which microbes can be trapped between the distal tip surface 1852 and an inside surface of a female luer. The apex 1864 of the blades 1863 provide a maximum outer diameter of the distal tip 1855, and the troughs 1868 of the channels 1867 provide a minimum outer diameter of the distal tip 1855. Although some fluid flow between adjacent channels 1867 is possible when the male luer 1841 is coupled with a female luer, the blades 1863 provide a partial physical barrier. As seen in FIGS. 18D and 18E, the distal tip 1855 has an outer diameter that is smaller than the outer diameter of the tapered sealing member 1842 at the tapered surface distal edge 1861, and the outer diameter of the distal tip 1855 is smaller than the outer diameter of a distal taper line defined by the conical tapered sealing member 1842.

The distal tip 1855 has fourteen elongated blades 1863 that extend into the threaded cavity 1839 of the male luer connector 1801. The male luer 1841 of FIG. 18 has a shorter tapered sealing surface 1843 than the male luer 1741 of FIG. 17; however, the distal recess 1851 is longer and the distal tip surface 1852 of the distal tip 1855 has a greater surface area than the example of FIG. 17. In some examples, the length of the distal tip 1855 as measured perpendicular to the outer diameter of the distal tip 1855 is between about 0.025 and 0.125 inches (0.64-3.18 mm).

Male Luer Connector with Six Blades (FIGS. 19A-F)

Turning now to FIGS. 19A-F, a male luer connector 1901 includes a male luer 1941. The male luer 1941 comprises a tapered sealing member 1942. The tapered sealing member 1942 has a frustoconical shape that tapers from a larger outer diameter at the proximal portion of the tapered sealing member 1942 to a smaller outer diameter at the distal portion of the tapered sealing member near the tapered surface distal edge 1961. The tapered sealing member 1942 has a tapered sealing surface 1943 that is configured to mate with a female luer to create a fluid tight fit. The male luer connector 1901 further includes threads 1902 that allow the male luer connector 1901 to couple with a female luer connector. A lumen 1912 runs through the male luer connector 1901.

The male luer 1941 includes a distal tip 1955 with an end face 1904. The distal tip 1955 of the male luer 1941 is recessed from the distal line of taper of the tapered sealing member 1942. A distal recess 1951 is formed by a recessed portion of the distal tip 1955. The distal tip surface 1952 of the distal tip 1955 defines an outer diameter that is smaller than the outer diameter of the extension of the tapered sealing surface 1943.

The male luer 1941 includes a tapered surface distal edge 1961 that defines a proximal edge of the distal tip 1955. In some examples, an antimicrobial agent is applied to the distal tip surface 1952 by coating, spraying, or dipping the distal tip 1955 with an antimicrobial agent, although other methods of applying antimicrobial agent are contemplated and are within the scope of the technology. In some examples, antimicrobial agent is also applied to the tapered sealing surface 1943. An antimicrobial agent on the distal tip surface 1952 of the distal tip 1955 kills microbes within the distal recess 1951 between the surface of the female luer and the distal tip surface 1952. The distal recess 1951 is designed to confine the antimicrobial agent between the inner surface of a female luer and the distal tip surface 1952 so that microbes are exposed to a high antimicrobial concentration.

The male luer 1941 further includes multiple blades 1963 arrayed around the distal tip 1955 of the male luer 1941. Between the blades 1963 are a plurality of channels 1967. In the example of FIG. 19, the blades 1963 are elongated projections arranged around the axis of the tapered sealing member 1942, and the channels 1967 are elongated recesses disposed between the blades 1963 and running parallel to the lumen 1912. The blades 1963 and channels 1967 form alternating apexes 1964 and troughs 1968. The distal tip surface 1952 of the distal tip 1955 is defined by the blades 1963 and channels 1967. An antimicrobial agent on the distal tip surface 1952 can be stored within the volumes between the blades 1963.

During insertion of the male luer 1941 into a female luer, portions of the distal tip 1955 may come in contact with the inside surface of the female luer. The apex 1964 of each blade 1963 may come in contact with the female luer surface, but the troughs 1968 of the channels 1967 will not come in contact with the female luer surface. Thus, in comparison to the tapered surface distal edge 1961, the blades 1963 have a relatively smaller surface area near the end face 1904 of the distal tip 1955. This minimizes the amount of ingress of microbes that can be attributed to microbes being pushed into the body of the female luer by the male luer 1941.

Figure 19A:
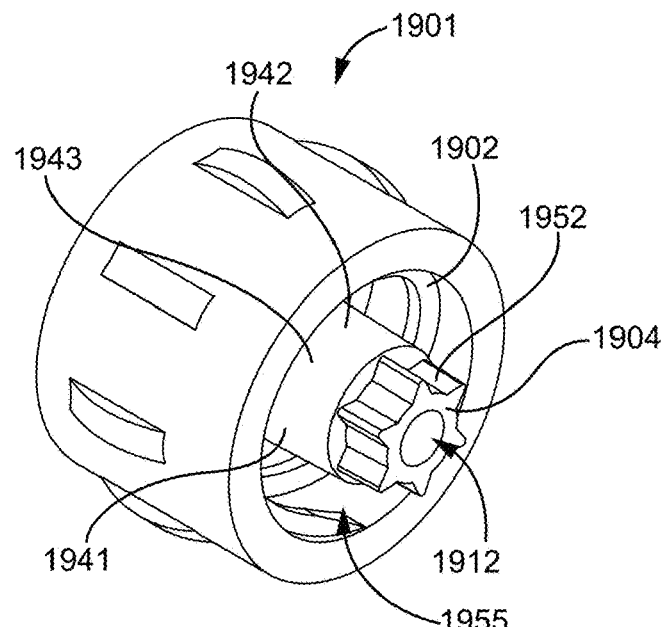
FIG. 19A is an isometric view of a male luer connector according to some examples.
Figure 19B:
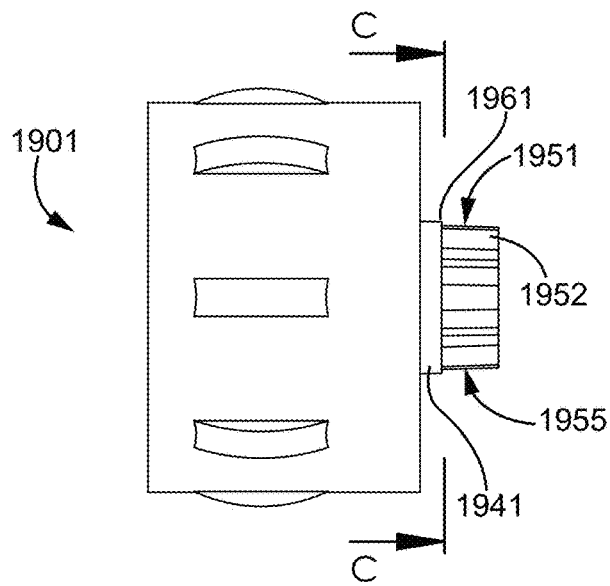
FIG. 19B is a side view of the male luer connector of FIG. 19A.
Figure 19C:
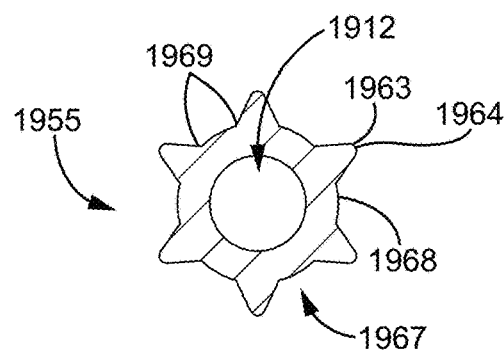
FIG. 19C is a cross-sectional view of the male luer connector of FIG. 19A along line C-C of FIG. 19B.
Figure 19D:
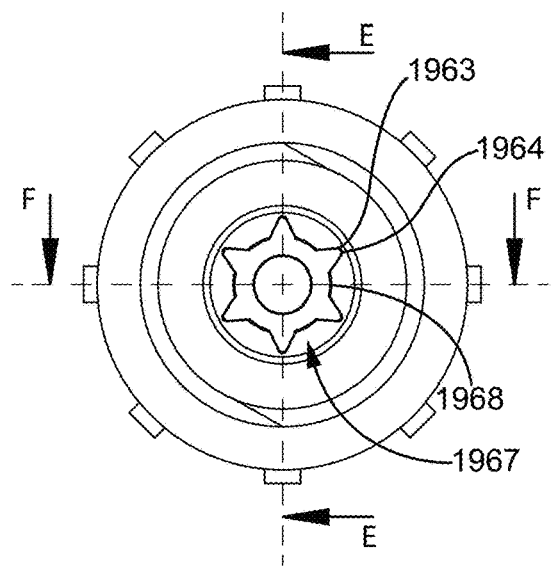
FIG. 19D is an end view of the male luer connector of FIG. 19A.
Figure 19E:
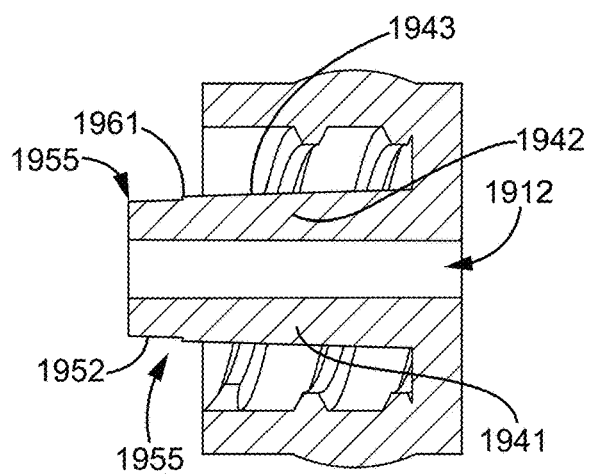
FIG. 19E is a cross-sectional view of the male luer connector of FIG. 19A along line E-E of FIG. 19D.
Figure 19F:
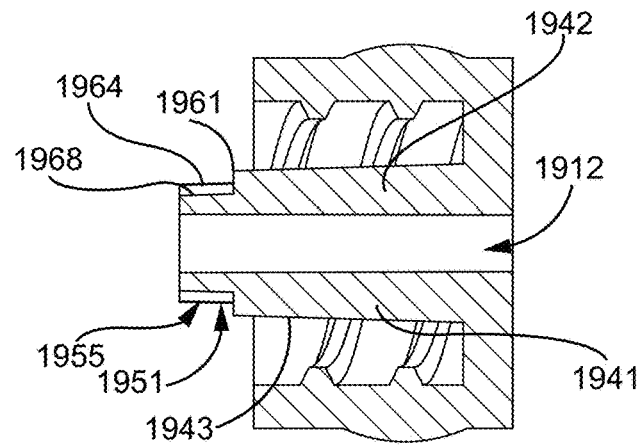
FIG. 19F is a cross-sectional view of the male luer connector of FIG. 19A along line F-F of FIG. 19D.

The channels 1967 affect confinement of microbes within the distal recess because the channels 1967 provide a restricted space in which microbes can be trapped between the distal tip surface 1952 and an inside surface of a female luer. The apex 1964 of the blades 1963 provide a maximum outer diameter of the distal tip 1955, and the troughs 1968 of the channels 1967 provide a minimum outer diameter of the distal tip 1955. Although some fluid flow between adjacent channels 1967 is possible when the male luer 1941 is coupled with a female luer, the blades 1963 provide a partial physical barrier. As seen in FIGS. 19D and 19E, the distal tip 1955 has an outer diameter that is smaller than the outer diameter of the tapered sealing member 1942 at the tapered surface distal edge 1961, and the outer diameter of the distal tip 1955 is smaller than the outer diameter of a distal taper line defined by the conical tapered sealing member 1942.

The distal tip 1955 of the male luer 1941 has six blades 1963 defining six channels 1967 with troughs 1968. In the example of FIG. 19C, the troughs 1968 are curved slightly outward, creating distinct creases 1969 at the base of the blades 1963.

Male Luer Connector with Blades and Rounded Distal Tip (FIGS. 20A-G)

Turning now to FIGS. 20A-G, a male luer connector 2001 includes a male luer 2041. The male luer 2041 comprises a tapered sealing member 2042. The tapered sealing member 2042 has a frustoconical shape that tapers from a larger outer diameter at the proximal portion of the tapered sealing member 2042 to a smaller outer diameter at the distal portion of the tapered sealing member near the tapered surface distal edge 2061. The tapered sealing member 2042 has a tapered sealing surface 2043 that is configured to mate with a female luer to create a fluid tight fit. The male luer connector 2001 further includes threads 2002 that allow the male luer connector 2001 to couple with a female luer connector. A lumen 2012 runs through the male luer connector 2001.

The male luer 2041 includes a distal tip 2055 with an end face 2004. The distal tip 2055 of the male luer 2041 is recessed from the distal line of taper of the tapered sealing member 2042. A distal recess 2051 is formed by a recessed portion of the distal tip 2055. The distal tip surface 2052 of the distal tip 2055 defines an outer diameter that is smaller than the outer diameter of the extension of the tapered sealing surface 2043.

The male luer 2041 includes a tapered surface distal edge 2061 that defines a proximal edge of the distal tip 2055. In some examples, an antimicrobial agent is applied to the distal tip surface 2052 by coating, spraying, or dipping the distal tip 2055 with an antimicrobial agent, although other methods of applying antimicrobial agent are contemplated and are within the scope of the technology. In some examples, antimicrobial agent is also applied to the tapered sealing surface 2043. An antimicrobial agent on the distal tip surface 2052 of the distal tip 2055 kills microbes within the distal recess 2051 between the surface of the female luer and the distal tip surface 2052. The distal recess 2051 is designed to confine the antimicrobial agent between the inner surface of a female luer and the distal tip surface 2052 so that microbes are exposed to a high antimicrobial concentration.

The male luer 2041 further includes multiple blades 2063 arrayed around the distal tip 2055 of the male luer 2041. Between the blades 2063 are a plurality of channels 2067. In the example of FIG. 20, the blades 2063 are elongated projections arranged around the axis of the tapered sealing member 2042, and the channels 2067 are elongated recesses disposed between the blades 2063 and running parallel to the lumen 2012. The blades 2063 and channels 2067 form alternating apexes 2064 and troughs 2068. The distal tip surface 2052 of the distal tip 2055 is defined by the blades 2063 and channels 2067. An antimicrobial agent on the distal tip surface 2052 can be stored within the volumes between the blades 2063.

During insertion of the male luer 2041 into a female luer, portions of the distal tip 2055 may come in contact with the inside surface of the female luer. The apex 2064 of each blade 2063 may come in contact with the female luer surface, but the troughs 2068 of the channels 2067 will not come in contact with the female luer surface. Thus, in comparison to the tapered surface distal edge 2061, the blades 2063 have a relatively smaller surface area near the end face 2004 of the distal tip 2055. This minimizes the amount of ingress of microbes that can be attributed to microbes being pushed into the body of the female luer by the male luer 2041.

Figure 20E:
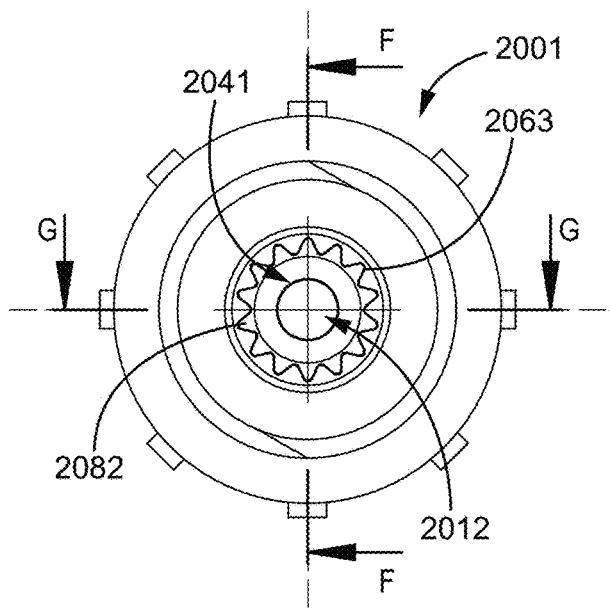
FIG. 20E is an end view of the male luer connector of FIG. 20A.
Figure 20F:
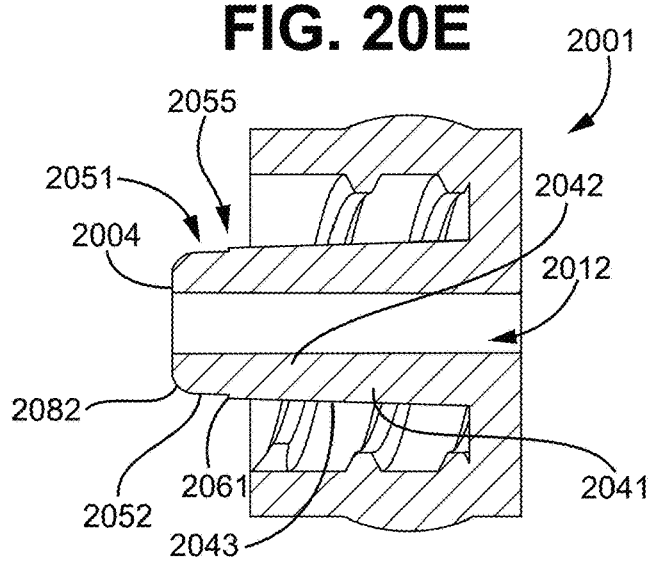
FIG. 20F is a cross-sectional view of the male luer connector of FIG. 20A along line F-F of FIG. 20E.
Figure 20G:
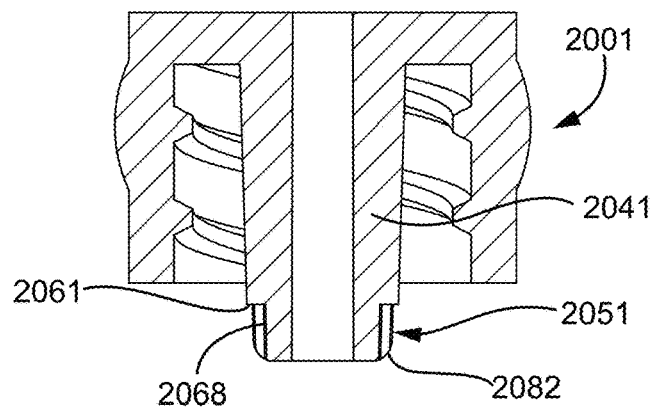
FIG. 20G is a cross-sectional view of the male luer connector of FIG. 20A along line G-G of FIG. 20E.

The channels 2067 affect confinement of microbes within the distal recess because the channels 2067 provide a restricted space in which microbes can be trapped between the distal tip surface 2052 and an inside surface of a female luer. The apex 2064 of the blades 2063 provide a maximum outer diameter of the distal tip 2055, and the troughs 2068 of the channels 2067 provide a minimum outer diameter of the distal tip 2055. Although some fluid flow between adjacent channels 2067 is possible when the male luer 2041 is coupled with a female luer, the blades 2063 provide a partial physical barrier. As seen in FIGS. 20E and 20F, the distal tip 2055 has an outer diameter that is smaller than the outer diameter of the tapered sealing member 2042 at the tapered surface distal edge 2061, and the outer diameter of the distal tip 2055 is smaller than the outer diameter of a distal taper line defined by the conical tapered sealing member 2042.

The distal tip 2055 has a plurality of blades 2063 separating a plurality of channels 2067. The blades 2063 have rounded blade tips 2082 that taper in width from the end face 1904 to the apex 2064 of the blades 2063. This structure makes the distal recess 2051 rounded at the boundary between the distal recess region and the bulk flow region when the male luer 2041 is coupled with a female luer.

Male Luer Connector with Enhanced Crevices (FIGS. 21A-F)

Turning now to FIGS. 21A-F, a male luer connector 2101 includes a male luer 2141. The male luer 2141 comprises a tapered sealing member 2142. The tapered sealing member 2142 has a frustoconical shape that tapers from a larger outer diameter at the proximal portion of the tapered sealing member 2142 to a smaller outer diameter at the distal portion of the tapered sealing member near the tapered surface distal edge 2161. The tapered sealing member 2142 has a tapered sealing surface 2143 that is configured to mate with a female luer to create a fluid tight fit. The male luer connector 2101 further includes threads 2102 that allow the male luer connector 2101 to couple with a female luer connector. A lumen 2112 runs through the male luer connector 2101.

The male luer 2141 includes a distal tip 2155 with an end face 2104. The distal tip 2155 of the male luer 2141 is recessed from the distal line of taper of the tapered sealing member 2142. A distal recess 2151 is formed by a recessed portion of the distal tip 2155. The distal tip surface 2152 of the distal tip 2155 defines an outer diameter that is smaller than the outer diameter of the extension of the tapered sealing surface 2143.

The male luer 2141 includes a tapered surface distal edge 2161 that defines a proximal edge of the distal tip 2155. In some examples, an antimicrobial agent is applied to the distal tip surface 2152 by coating, spraying, or dipping the distal tip 2155 with an antimicrobial agent, although other methods of applying antimicrobial agent are contemplated and are within the scope of the technology. In some examples, antimicrobial agent is also applied to the tapered sealing surface 2143. An antimicrobial agent on the distal tip surface 2152 of the distal tip 2155 kills microbes within the distal recess 2151 between the surface of the female luer and the distal tip surface 2152. The distal recess 2151 is designed to confine the antimicrobial agent between the inner surface of a female luer and the distal tip surface 2152 so that microbes are exposed to a high antimicrobial concentration.

The male luer 2141 further includes multiple blades 2163 arrayed around the distal tip 2155 of the male luer 2141. Between the blades 2163 are a plurality of channels 2167. In the example of FIG. 21, the blades 2163 are elongated projections arranged around the axis of the tapered sealing member 2142, and the channels 2167 are elongated recesses disposed between the blades 2163 and running parallel to the lumen 2112. The blades 2163 and channels 2167 form alternating apexes 2164 and troughs 2168. The distal tip surface 2152 of the distal tip 2155 is defined by the blades 2163 and channels 2167. An antimicrobial agent on the distal tip surface 2152 can be stored within the volumes between the blades 2163.

During insertion of the male luer 2141 into a female luer, portions of the distal tip 2155 may come in contact with the inside surface of the female luer. The apex 2164 of each blade 2163 may come in contact with the female luer surface, but the troughs 2168 of the channels 2167 will not come in contact with the female luer surface. Thus, in comparison to the tapered surface distal edge 2161, the blades 2163 have a relatively smaller surface area near the end face 2104 of the distal tip 2155. This minimizes the amount of ingress of microbes that can be attributed to microbes being pushed into the body of the female luer by the male luer 2141.

Figure 21A:
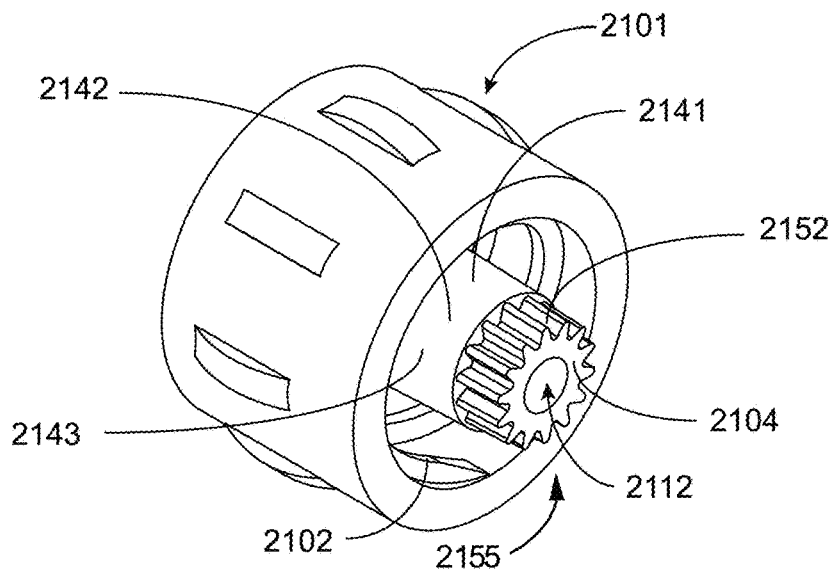
FIG. 21A is an isometric view of a male luer connector according to some examples.
Figure 21B:
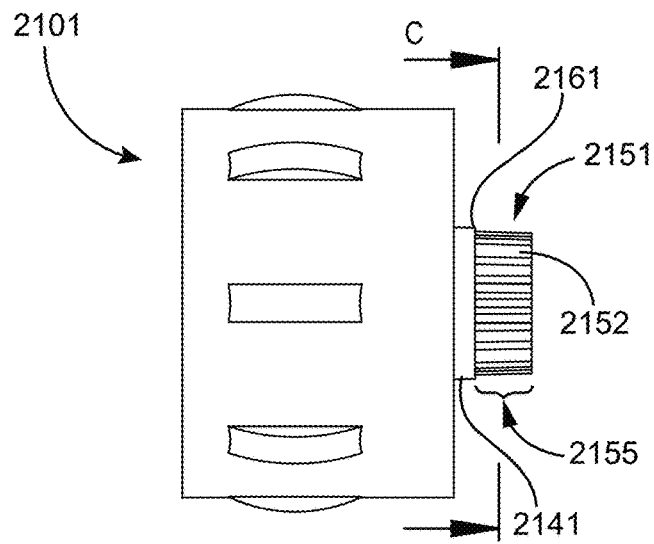
FIG. 21B is a side view of the male luer connector of FIG. 21A.
Figure 21C:
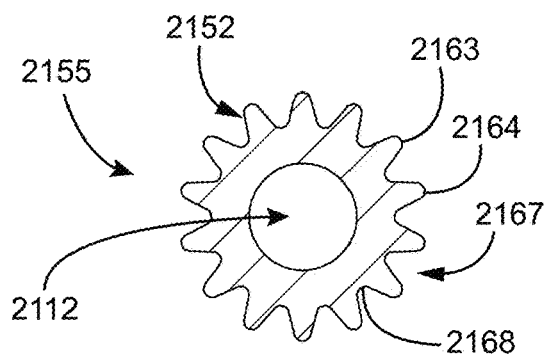
FIG. 21C is a cross-sectional view of the male luer connector of FIG. 21A along line C-C of FIG. 21B.
Figure 21D:
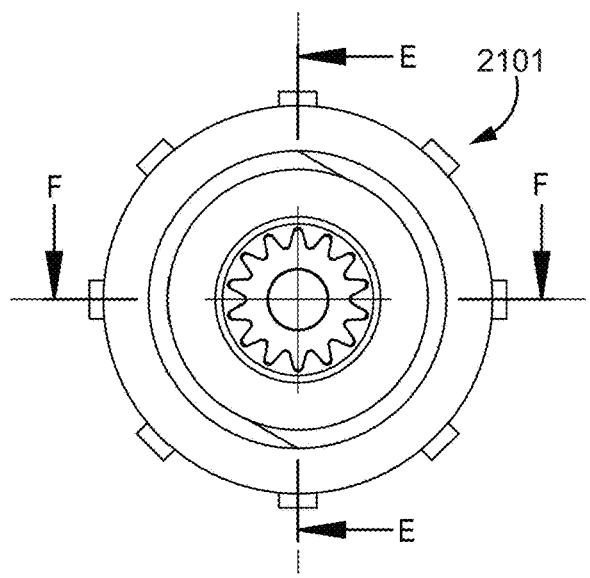
FIG. 21D is an end view of the male luer connector of FIG. 21A.
Figure 21E:
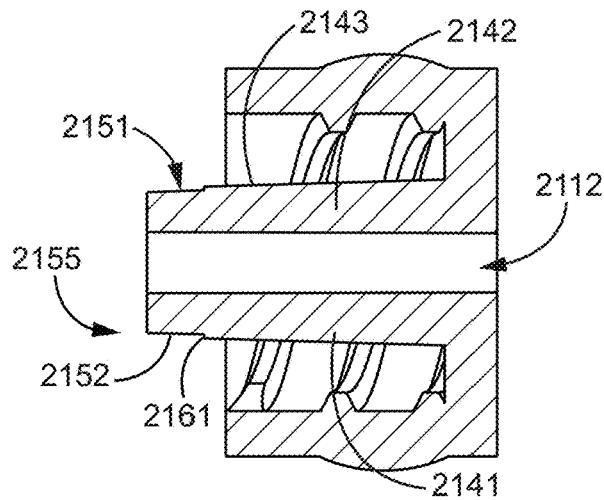
FIG. 21E is a cross-sectional view of the male luer connector of FIG. 21A along line E-E of FIG. 21D.
Figure 21F:
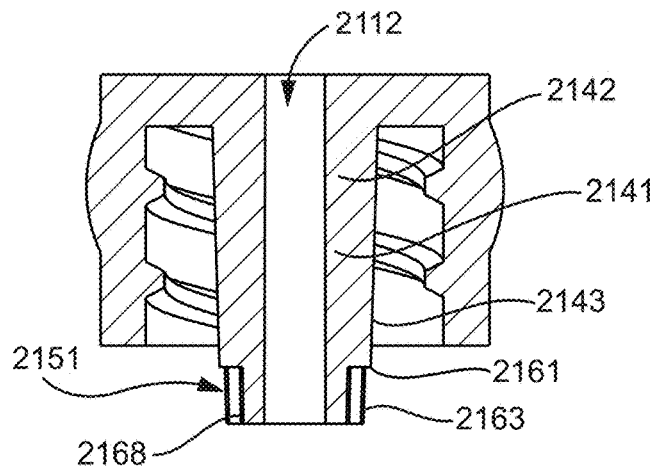
FIG. 21F is a cross-sectional view of the male luer connector of FIG. 21A along line F-F of FIG. 21D.

The channels 2167 affect confinement of microbes within the distal recess because the channels 2167 provide a restricted space in which microbes can be trapped between the distal tip surface 2152 and an inside surface of a female luer. The apex 2164 of the blades 2163 provide a maximum outer diameter of the distal tip 2155, and the troughs 2168 of the channels 2167 provide a minimum outer diameter of the distal tip 2155. Although some fluid flow between adjacent channels 2167 is possible when the male luer 2141 is coupled with a female luer, the blades 2163 provide a partial physical barrier. As seen in FIGS. 21D and 21E, the distal tip 2155 has an outer diameter that is smaller than the outer diameter of the tapered sealing member 2142 at the tapered surface distal edge 2161, and the outer diameter of the distal tip 2155 is smaller than the outer diameter of a distal taper line defined by the conical tapered sealing member 2142.

The distal tip 2155 has a plurality of blades 2163 that separate a plurality of channels 2167. This example shows a large difference in height from the apex 2164 to the trough 2168. This in turn increases the surface area on which an antimicrobial agent can be stored. Furthermore, the depth of the channels 2167 allows an increased load of antimicrobial agent to be stored at the distal tip 2155.

Male Luer Connector with Irregular Blade Heights (FIGS. 22A-F)

Turning now to FIGS. 22A-F, a male luer connector 2201 includes a male luer 2241. The male luer 2241 comprises a tapered sealing member 2242. The tapered sealing member 2242 has a frustoconical shape that tapers from a larger outer diameter at the proximal portion of the tapered sealing member 2242 to a smaller outer diameter at the distal portion of the tapered sealing member near the tapered surface distal edge 2261. The tapered sealing member 2242 has a tapered sealing surface 2243 that is configured to mate with a female luer to create a fluid tight fit. The male luer connector 2201 further includes threads 2202 that allow the male luer connector 2201 to couple with a female luer connector. A lumen 2212 runs through the male luer connector 2201.

The male luer 2241 includes a distal tip 2255 with an end face 2204. The distal tip 2255 of the male luer 2241 is recessed from the distal line of taper of the tapered sealing member 2242. A distal recess 2251 is formed by a recessed portion of the distal tip 2255. The distal tip surface 2252 of the distal tip 2255 defines an outer diameter that is smaller than the outer diameter of the extension of the tapered sealing surface 2243.

The male luer 2241 includes a tapered surface distal edge 2261 that defines a proximal edge of the distal tip 2255. In some examples, an antimicrobial agent is applied to the distal tip surface 2252 by coating, spraying, or dipping the distal tip 2255 with an antimicrobial agent, although other methods of applying antimicrobial agent are contemplated and are within the scope of the technology. In some examples, antimicrobial agent is also applied to the tapered sealing surface 2243. An antimicrobial agent on the distal tip surface 2252 of the distal tip 2255 kills microbes within the distal recess 2251 between the surface of the female luer and the distal tip surface 2252. The distal recess 2251 is designed to confine the antimicrobial agent between the inner surface of a female luer and the distal tip surface 2252 so that microbes are exposed to a high antimicrobial concentration.

The male luer 2241 further includes multiple blades 2263 arrayed around the distal tip 2255 of the male luer 2241. Between the blades 2263 are a plurality of channels 2267. In the example of FIG. 22, the blades 2263 are elongated projections arranged around the axis of the tapered sealing member 2242, and the channels 2267 are elongated recesses disposed between the blades 2263 and running parallel to the lumen 2212. The blades 2263 and channels 2267 form alternating apexes 2264 and troughs 2268. The distal tip surface 2252 of the distal tip 2255 is defined by the blades 2263 and channels 2267. An antimicrobial agent on the distal tip surface 2252 can be stored within the volumes between the blades 2263.

During insertion of the male luer 2241 into a female luer, portions of the distal tip 2255 may come in contact with the inside surface of the female luer. The apex 2264 of each high blade 2265 may come in contact with the female luer surface, but the troughs 2268 of the channels 2267 and low blades 2266 will not come in contact with the female luer surface. Thus, in comparison to the tapered surface distal edge 2261, the high blades 2265 have a relatively smaller surface area near the end face 2204 of the distal tip 2255. This minimizes the amount of ingress of microbes that can be attributed to microbes being pushed into the body of the female luer by the male luer 2241.

Figure 22A:
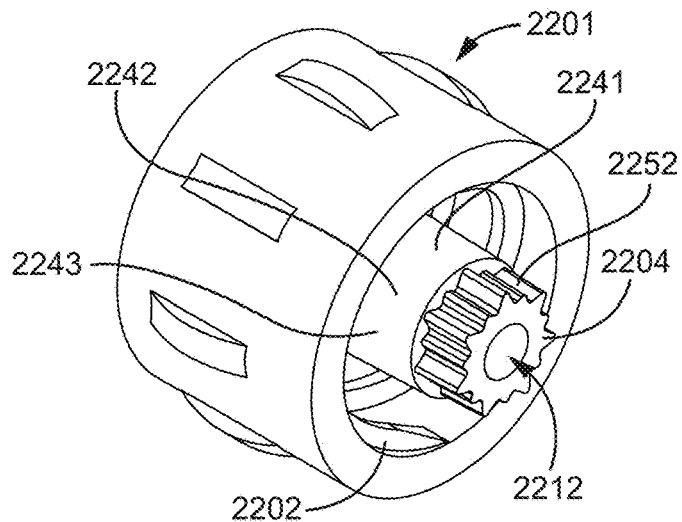
FIG. 22A is an isometric view of a male luer connector according to some examples.
Figure 22B:
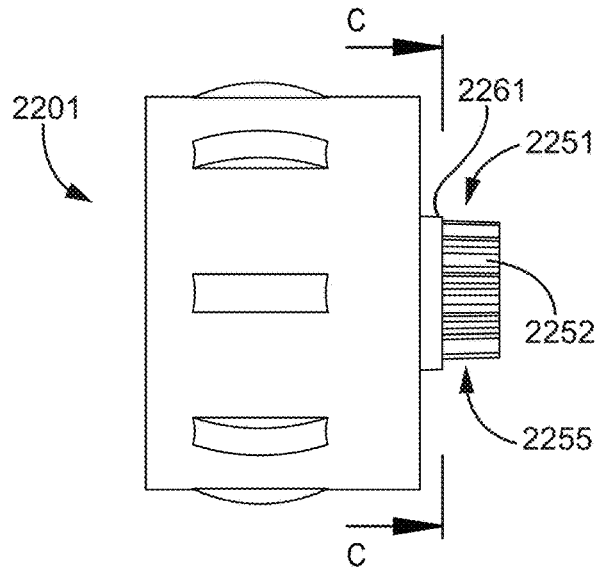
FIG. 22B is a side view of the male luer connector of FIG. 22A.
Figure 22C:
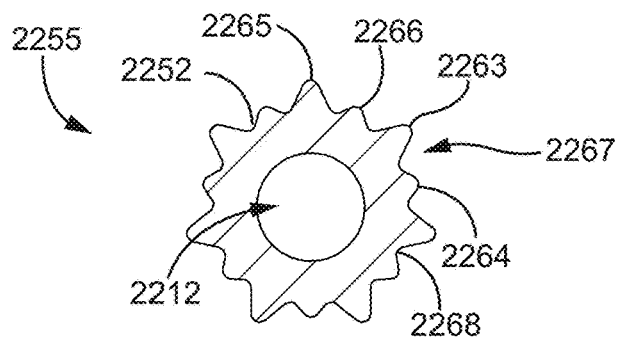
FIG. 22C is a cross-sectional view of the male luer connector of FIG. 22A along line C-C of FIG. 22B.
Figure 22D:
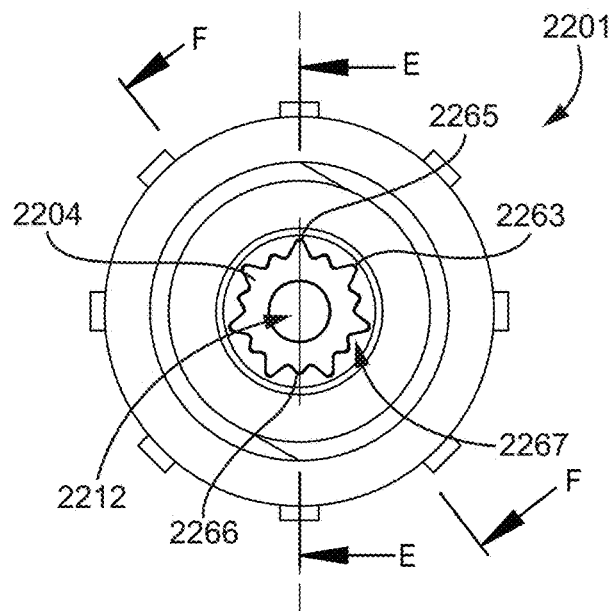
FIG. 22D is an end view of the male luer connector of FIG. 22A.
Figure 22E:
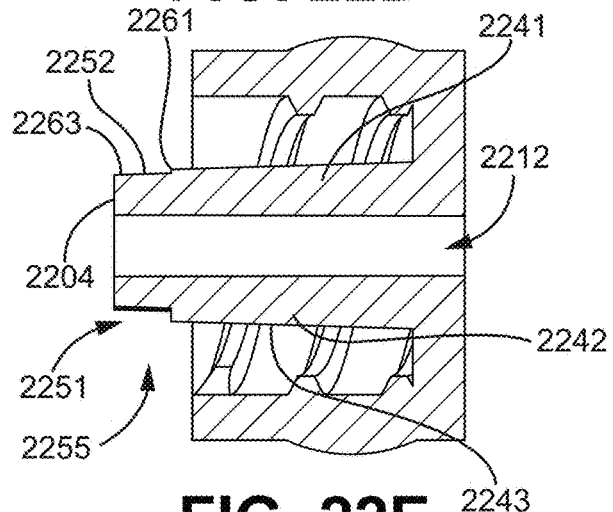
FIG. 22E is a cross-sectional view of the male luer connector of FIG. 22A along line E-E of FIG. 22D.
Figure 22F:
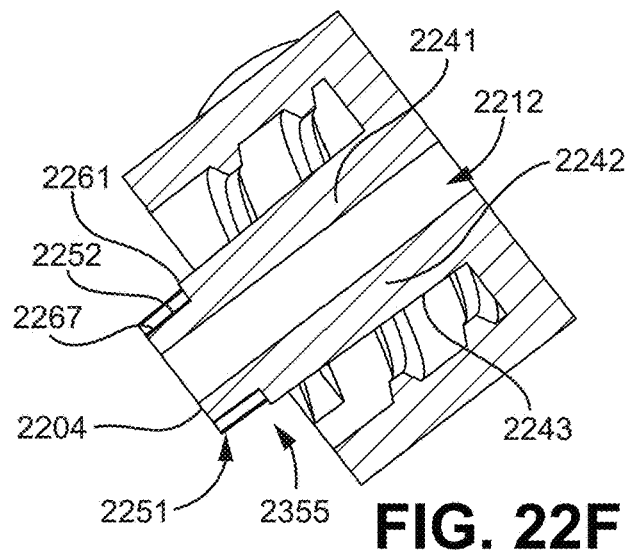
FIG. 22F is a cross-sectional view of the male luer connector of FIG. 22A along line F-F of FIG. 22D.

The channels 2267 affect confinement of microbes within the distal recess because the channels 2267 provide a restricted space in which microbes can be trapped between the distal tip surface 2252 and an inside surface of a female luer. The apex 2264 of the blades 2263 provide a maximum outer diameter of the distal tip 2255, and the troughs 2268 of the channels 2267 provide a minimum outer diameter of the distal tip 2255. Although some fluid flow between adjacent channels 2267 is possible when the male luer 2241 is coupled with a female luer, the blades 2263 provide a partial physical barrier. As seen in FIGS. 22D and 22E, the distal tip 2255 has an outer diameter that is smaller than the outer diameter of the tapered sealing member 2242 at the tapered surface distal edge 2261, and the outer diameter of the distal tip 2255 is smaller than the outer diameter of a distal taper line defined by the conical tapered sealing member 2242.

The distal tip 2255 has a plurality of blades 2263 that separate a plurality of channels 2267. In this example, the distal tip 2255 includes high blades 2265 and low blades 2266. The high blades 2265 have a greater outer diameter than the outer diameter of the low blades 2266. In this example, the troughs 2268 of the channels 2267 each have the same outer diameter. As can be seen in FIG. 22D, in this example, each high blade 2265 is 180° opposite a low blade 2266. As seen in FIG. 22E, the male luer 2241 has a tapered surface distal edge 2261, and the apex of a blade 2263 is inside the line of taper such that the outer diameter of the blade 2263 is less than the outer diameter of the tapered surface distal edge 2261.

Male Luer Connector with Irregular Blade Heights (FIGS. 23A-G)

Turning now to FIGS. 23A-G, a male luer connector 2301 includes a male luer 2341. The male luer 2341 comprises a tapered sealing member 2342. The tapered sealing member 2342 has a frustoconical shape that tapers from a larger outer diameter at the proximal portion of the tapered sealing member 2342 to a smaller outer diameter at the distal portion of the tapered sealing member near the tapered surface distal edge 2361. The tapered sealing member 2342 has a tapered sealing surface 2343 that is configured to mate with a female luer to create a fluid tight fit. The male luer connector 2301 further includes threads 2302 that allow the male luer connector 2301 to couple with a female luer connector. A lumen 2312 runs through the male luer connector 2301.

The male luer 2341 includes a distal tip 2355 with an end face 2304. The distal tip 2355 of the male luer 2341 is recessed from the distal line of taper of the tapered sealing member 2342. A distal recess 2351 is formed by a recessed portion of the distal tip 2355. The distal tip surface 2352 of the distal tip 2355 defines an outer diameter that is smaller than the outer diameter of the extension of the tapered sealing surface 2343.

The male luer 2341 includes a tapered surface distal edge 2361 that defines a proximal edge of the distal tip 2355. In some examples, an antimicrobial agent is applied to the distal tip surface 2352 by coating, spraying, or dipping the distal tip 2355 with an antimicrobial agent, although other methods of applying antimicrobial agent are contemplated and are within the scope of the technology. In some examples, antimicrobial agent is also applied to the tapered sealing surface 2343. An antimicrobial agent on the distal tip surface 2352 of the distal tip 2355 kills microbes within the distal recess 2351 between the surface of the female luer and the distal tip surface 2352. The distal recess 2351 is designed to confine the antimicrobial agent between the inner surface of a female luer and the distal tip surface 2352 so that microbes are exposed to a high antimicrobial concentration.

The male luer 2341 further includes multiple blades 2363 arrayed around the distal tip 2355 of the male luer 2341. Between the blades 2363 are a plurality of channels 2367. In the example of FIG. 23, the blades 2363 are elongated projections arranged around the axis of the tapered sealing member 2342, and the channels 2367 are elongated recesses disposed between the blades 2363 and running parallel to the lumen 2312. The blades 2363 and channels 2367 form alternating apexes 2364 and troughs 2368. The distal tip surface 2352 of the distal tip 2355 is defined by the blades 2363 and channels 2367. An antimicrobial agent on the distal tip surface 2352 can be stored within the volumes between the blades 2363.

Figure 23A:
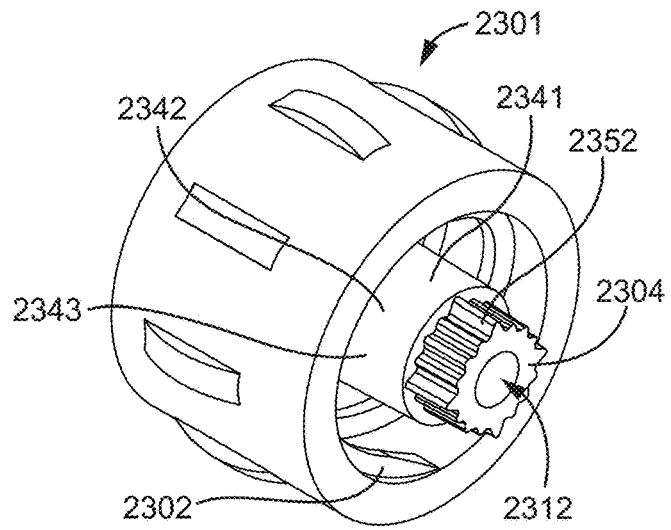
FIG. 23A is an isometric view of a male luer connector according to some examples.
Figure 23B:
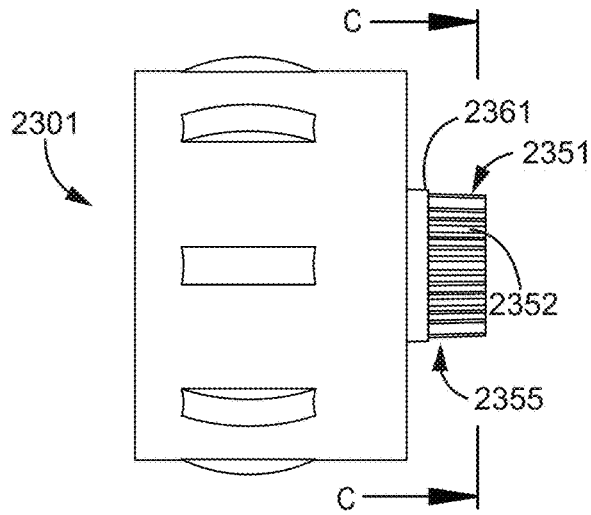
FIG. 23B is a side view of the male luer connector of FIG. 23A.
Figure 23C:
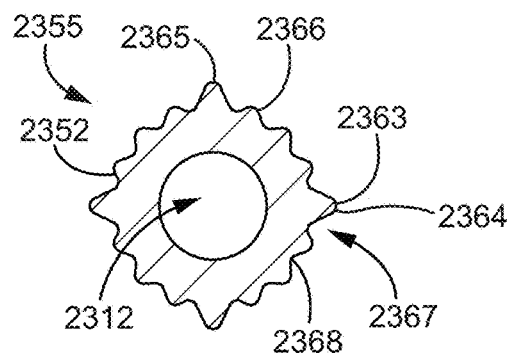
FIG. 23C is a cross-sectional view of the male luer connector of FIG. 23A along line C-C of FIG. 23B.
Figure 23D:
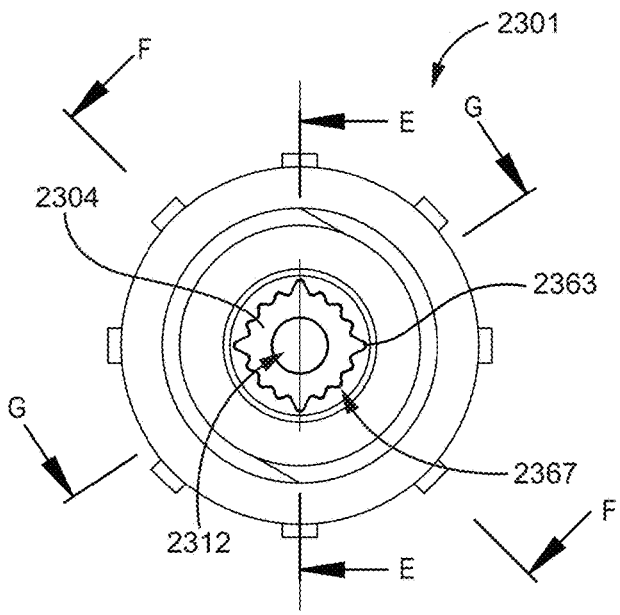
FIG. 23D is an end view of the male luer connector of FIG. 23A.
Figure 23E:
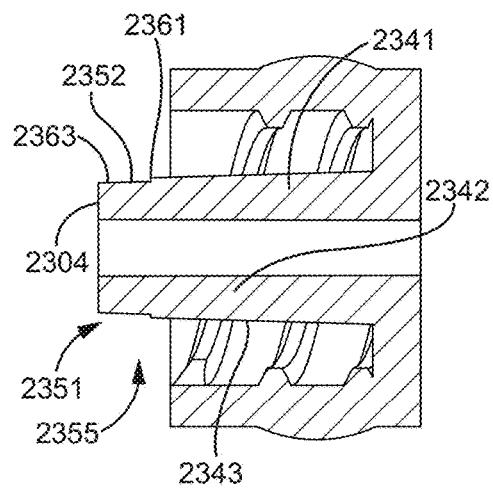
FIG. 23E is a cross-sectional view of the male luer connector of FIG. 23A along line E-E of FIG. 23D.
Figure 23F:
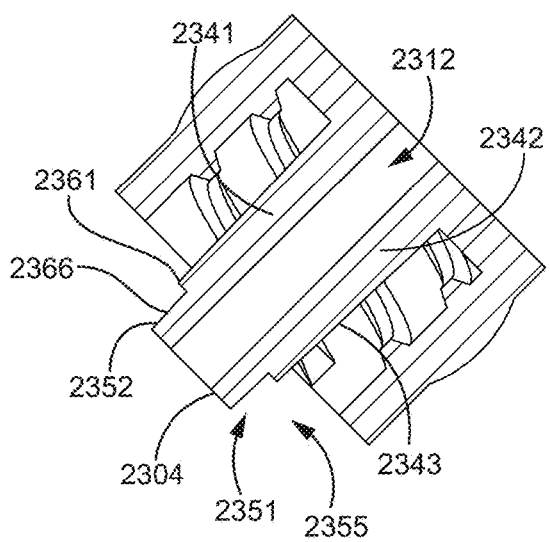
FIG. 23F is a cross-sectional view of the male luer connector of FIG. 23A along line F-F of FIG. 23D.
Figure 23G:
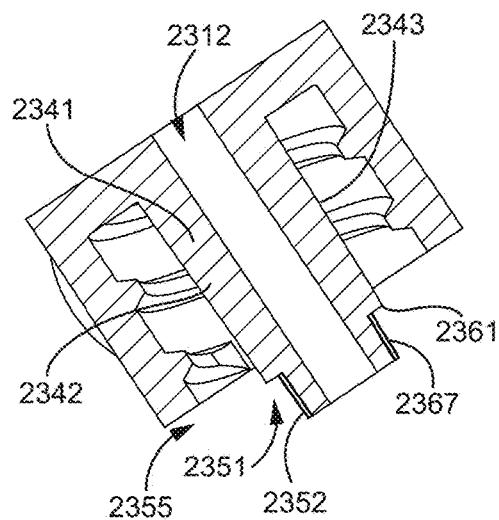
FIG. 23G is a cross-sectional view of the male luer connector of FIG. 23A along line G-G of FIG. 23D.

The distal tip 2355 has a plurality of blades 2363 that separate a plurality of channels 2367. In this example, the distal tip 2355 includes high blades 2365 and low blades 2366. The high blades 2365 have a greater outer diameter than the outer diameter of the low blades 2366. As seen in FIG. 23E, the male luer 2341 has a tapered surface distal edge 2361, and the apex 2364 of blade 2363 is inside the line of taper such that the outer diameter of the blade 2363 is less than the outer diameter of the tapered surface distal edge 2361.

During insertion of the male luer 2341 into a female luer, portions of the distal tip 2355 may come in contact with the inside surface of the female luer. The apex 2364 of each high blade 2365 may come in contact with the female luer surface, but the troughs 2368 of the channels 2367 and low blades 2366 will not come in contact with the female luer surface. Thus, in comparison to the tapered surface distal edge 2361, the high blades 2365 have a relatively smaller surface area near the end face 2304 of the distal tip 2355. This minimizes the amount of ingress of microbes that can be attributed to microbes being pushed into the body of the female luer by the male luer 2341.

The channels 2367 affect confinement of microbes within the distal recess because the channels 2367 provide a restricted space in which microbes can be trapped between the distal tip surface 2352 and an inside surface of a female luer. The apex 2364 of the blades 2363 provide a maximum outer diameter of the distal tip 2355, and the troughs 2368 of the channels 2367 provide a minimum outer diameter of the distal tip 2355. Although some fluid flow between adjacent channels 2367 is possible when the male luer 2341 is coupled with a female luer, the blades 2363 provide a partial physical barrier. As seen in FIGS. 23D and 23E, the distal tip 2355 has an outer diameter that is smaller than the outer diameter of the tapered sealing member 2342 at the tapered surface distal edge 2361, and the outer diameter of the distal tip 2355 is smaller than the outer diameter of a distal taper line defined by the conical tapered sealing member 2342.

Male Luer Connector with Tapered Blades and Channels (FIGS. 24A-F)

Turning now to FIGS. 24A-F, a male luer connector 2401 includes a male luer 2441. The male luer 2441 comprises a tapered sealing member 2442. The tapered sealing member 2442 has a frustoconical shape that tapers from a larger outer diameter at the proximal portion of the tapered sealing member 2442 to a smaller outer diameter at the distal portion of the tapered sealing member near the tapered surface distal edge 2461. The tapered sealing member 2442 has a tapered sealing surface 2443 that is configured to mate with a female luer to create a fluid tight fit. The male luer connector 2401 further includes threads 2402 that allow the male luer connector 2401 to couple with a female luer connector. A lumen 2412 runs through the male luer connector 2401.

The male luer 2441 includes a distal tip 2455 with an end face 2404. The distal tip 2455 of the male luer 2441 is recessed from the distal line of taper of the tapered sealing member 2442. A distal recess 2451 is formed by a recessed portion of the distal tip 2455. The distal tip surface 2452 of the distal tip 2455 defines an outer diameter that is smaller than the outer diameter of the extension of the tapered sealing surface 2443.

The male luer 2441 includes a tapered surface distal edge 2461 that defines a proximal edge of the distal tip 2455. In some examples, an antimicrobial agent is applied to the distal tip surface 2452 by coating, spraying, or dipping the distal tip 2455 with an antimicrobial agent, although other methods of applying antimicrobial agent are contemplated and are within the scope of the technology. In some examples, antimicrobial agent is also applied to the tapered sealing surface 2443. An antimicrobial agent on the distal tip surface 2452 of the distal tip 2455 kills microbes within the distal recess 2451 between the surface of the female luer and the distal tip surface 2452. The distal recess 2451 is designed to confine the antimicrobial agent between the inner surface of a female luer and the distal tip surface 2452 so that microbes are exposed to a high antimicrobial concentration.

The male luer 2441 further includes multiple blades 2463 arrayed around the distal tip 2455 of the male luer 2441. Between the blades 2463 are a plurality of channels 2467. In the example of FIG. 24, the blades 2463 are elongated projections arranged around the axis of the tapered sealing member 2442, and the channels 2467 are elongated recesses disposed between the blades 2463 and running parallel to the lumen 2412. The blades 2463 and channels 2467 form alternating apexes 2464 and troughs 2468. The distal tip surface 2452 of the distal tip 2455 is defined by the blades 2463 and channels 2467. An antimicrobial agent on the distal tip surface 2452 can be stored within the volumes between the blades 2463.

During insertion of the male luer 2441 into a female luer, portions of the distal tip 2455 may come in contact with the inside surface of the female luer. The apex 2464 of each blade 2463 may come in contact with the female luer surface, but the troughs 2468 of the channels 2467 will not come in contact with the female luer surface. Thus, in comparison to the tapered surface distal edge 2461, the blades 2463 have a relatively smaller surface area near the end face 2404 of the distal tip 2455. This minimizes the amount of ingress of microbes that can be attributed to microbes being pushed into the body of the female luer by the male luer 2441.

Figure 24F:
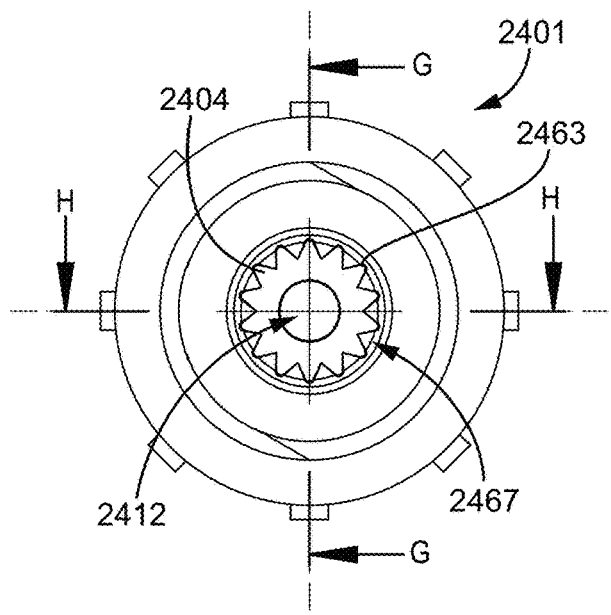
FIG. 24F is an end view of the male luer connector of FIG. 24A according to some examples.
Figure 24G:
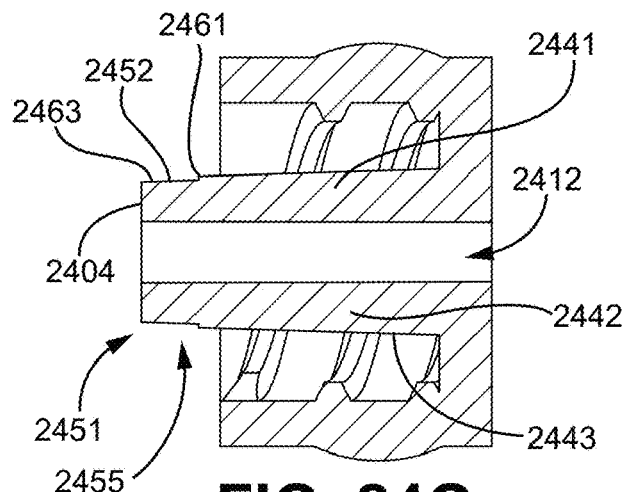
FIG. 24G is a cross-sectional view of the male luer connector of FIG. 24A along line G-G of FIG. 24F
Figure 24H:
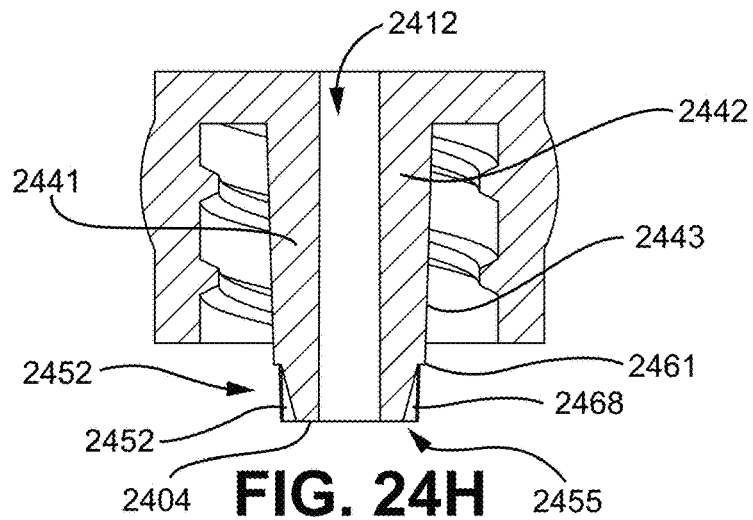
FIG. 24H is a cross-sectional view of the male luer connector of FIG. 24A along line H-H of FIG. 24F

The channels 2467 affect confinement of microbes within the distal recess because the channels 2467 provide a restricted space in which microbes can be trapped between the distal tip surface 2452 and an inside surface of a female luer. The apex 2464 of the blades 2463 provide a maximum outer diameter of the distal tip 2455, and the troughs 2468 of the channels 2467 provide a minimum outer diameter of the distal tip 2455. Although some fluid flow between adjacent channels 2467 is possible when the male luer 2441 is coupled with a female luer, the blades 2463 provide a partial physical barrier. As seen in FIGS. 24F and 24G, the distal tip 2455 has an outer diameter that is smaller than the outer diameter of the tapered sealing member 2442 at the tapered surface distal edge 2461, and the outer diameter of the distal tip 2455 smaller than the outer diameter of a distal taper line defined by the conical tapered sealing member 2442.

The distal tip 2455 has a plurality of blades 2463 separating a plurality of channels 2467. The blades 2463 have an apex 2464, and the channels 2467 have troughs 2468. In this example, the outer diameter of the apex 2464 is uniform, but the width of the blades 2463 increases toward the end face 2404 of the distal tip 2455. The outer diameter of the troughs 2468 decreases from the proximal portion to the distal portion of the distal tip 2455, causing the taper in the trough 2468 seen in FIG. 24H.

Male Luer Connector with Blade Apex Taper (FIGS. 25A-G)

Turning now to FIGS. 25A-G, a male luer connector 2501 includes a male luer 2541. The male luer 2541 comprises a tapered sealing member 2542. The tapered sealing member 2542 has a frustoconical shape that tapers from a larger outer diameter at the proximal portion of the tapered sealing member 2542 to a smaller outer diameter at the distal portion of the tapered sealing member near the tapered surface distal edge 2561. The tapered sealing member 2542 has a tapered sealing surface 2543 that is configured to mate with a female luer to create a fluid tight fit. The male luer connector 2501 further includes threads 2502 that allow the male luer connector 2501 to couple with a female luer connector. A lumen 2512 runs through the male luer connector 2501.

The male luer 2541 includes a distal tip 2555 with an end face 2504. The distal tip 2555 of the male luer 2541 is recessed from the distal line of taper of the tapered sealing member 2542. A distal recess 2551 is formed by a recessed portion of the distal tip 2555. The distal tip surface 2552 of the distal tip 2555 defines an outer diameter that is smaller than the outer diameter of the extension of the tapered sealing surface 2543.

The male luer 2541 includes a tapered surface distal edge 2561 that defines a proximal edge of the distal tip 2555. In some examples, an antimicrobial agent is applied to the distal tip surface 2552 by coating, spraying, or dipping the distal tip 2555 with an antimicrobial agent, although other methods of applying antimicrobial agent are contemplated and are within the scope of the technology. In some examples, antimicrobial agent is also applied to the tapered sealing surface 2543. An antimicrobial agent on the distal tip surface 2552 of the distal tip 2555 kills microbes within the distal recess 2551 between the surface of the female luer and the distal tip surface 2552. The distal recess 2551 is designed to confine the antimicrobial agent between the inner surface of a female luer and the distal tip surface 2552 so that microbes are exposed to a high antimicrobial concentration.

The male luer 2541 further includes multiple blades 2563 arrayed around the distal tip 2555 of the male luer 2541. Between the blades 2563 are a plurality of channels 2567. In the example of FIG. 25, the blades 2563 are elongated projections arranged around the axis of the tapered sealing member 2542, and the channels 2567 are elongated recesses disposed between the blades 2563 and running parallel to the lumen 2512. The blades 2563 and channels 2567 form alternating apexes 2564 and troughs 2568. The distal tip surface 2552 of the distal tip 2555 is defined by the blades 2563 and channels 2567. An antimicrobial agent on the distal tip surface 2552 can be stored within the volumes between the blades 2563.

During insertion of the male luer 2541 into a female luer, portions of the distal tip 2555 may come in contact with the inside surface of the female luer. The apex 2564 of each blade 2563 may come in contact with the female luer surface, but the troughs 2568 of the channels 2567 will not come in contact with the female luer surface. Thus, in comparison to the tapered surface distal edge 2561, the blades 2563 have a relatively smaller surface area near the end face 2504 of the distal tip 2555. This minimizes the amount of ingress of microbes that can be attributed to microbes being pushed into the body of the female luer by the male luer 2541.

Figure 25E:
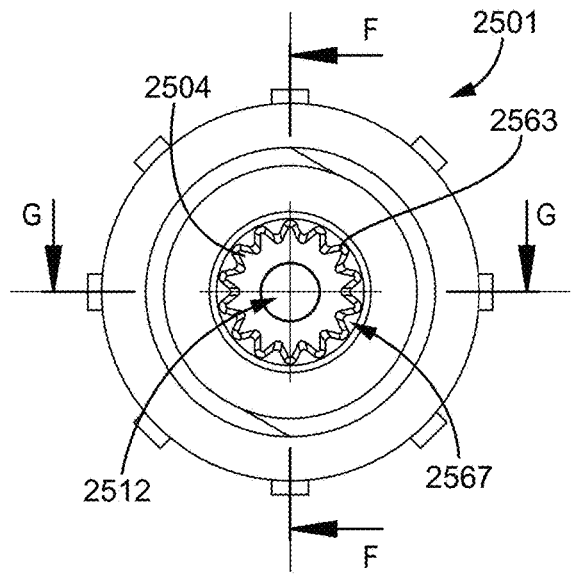
FIG. 25E is an end view of the male luer connector of FIG. 25A.
Figure 25F:
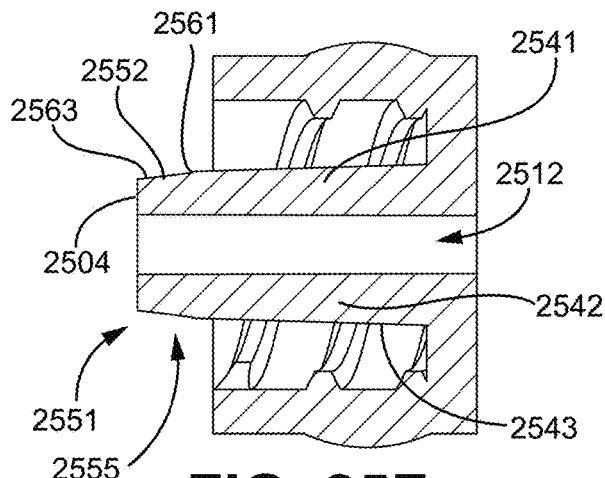
FIG. 25F is a cross-sectional view of the male luer connector of FIG. 25A along line F-F of FIG. 25E.
Figure 25G:
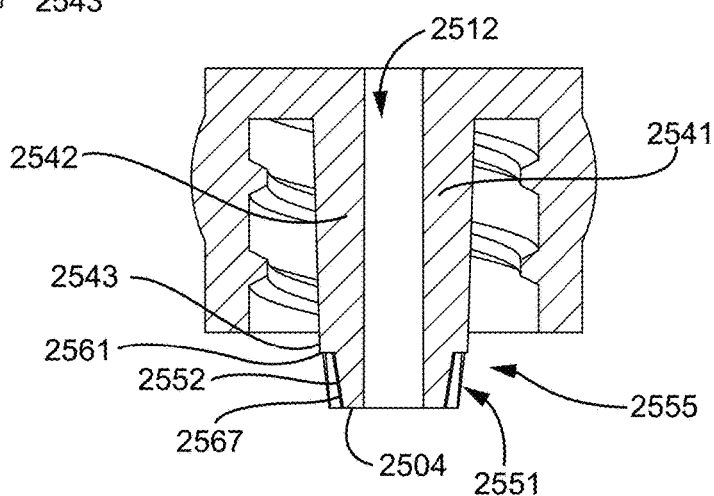
FIG. 25G is a cross-sectional view of the male luer connector of FIG. 25A along line G-G of FIG. 25E.

The channels 2567 affect confinement of microbes within the distal recess because the channels 2567 provide a restricted space in which microbes can be trapped between the distal tip surface 2552 and an inside surface of a female luer. The apex 2564 of the blades 2563 provide a maximum outer diameter of the distal tip 2555, and the troughs 2568 of the channels 2567 provide a minimum outer diameter of the distal tip 2555. Although some fluid flow between adjacent channels 2567 is possible when the male luer 2541 is coupled with a female luer, the blades 2563 provide a partial physical barrier. As seen in FIGS. 25E and 25F, the distal tip 2555 has an outer diameter that is smaller than the outer diameter of the tapered sealing member 2542 at the tapered surface distal edge 2561, and the outer diameter of the distal tip 2555 is smaller than the outer diameter of a distal taper line defined by the conical tapered sealing member 2542.

The distal tip 2555 has a plurality of blades 2563 separating a plurality of channels 2567. In this example, both the apex 2564 of the blades 2563 and the troughs 2568 of the channels 2567 are tapered such that the outer diameter decreases toward the distal end face 2504 of the distal tip 2555.

Male Luer Connector with Distal Blade Taper (FIGS. 26A-G)

Turning now to FIGS. 26A-G, a male luer connector 2601 includes a male luer 2641. The male luer 2641 comprises a tapered sealing member 2642. The tapered sealing member 2642 has a frustoconical shape that tapers from a larger outer diameter at the proximal portion of the tapered sealing member 2642 to a smaller outer diameter at the distal portion of the tapered sealing member near the tapered surface distal edge 2661. The tapered sealing member 2642 has a tapered sealing surface 2643 that is configured to mate with a female luer to create a fluid tight fit. The male luer connector 2601 further includes threads 2602 that allow the male luer connector 2601 to couple with a female luer connector. A lumen 2612 runs through the male luer connector 2601.

The male luer 2641 includes a distal tip 2655 with an end face 2604. The distal tip 2655 of the male luer 2641 is recessed from the distal line of taper of the tapered sealing member 2642. A distal recess 2651 is formed by a recessed portion of the distal tip 2655. The distal tip surface 2652 of the distal tip 2655 defines an outer diameter that is smaller than the outer diameter of the extension of the tapered sealing surface 2643.

The male luer 2641 includes a tapered surface distal edge 2661 that defines a proximal edge of the distal tip 2655. In some examples, an antimicrobial agent is applied to the distal tip surface 2652 by coating, spraying, or dipping the distal tip 2655 with an antimicrobial agent, although other methods of applying antimicrobial agent are contemplated and are within the scope of the technology. In some examples, antimicrobial agent is also applied to the tapered sealing surface 2643. An antimicrobial agent on the distal tip surface 2652 of the distal tip 2655 kills microbes within the distal recess 2651 between the surface of the female luer and the distal tip surface 2652. The distal recess 2651 is designed to confine the antimicrobial agent between the inner surface of a female luer and the distal tip surface 2652 so that microbes are exposed to a high antimicrobial concentration.

The male luer 2641 further includes multiple blades 2663 arrayed around the distal tip 2655 of the male luer 2641. Between the blades 2663 are a plurality of channels 2667. In the example of FIG. 26, the blades 2663 are elongated projections arranged around the axis of the tapered sealing member 2642, and the channels 2667 are elongated recesses disposed between the blades 2663 and running parallel to the lumen 2612. The blades 2663 and channels 2667 form alternating apexes 2664 and troughs 2668. The distal tip surface 2652 of the distal tip 2655 is defined by the blades 2663 and channels 2667. An antimicrobial agent on the distal tip surface 2652 can be stored within the volumes between the blades 2663.

During insertion of the male luer 2641 into a female luer, portions of the distal tip 2655 may come in contact with the inside surface of the female luer. The apex 2664 of each blade 2663 may come in contact with the female luer surface, but the troughs 2668 of the channels 2667 will not come in contact with the female luer surface. Thus, in comparison to the tapered surface distal edge 2661, the blades 2663 have a relatively smaller surface area near the end face 2604 of the distal tip 2655. This minimizes the amount of ingress of microbes that can be attributed to microbes being pushed into the body of the female luer by the male luer 2641.

Figure 26E:
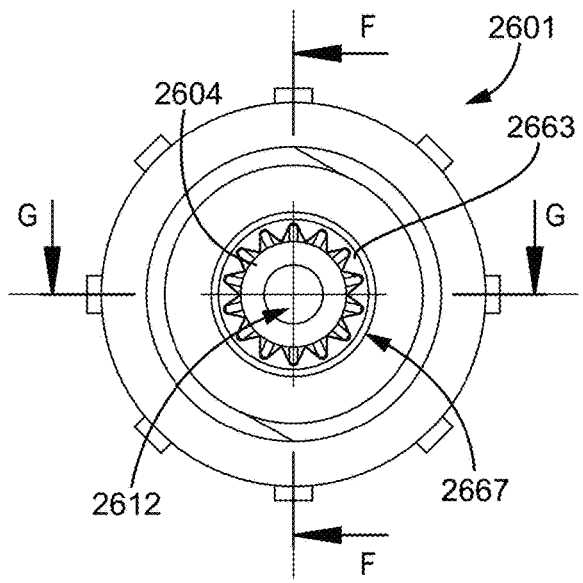
FIG. 26E is an end view of the male luer connector of FIG. 26A.
Figure 26F:
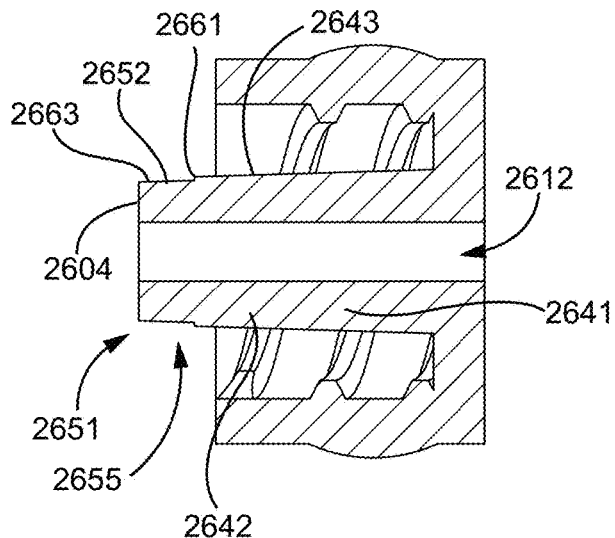
FIG. 26F is a cross-sectional view of the male luer connector of FIG. 26A along line F-F of FIG. 26E.
Figure 26G:
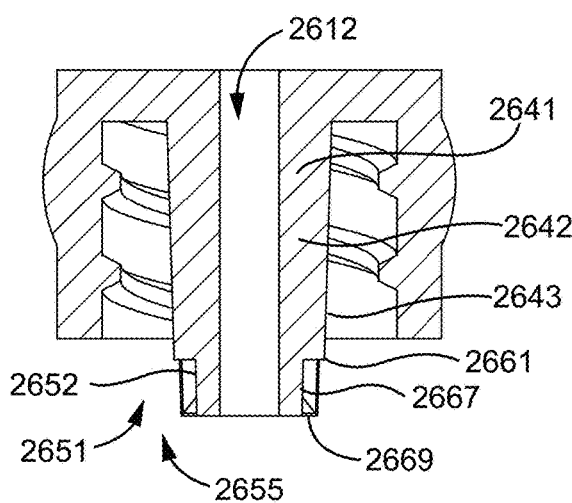
FIG. 26A is an isometric view of a male luer connector according to some examples.
FIG. 26B is a side view of the male luer connector of FIG. 26A.
FIG. 26C is a cross-sectional view of the male luer connector of FIG. 26A along line C-C of FIG. 26B.
FIG. 26D is a cross-sectional view of the male luer connector of FIG. 26A along line D-D of FIG. 26B.

The channels 2667 affect confinement of microbes within the distal recess because the channels 2667 provide a restricted space in which microbes can be trapped between the distal tip surface 2652 and an inside surface of a female luer. The apex 2664 of the blades 2663 provide a maximum outer diameter of the distal tip 2655, and the troughs 2668 of the channels 2667 provide a minimum outer diameter of the distal tip 2655. Although some fluid flow between adjacent channels 2667 is possible when the male luer 2641 is coupled with a female luer, the blades 2663 provide a partial physical barrier. As seen in FIGS. 26E and 26F, the distal tip 2655 has an outer diameter that is smaller than the outer diameter of the tapered sealing member 2642 at the tapered surface distal edge 2661, and the outer diameter of the distal tip 2655 is smaller than the outer diameter of a distal taper line defined by the conical tapered sealing member 2642.

The distal tip 2655 has a plurality of blades 2663 separating a plurality of channels 2667. In this example, the base of the blades 2663 are wide at a proximal end 2666 of the distal tip 2655 and gradually taper such that the blades 2663 are narrow at a distal end 2665 of the distal tip 2655. Conversely, the channels 2667 are narrow at the proximal end 2666 and widen toward the distal end 2665 of the distal tip 2655. In some examples, the blades 2663 include a bevel 2669 at the distal end 2665.

Male Luer Connector with Irregular Blade Length (FIGS. 27A-G)

Turning now to FIGS. 27A-G, a male luer connector 2701 includes a male luer 2741. The male luer 2741 comprises a tapered sealing member 2742. The tapered sealing member 2742 has a frustoconical shape that tapers from a larger outer diameter at the proximal portion of the tapered sealing member 2742 to a smaller outer diameter at the distal portion of the tapered sealing member near the tapered surface distal edge 2761. The tapered sealing member 2742 has a tapered sealing surface 2743 that is configured to mate with a female luer to create a fluid tight fit. The male luer connector 2701 further includes threads 2702 that allow the male luer connector 2701 to couple with a female luer connector. A lumen 2712 runs through the male luer connector 2701.

The male luer 2741 includes a distal tip 2755 with an end face 2704. The distal tip 2755 of the male luer 2741 is recessed from the distal line of taper of the tapered sealing member 2742. A distal recess 2751 is formed by a recessed portion of the distal tip 2755. The distal tip surface 2752 of the distal tip 2755 defines an outer diameter that is smaller than the outer diameter of the extension of the tapered sealing surface 2743.

The male luer 2741 includes a tapered surface distal edge 2761 that defines a proximal edge of the distal tip 2755. In some examples, an antimicrobial agent is applied to the distal tip surface 2752 by coating, spraying, or dipping the distal tip 2755 with an antimicrobial agent, although other methods of applying antimicrobial agent are contemplated and are within the scope of the technology. In some examples, antimicrobial agent is also applied to the tapered sealing surface 2743. An antimicrobial agent on the distal tip surface 2752 of the distal tip 2755 kills microbes within the distal recess 2751 between the surface of the female luer and the distal tip surface 2752. The distal recess 2751 is designed to confine the antimicrobial agent between the inner surface of a female luer and the distal tip surface 2752 so that microbes are exposed to a high antimicrobial concentration.

The male luer 2741 further includes multiple blades 2763 arrayed around the distal tip 2755 of the male luer 2741. Between the blades 2763 are a plurality of channels 2767. In the example of FIG. 27, the blades 2763 are elongated projections arranged around the axis of the tapered sealing member 2742, and the channels 2767 are elongated recesses disposed between the blades 2763 and running parallel to the lumen 2712. The blades 2763 and channels 2767 form alternating apexes 2764 and troughs 2768. The distal tip surface 2752 of the distal tip 2755 is defined by the blades 2763 and channels 2767. An antimicrobial agent on the distal tip surface 2752 can be stored within the volumes between the blades 2763.

During insertion of the male luer 2741 into a female luer, portions of the distal tip 2755 may come in contact with the inside surface of the female luer. The apex 2764 of each blade 2763 may come in contact with the female luer surface, but the troughs 2768 of the channels 2767 will not come in contact with the female luer surface. Thus, in comparison to the tapered surface distal edge 2761, the blades 2763 have a relatively smaller surface area near the end face 2704 of the distal tip 2755. This minimizes the amount of ingress of microbes that can be attributed to microbes being pushed into the body of the female luer by the male luer 2741.

Figure 27E:
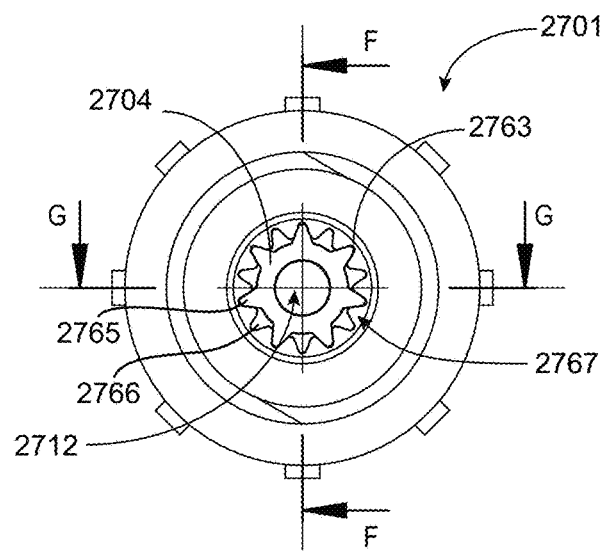
Figure 27F:
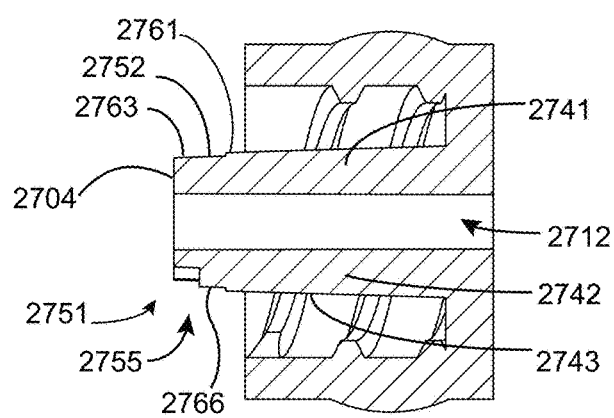
Figure 27G:
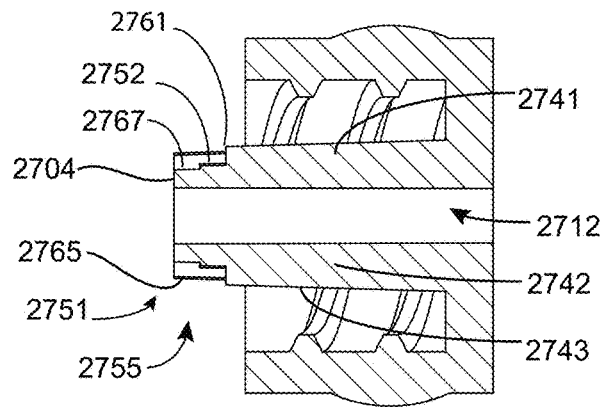

The channels 2767 affect confinement of microbes within the distal recess because the channels 2767 provide a restricted space in which microbes can be trapped between the distal tip surface 2752 and an inside surface of a female luer. The apex 2764 of the blades 2763 provide a maximum outer diameter of the distal tip 2755, and the troughs 2768 of the channels 2767 provide a minimum outer diameter of the distal tip 2755. Although some fluid flow between adjacent channels 2767 is possible when the male luer 2741 is coupled with a female luer, the blades 2763 provide a partial physical barrier. As seen in FIGS. 27E and 27F, the distal tip 2755 has an outer diameter that is smaller than the outer diameter of the tapered sealing member 2742 at the tapered surface distal edge 2761, and the outer diameter of the distal tip 2755 is smaller than the outer diameter of a distal taper line defined by the conical tapered sealing member 2742.

In this example, the distal tip 2755 includes a plurality of elongated blades 2765 and a plurality of truncated blades 2766.

Male Luer Connector with Zero-Clearance Blades (FIGS. 28A-F)

Turning now to FIGS. 28A-F, a male luer connector 2801 includes a male luer 2841. The male luer 2841 comprises a tapered sealing member 2842. The tapered sealing member 2842 has a frustoconical shape that tapers from a larger outer diameter at the proximal portion of the tapered sealing member 2842 to a smaller outer diameter at the distal portion of the tapered sealing member near the tapered surface distal edge 2861. The tapered sealing member 2842 has a tapered sealing surface 2843 that is configured to mate with a female luer to create a fluid tight fit. The male luer connector 2801 further includes threads 2802 that allow the male luer connector 2801 to couple with a female luer connector. A lumen 2812 runs through the male luer connector 2801.

The male luer 2841 includes a distal tip 2855 with an end face 2804. As seen in FIG. 28F, a distal recess 2851 is formed by a recessed portion of the distal tip 2855.

The male luer 2841 includes a tapered surface distal edge 2861 that defines a proximal edge of the distal tip 2855. In some examples, an antimicrobial agent is applied to the distal tip surface 2852 by coating, spraying, or dipping the distal tip 2855 with an antimicrobial agent, although other methods of applying antimicrobial agent are contemplated and are within the scope of the technology. In some examples, antimicrobial agent is also applied to the tapered sealing surface 2843. An antimicrobial agent on the distal tip surface 2852 of the distal tip 2855 kills microbes captured between the surface of the female luer and the distal tip surface 2852. The distal recess 2851 is designed to confine the antimicrobial agent between the inner surface of a female luer and the distal tip surface 2852 so that microbes are exposed to a high antimicrobial concentration.

The male luer 2841 further includes multiple blades 2863 arrayed around the distal tip 2855 of the male luer 2841. Between the blades 2863 are a plurality of channels 2867. In the example of FIG. 28, the blades 2863 are elongated projections arranged around the axis of the tapered sealing member 2842, and the channels 2867 are elongated recesses disposed between the blades 2863 and running parallel to the lumen 2812. The blades 2863 and channels 2867 form alternating apexes 2864 and troughs 2868. The distal tip surface 2852 of the distal tip 2855 is defined by the blades 2863 and channels 2867. An antimicrobial agent on the distal tip surface 2852 can be stored within the volumes between the blades 2863.

During insertion of the male luer 2841 into a female luer, portions of the distal tip 2855 may come in contact with the inside surface of the female luer. The apex 2864 of each blade 2863 may come in contact with the female luer surface, but the troughs 2868 of the channels 2867 will not come in contact with the female luer surface. Thus, in comparison to the tapered surface distal edge 2861, the blades 2863 have a relatively smaller surface area near the end face 2804 of the distal tip 2855. This minimizes the amount of ingress of microbes that can be attributed to microbes being pushed into the body of the female luer by the male luer 2841.

The channels 2867 affect confinement of microbes within the distal recess because the channels 2867 provide a restricted space in which microbes can be trapped between the distal tip surface 2852 and an inside surface of a female luer. The apex 2864 of the blades 2863 provide a maximum outer diameter of the distal tip 2855, and the troughs 2868 of the channels 2867 provide a minimum outer diameter of the distal tip 2855. The blades 2863 provide a physical barrier between adjacent channels 2867 when the male luer 2841 is mated with a female luer. As seen in FIGS. 28D and 28E, the outer diameter of the distal tip 2855 is the same as the outer diameter of the tapered sealing member 2842 at the apex 2864 of the blades 2863. As seen in FIG. 28F, the outer diameter of the distal tip 2855 is smaller than the outer diameter of the tapered sealing member 2842 at the trough 2868 of the channels 2867.

In this example, the apex 2864 of each blade 2863 has an outer diameter that follows the taper line of the tapered sealing member 2842. When the male luer connector 2801 is coupled with a female luer connector such that the male and female luers form a fluid tight fit, the apex 2864 of each blade 2863 contacts the inner surface of the female luer.

The distal tip 2855 includes a distal recess 2851. In this example, the distal recess is present inside of the volume of the channels 2867 created between the blades 2863, where the outer diameter of the distal tip 2855 is inside the line of taper of the tapered sealing member 2842.

Male Luer Connector with Threaded Blades (FIGS. 29A-G)

Turning now to FIGS. 29A-G, a male luer connector 2901 includes a male luer 2941. The male luer 2941 comprises a tapered sealing member 2942. The tapered sealing member 2942 has a frustoconical shape that tapers from a larger outer diameter at the proximal portion of the tapered sealing member 2942 to a smaller outer diameter at the distal portion of the tapered sealing member near the tapered surface distal edge 2961. The tapered sealing member 2942 has a tapered sealing surface 2943 that is configured to mate with a female luer to create a fluid tight fit. The male luer connector 2901 further includes threads 2902 that allow the male luer connector 2901 to couple with a female luer connector. A lumen 2912 runs through the male luer connector 2901.

The male luer 2941 includes a distal tip 2955 with an end face 2904. As seen in FIGS. 29F and 29G, a distal recess 2951 is formed by a recessed portion of the distal tip 2955.

The male luer 2941 includes a tapered surface distal edge 2961 that defines a proximal edge of the distal tip 2955. In some examples, an antimicrobial agent is applied to the distal tip surface 2952 by coating, spraying, or dipping the distal tip 2955 with an antimicrobial agent, although other methods of applying antimicrobial agent are contemplated and are within the scope of the technology. In some examples, antimicrobial agent is also applied to the tapered sealing surface 2943. An antimicrobial agent on the distal tip surface 2952 of the distal tip 2955 kills microbes captured between the surface of the female luer and the distal tip surface 2952. The distal recess 2951 is designed to confine the antimicrobial agent between the inner surface of a female luer and the distal tip surface 2952 so that microbes are exposed to a high antimicrobial concentration.

An antimicrobial agent on the distal tip surface 2952 can be stored within the volumes between the blades 2963.

The distal tip 2955 includes a plurality of blades 2963 that separate a plurality of channels 2967. The blades 2963 spiral around the axis of the lumen 2912, and the troughs 2968 of the channels 2967 follow the spiral. In this example, the apex 2964 of each blade 2963 has an outer diameter that follows the line of taper of the tapered sealing member 2942. Thus, when the male luer connector 2901 is coupled with a female luer connector such that the male and female luers form a fluid tight fit, the apex 2964 of each blade 2963 contacts the inner surface of the female luer.

In some examples, the blades 2963 have a threaded pitch that is the same as the pitch of the threads 2902 inside of the male luer connector 2901. Rotating the male luer connector 2901 around the axis of the lumen 2912 when inserting the male luer 2941 into a female luer causes the blades 2963 to rotate along with the male luer 2941. From the perspective shown in FIG. 29E, the male luer connector 2901 would move in a counterclockwise direction. The blades 2963 have a leading edge 2981 that can contact the female luer inside diameter. In this case, the apex 2964 serves as an extension of the tapered surface distal edge 2961. This rotation can allow the leading edge 2981 of the blades 2963 to act like a ramp, pushing any particles (such as microbes) on the surface of the female luer in a proximal direction.

The distal tip 2955 includes a distal recess 2951. In this example, the distal recess 2951 is present inside of the volume of the channels 2967 created between the blades 2963. As noted above, the leading edge 2981 can act as a ramp to push particles in a proximal direction, away from the end face 2904 of the distal tip 2955. An antimicrobial agent present on the distal tip surface 2952 of the distal tip 2955 can be dispersed inside the channels 2967 that form the distal recess 2951.

The channels 2967 affect confinement of microbes within the distal recess 2951 because the channels 2967 provide a restricted space in which microbes can be trapped between the distal tip surface 2952 and an inside surface of a female luer. The apex 2964 of the blades 2963 provide a maximum outer diameter of the distal tip 2955, and the troughs 2968 of the channels 2967 provide a minimum outer diameter of the distal tip 2955. The blades 2963 provide a physical barrier between adjacent channels 2967 when the male luer 2941 is mated with a female luer. The outer diameter of the distal tip 2955 is the same as the outer diameter of the tapered sealing member 2942 at the apex 2964 of the blades 2963. As seen in FIGS. 29F and 29G, the outer diameter of the distal tip 2955 is smaller than the outer diameter of the tapered sealing member 2942 at the trough 2968 of the channels 2967.

Male Luer Connector with Proximal Trap (FIGS. 30A-F)

Turning now to FIGS. 30A-F, a male luer connector 3001 includes a male luer 3041. The male luer 3041 comprises a tapered sealing member 3042. The tapered sealing member 3042 has a frustoconical shape that tapers from a larger outer diameter at the proximal portion of the tapered sealing member 3042 to a smaller outer diameter at the distal portion of the tapered sealing member near the tapered surface distal edge 3061. The tapered sealing member 3042 has a tapered sealing surface 3043 that is configured to mate with a female luer to create a fluid tight fit. The male luer connector 3001 further includes threads 3002 that allow the male luer connector 3001 to couple with a female luer connector. A lumen 3012 runs through the male luer connector 3001.

The male luer 3041 includes a distal tip 3055 with an end face 3004. The distal tip 3055 of the male luer 3041 is recessed from the distal line of taper of the tapered sealing member 3042. A distal recess 3051 is formed by a recessed portion of the distal tip 3055. The distal tip surface 3052 of the distal tip 3055 defines an outer diameter that is smaller than the outer diameter of the extension of the tapered sealing surface 3043.

In some examples, an antimicrobial agent is applied to the distal tip surface 3052 by coating, spraying, or dipping the distal tip 3055 with an antimicrobial agent, although other methods of applying antimicrobial agent are contemplated and are within the scope of the technology. In some examples, antimicrobial agent is also applied to the tapered sealing surface 3043. An antimicrobial agent on the distal tip surface 3052 of the distal tip 3055 kills microbes within the distal recess 3051 between the surface of the female luer and the distal tip surface 3052. The distal recess 3051 is designed to confine the antimicrobial agent between the inner surface of a female luer and the distal tip surface 3052 so that microbes are exposed to a high antimicrobial concentration.

The distal recess 3051 affects confinement of microbes because the distal recess 3051 provides a restricted space in which microbes can be trapped between the distal tip surface 3052 and an inside surface of a female luer. As seen in FIGS. 30E and 30F, the distal tip 3055 has an outer diameter that is smaller than the outer diameter of the tapered sealing member 3042 at the tapered surface distal edge 3061, and the outer diameter of the distal tip 3055 is smaller than the outer diameter of a distal taper line defined by the conical tapered sealing member 3042.

The distal tip 3055 has a distal tip surface 3052 and a distal recess 3051. In this example, the distal tip surface 3052 does not include blades. The male luer 3041 has a tapered surface distal edge 3061 at a distal end of the tapered sealing member 3042. The tapered surface distal edge 3061 has a tapered surface distal edge face 3062. A proximal trap 3071 is defined between the distal tip surface 3052 and the proximal trap walls 3073. The proximal trap 3071 is a cavity that is bounded on multiple sides. The proximal trap 3071 opens on the distal recess 3051. The proximal trap is adjacent to the tapered surface distal edge face 3062. As will be discussed below in relation to FIGS. 38 and 39, an antimicrobial agent can be contained inside of the proximal trap 3071.

The proximal trap 3071 stores an antimicrobial agent within the annular cavity defined by the proximal trap 3071. In some examples, microbes reside near the interface between the tapered surface distal edge 3061 and a surface of a female luer. The antimicrobial agent stored in the proximal trap 3071 ensures that the concentration of the antimicrobial agent remains high (up to the level of saturation) in the vicinity of microbes.

Both the proximal trap 3071 and the distal recess 3051 are designed to minimize washout of the antimicrobial agent from the volume created between the female luer surface and the distal tip surface 3052. The proximal trap 3071 has no separate entrance and exit. The antimicrobial agent on the surface of the proximal trap wall 3073 will diffuse out of the proximal trap 3071 after the male luer 3041 has been installed inside a female luer. There are differences between confinement of microbes and washout of the antimicrobial agent from the distal recess 3051. Confinement keeps the antimicrobial agent within the distal recess 3051 while fluid flows through the lumen 3012. Washout refers to preventing the antimicrobial agent from being washed away from the distal recess 3051 into the lumen of the female luer while the male luer connector is coupled with the female luer connector. The proximal trap 3071 prevents or minimizes fluid flow within the volume of the proximal trap 3071 because there is no through path to the body of the female luer lumen. Therefore, the antimicrobial agent is not readily washed away from the proximal trap 3071.

Male Luer Connector with Plurality of Proximal Cavities (FIGS. 31A-G)

Turning now to FIGS. 31A-G, a male luer connector 3101 includes a male luer 3141. The male luer 3141 comprises a tapered sealing member 3142. The tapered sealing member 3142 has a frustoconical shape that tapers from a larger outer diameter at the proximal portion of the tapered sealing member 3142 to a smaller outer diameter at the distal portion of the tapered sealing member near the tapered surface distal edge 3161. The tapered sealing member 3142 has a tapered sealing surface 3143 that is configured to mate with a female luer to create a fluid tight fit. The male luer connector 3101 further includes threads 3102 that allow the male luer connector 3101 to couple with a female luer connector. A lumen 3112 runs through the male luer connector 3101.

The male luer 3141 includes a distal tip 3155 with an end face 3104. The distal tip 3155 of the male luer 3141 is recessed from the distal line of taper of the tapered sealing member 3142. A distal recess 3151 is formed by a recessed portion of the distal tip 3155. The distal tip surface 3152 of the distal tip 3155 defines an outer diameter that is smaller than the outer diameter of the extension of the tapered sealing surface 3143.

In some examples, an antimicrobial agent is applied to the distal tip surface 3152 by coating, spraying, or dipping the distal tip 3155 with an antimicrobial agent, although other methods of applying antimicrobial agent are contemplated and are within the scope of the technology. In some examples, antimicrobial agent is also applied to the tapered sealing surface 3143. An antimicrobial agent on the distal tip surface 3152 of the distal tip 3155 kills microbes within the distal recess 3151 between the surface of the female luer and the distal tip surface 3152. The distal recess 3151 is designed to confine the antimicrobial agent between the inner surface of a female luer and the distal tip surface 3152 so that microbes are exposed to a high antimicrobial concentration.

The distal recess 3151 affects confinement of microbes because the distal recess 3151 provides a restricted space in which microbes can be trapped between the distal tip surface 3152 and an inside surface of a female luer. As seen in FIG. 31F, the distal tip 3155 has an outer diameter that is smaller than the outer diameter of the tapered sealing member 3142 at the tapered surface distal edge 3161, and the outer diameter of the distal tip 3155 is smaller than the outer diameter of a distal taper line defined by the conical tapered sealing member 3142.

Like the example of FIG. 30, the tapered surface distal edge 3161 has a tapered surface distal edge face 3162. But the distal tip 3155 includes a plurality of proximal traps 3171 that are isolated from each other by proximal trap walls 3173. The proximal traps 3171 have no separate entrance and exit. Antimicrobial agent can be stored on the surface of the proximal trap walls 3173, and the antimicrobial agent will diffuse out of the proximal trap 3171 after the male luer 3141 has been installed inside a female luer.

Male Luer Connector with Blade and Plurality of Proximal Cavities (FIGS. 32A-G)

Turning now to FIGS. 32A-G, a male luer connector 3201 includes a male luer 3241. The male luer 3241 comprises a tapered sealing member 3242. The tapered sealing member 3242 has a frustoconical shape that tapers from a larger outer diameter at the proximal portion of the tapered sealing member 3242 to a smaller outer diameter at the distal portion of the tapered sealing member near the tapered surface distal edge 3261. The tapered sealing member 3242 has a tapered sealing surface 3243 that is configured to mate with a female luer to create a fluid tight fit. The male luer connector 3201 further includes threads 3202 that allow the male luer connector 3201 to couple with a female luer connector. A lumen 3212 runs through the male luer connector 3201.

The male luer 3241 includes a distal tip 3255 with an end face 3204. The distal tip 3255 of the male luer 3241 is recessed from the distal line of taper of the tapered sealing member 3242. A distal recess 3251 is formed by a recessed portion of the distal tip 3255. The distal tip surface 3252 of the distal tip 3255 defines an outer diameter that is smaller than the outer diameter of the extension of the tapered sealing surface 3243.

The male luer 3241 includes a tapered surface distal edge 3261 that defines a proximal edge of the distal tip 3255. In some examples, an antimicrobial agent is applied to the distal tip surface 3252 by coating, spraying, or dipping the distal tip 3255 with an antimicrobial agent, although other methods of applying antimicrobial agent are contemplated and are within the scope of the technology. In some examples, antimicrobial agent is also applied to the tapered sealing surface 3243. An antimicrobial agent on the distal tip surface 3252 of the distal tip 3255 kills microbes within the distal recess 3251 between the surface of the female luer and the distal tip surface 3252. The distal recess 3251 is designed to confine the antimicrobial agent between the inner surface of a female luer and the distal tip surface 3252 so that microbes are exposed to a high antimicrobial concentration.

The male luer 3241 further includes multiple blades 3263 arrayed around the distal tip 3255 of the male luer 3241. Between the blades 3263 are a plurality of channels 3267. In the example of FIG. 32, the blades 3263 are elongated projections arranged around the axis of the tapered sealing member 3242, and the channels 3267 are elongated recesses disposed between the blades 3263 and running parallel to the lumen 3212. The blades 3263 and channels 3267 form alternating apexes 3264 and troughs 3268. The distal tip surface 3252 of the distal tip 3255 is defined by the blades 3263 and channels 3267. An antimicrobial agent on the distal tip surface 3252 can be stored within the volumes between the blades 3263.

During insertion of the male luer 3241 into a female luer, portions of the distal tip 3255 may come in contact with the inside surface of the female luer. The apex 3264 of each blade 3263 may come in contact with the female luer surface, but the troughs 3268 of the channels 3267 will not come in contact with the female luer surface. Thus, in comparison to the tapered surface distal edge 3261, the blades 3263 have a relatively smaller surface area near the end face 3204 of the distal tip 3255. This minimizes the amount of ingress of microbes that can be attributed to microbes being pushed into the body of the female luer by the male luer 3241.

The channels 3267 affect confinement of microbes within the distal recess because the channels 3267 provide a restricted space in which microbes can be trapped between the distal tip surface 3252 and an inside surface of a female luer. The apex 3264 of the blades 3263 provide a maximum outer diameter of the distal tip 3255, and the troughs 3268 of the channels 3267 provide a minimum outer diameter of the distal tip 3255. Although some fluid flow between adjacent channels 3267 is possible when the male luer 3241 is coupled with a female luer, the blades 3263 provide a partial physical barrier. As seen in FIGS. 32E and 32F, the distal tip 3255 has an outer diameter that is smaller than the outer diameter of the tapered sealing member 3242 at the tapered surface distal edge 3261, and the outer diameter of the distal tip 3255 is smaller than the outer diameter of a distal taper line defined by the conical tapered sealing member 3242.

The male luer 3241 includes a tapered surface distal edge 3261 having a tapered surface distal edge face 3262. Like this example of FIG. 31, a plurality of proximal traps 3271 are formed within a plurality of proximal trap walls 3273 that are proximal to the tapered surface distal edge face 3262. This can be seen most clearly and FIG. 32G. Each proximal trap 3271 is isolated from the other proximal traps. Each proximal trap 3271 has only one entrance and exit, forming a cavity surrounded by the proximal trap walls 3273 on all sides. The proximal trap 3271 is defined between the distal tip surface 3252 and the proximal trap walls 3273. The proximal trap 3271 is a cavity that is bounded on multiple sides. The proximal trap 3271 opens on the distal recess 3251. The proximal trap is adjacent to the tapered surface distal edge face 3262. An antimicrobial agent can be contained inside of the proximal trap 3271.

Male Luer Cap with Blades (FIGS. 33A-F)

Turning now to FIGS. 33A-F, a male luer cap 3301 includes a male luer 3341. The male luer 3341 comprises a tapered sealing member 3342. The tapered sealing member 3342 has a frustoconical shape that tapers from a larger outer diameter at the proximal portion of the tapered sealing member 3342 to a smaller outer diameter at the distal portion of the tapered sealing member near the tapered surface distal edge 3361. The tapered sealing member 3342 has a tapered sealing surface 3343 that is configured to mate with a female luer to create a fluid tight fit. The male luer cap 3301 further includes threads 3302 that allow the male luer cap 3301 to couple with a female luer connector.

The male luer 3341 includes a distal tip 3355 with an end face 3304. The distal tip 3355 of the male luer 3341 is recessed from the distal line of taper of the tapered sealing member 3342. A distal recess 3351 is formed by a recessed portion of the distal tip 3355. The distal tip surface 3352 of the distal tip 3355 defines an outer diameter that is smaller than the outer diameter of the extension of the tapered sealing surface 3343.

The male luer 3341 includes a tapered surface distal edge 3361 that defines a proximal edge of the distal tip 3355. In some examples, an antimicrobial agent is applied to the distal tip surface 3352 by coating, spraying, or dipping the distal tip 3355 with an antimicrobial agent, although other methods of applying antimicrobial agent are contemplated and are within the scope of the technology. In some examples, antimicrobial agent is also applied to the tapered sealing surface 3343. An antimicrobial agent on the distal tip surface 3352 of the distal tip 3355 kills microbes within the distal recess 3351 between the surface of the female luer and the distal tip surface 3352. The distal recess 3351 is designed to confine the antimicrobial agent between the inner surface of a female luer and the distal tip surface 3352 so that microbes are exposed to a high antimicrobial concentration.

The male luer 3341 further includes multiple blades 3363 arrayed around the distal tip 3355 of the male luer 3341. Between the blades 3363 are a plurality of channels 3367. In the example of FIG. 33, the blades 3363 are elongated projections arranged around the axis of the tapered sealing member 3342, and the channels 3367 are elongated recesses disposed between the blades 3363. The blades 3363 and channels 3367 form alternating apexes 3364 and troughs 3368. The distal tip surface 3352 of the distal tip 3355 is defined by the blades 3363 and channels 3367. An antimicrobial agent on the distal tip surface 3352 can be stored within the volumes between the blades 3363.

During insertion of the male luer 3341 into a female luer, portions of the distal tip 3355 may come in contact with the inside surface of the female luer. The apex 3364 of each blade 3363 may come in contact with the female luer surface, but the troughs 3368 of the channels 3367 will not come in contact with the female luer surface. Thus, in comparison to the tapered surface distal edge 3361, the blades 3363 have a relatively smaller surface area near the end face 3304 of the distal tip 3355. This minimizes the amount of ingress of microbes that can be attributed to microbes being pushed into the body of the female luer by the male luer 3341.

The channels 3367 affect confinement of microbes within the distal recess because the channels 3367 provide a restricted space in which microbes can be trapped between the distal tip surface 3352 and an inside surface of a female luer. The apex 3364 of the blades 3363 provide a maximum outer diameter of the distal tip 3355, and the troughs 3368 of the channels 3367 provide a minimum outer diameter of the distal tip 3355. Although some fluid flow between adjacent channels 3367 is possible when the male luer 3341 is coupled with a female luer, the blades 3363 provide a partial physical barrier. As seen in FIGS. 33D and 33E, the distal tip 3355 has an outer diameter that is smaller than the outer diameter of the tapered sealing member 3342 at the tapered surface distal edge 3361, and the outer diameter of the distal tip 3355 is smaller than the outer diameter of a distal taper line defined by the conical tapered sealing member 3342.

The male luer cap 3301 does not include a lumen, as it is designed to prevent fluid flow out of a medical device having a female luer at the proximal end of the medical device. An antimicrobial agent can coat the distal tip surface 3352. In some examples, the antimicrobial agent can also coat the end face 3304. Although not shown in the drawings of FIG. 33, the male luer cap 3301 could further include one or more proximal traps similar to those described above.

Luer Coupler with Blades at Male Distal End (FIGS. 34A-F)

Turning now to FIGS. 34A-F, a luer coupler 3401 includes a male luer portion 3449 and a female luer portion 3489 integral with the male luer portion 3449. A lumen 3412 runs through both the female luer portion 3489 and the male luer portion 3449. The female luer portion 3489 of the luer coupler 3401 includes threads 3486 for coupling with a male luer connector. The female luer portion 3489 further includes a female luer tapered sealing surface 3488.

The male luer 3441 comprises a tapered sealing member 3442. The tapered sealing member 3442 has a frustoconical shape that tapers from a larger outer diameter at the proximal portion of the tapered sealing member 3442 to a smaller outer diameter at the distal portion of the tapered sealing member near the tapered surface distal edge 3461. The tapered sealing member 3442 has a tapered sealing surface 3443 that is configured to mate with a female luer to create a fluid tight fit. The luer coupler 3401 further includes threads 3402 that allow the luer coupler 3401 to couple with a female luer connector.

The male luer 3441 includes a distal tip 3455 with an end face 3404. The distal tip 3455 of the male luer 3441 is recessed from the distal line of taper of the tapered sealing member 3442. A distal recess 3451 is formed by a recessed portion of the distal tip 3455. The distal tip surface 3452 of the distal tip 3455 defines an outer diameter that is smaller than the outer diameter of the extension of the tapered sealing surface 3443.

The male luer 3441 includes a tapered surface distal edge 3461 that defines a proximal edge of the distal tip 3455. In some examples, an antimicrobial agent is applied to the distal tip surface 3452 by coating, spraying, or dipping the distal tip 3455 with an antimicrobial agent, although other methods of applying antimicrobial agent are contemplated and are within the scope of the technology. In some examples, antimicrobial agent is also applied to the tapered sealing surface 3443. An antimicrobial agent on the distal tip surface 3452 of the distal tip 3455 kills microbes within the distal recess 3451 between the surface of the female luer and the distal tip surface 3452. The distal recess 3451 is designed to confine the antimicrobial agent between the inner surface of a female luer and the distal tip surface 3452 so that microbes are exposed to a high antimicrobial concentration.

The male luer 3441 further includes multiple blades 3463 arrayed around the distal tip 3455 of the male luer 3441. Between the blades 3463 are a plurality of channels 3467. In the example of FIG. 34, the blades 3463 are elongated projections arranged around the axis of the tapered sealing member 3442, and the channels 3467 are elongated recesses disposed between the blades 3463 and running parallel to the lumen 3412. The blades 3463 and channels 3467 form alternating apexes 3464 and troughs 3468. The distal tip surface 3452 of the distal tip 3455 is defined by the blades 3463 and channels 3467. An antimicrobial agent on the distal tip surface 3452 can be stored within the volumes between the blades 3463.

During insertion of the male luer 3441 into a female luer, portions of the distal tip 3455 may come in contact with the inside surface of the female luer. The apex 3464 of each blade 3463 may come in contact with the female luer surface, but the troughs 3468 of the channels 3467 will not come in contact with the female luer surface. Thus, in comparison to the tapered surface distal edge 3461, the blades 3463 have a relatively smaller surface area near the end face 3404 of the distal tip 3455. This minimizes the amount of ingress of microbes that can be attributed to microbes being pushed into the body of the female luer by the male luer 3441.

The channels 3467 affect confinement of microbes within the distal recess because the channels 3467 provide a restricted space in which microbes can be trapped between the distal tip surface 3452 and an inside surface of a female luer. The apex 3464 of the blades 3463 provide a maximum outer diameter of the distal tip 3455, and the troughs 3468 of the channels 3467 provide a minimum outer diameter of the distal tip 3455. Although some fluid flow between adjacent channels 3467 is possible when the male luer 3441 is coupled with a female luer, the blades 3463 provide a partial physical barrier. As seen in FIGS. 34C and 34D, the distal tip 3455 has an outer diameter that is smaller than the outer diameter of the tapered sealing member 3442 at the tapered surface distal edge 3461, and the outer diameter of the distal tip 3455 is smaller than the outer diameter of a distal taper line defined by the conical tapered sealing member 3442.

Luer Coupler with Proximal Trap at Male Distal End (FIGS. 35A-F)

Turning now to FIGS. 35A-F, a luer coupler 3501 includes a male luer portion 3549 and a female luer portion 3589 integral with the male luer portion 3549. A lumen 3512 runs through both the female luer portion 3589 and the male luer portion 3549. The female luer portion 3589 of the luer coupler 3501 includes threads 3586 for coupling with a male luer connector. The female luer portion 3589 further includes a female luer tapered sealing surface 3588.

The male luer 3541 comprises a tapered sealing member 3542. The tapered sealing member 3542 has a frustoconical shape that tapers from a larger outer diameter at the proximal portion of the tapered sealing member 3542 to a smaller outer diameter at the distal portion of the tapered sealing member near the tapered surface distal edge 3561. The tapered sealing member 3542 has a tapered sealing surface 3543 that is configured to mate with a female luer to create a fluid tight fit. The luer coupler 3501 further includes threads 3502 that allow the luer coupler 3501 to couple with a female luer connector.

The male luer 3541 includes a distal tip 3555 with an end face 3504. The distal tip 3555 of the male luer 3541 is recessed from the distal line of taper of the tapered sealing member 3542. A distal recess 3551 is formed by a recessed portion of the distal tip 3555. The distal tip surface 3552 of the distal tip 3555 defines an outer diameter that is smaller than the outer diameter of the extension of the tapered sealing surface 3543.

The male luer 3541 includes a tapered surface distal edge 3561 that defines a proximal edge of the distal tip 3555. In some examples, an antimicrobial agent is applied to the distal tip surface 3552 by coating, spraying, or dipping the distal tip 3555 with an antimicrobial agent, although other methods of applying antimicrobial agent are contemplated and are within the scope of the technology. In some examples, antimicrobial agent is also applied to the tapered sealing surface 3543. An antimicrobial agent on the distal tip surface 3552 of the distal tip 3555 kills microbes within the distal recess 3551 between the surface of the female luer and the distal tip surface 3552. The distal recess 3551 is designed to confine the antimicrobial agent between the inner surface of a female luer and the distal tip surface 3552 so that microbes are exposed to a high antimicrobial concentration.

The tapered surface distal edge 3561 has a tapered surface distal edge face 3562. A proximal trap 3571 is defined between the distal tip surface 3552 and the proximal trap walls 3573. The proximal trap 3571 is a cavity that is bounded on multiple sides. The proximal trap 3571 opens on the distal recess 3551. The proximal trap is adjacent to the tapered surface distal edge face 3562. As will be discussed below in relation to FIGS. 38 and 39, an antimicrobial agent can be contained inside of the proximal trap 3571.

The proximal trap 3571 stores an antimicrobial agent within the annular cavity defined by the proximal trap 3571. In some examples, microbes reside near the interface between the tapered surface distal edge 3561 and a surface of a female luer. The antimicrobial agent stored in the proximal trap 3571 ensures that the concentration of the antimicrobial agent remains high (up to the level of saturation) in the vicinity of microbes.

Both the proximal trap 3571 and the distal recess 3551 are designed to minimize washout of the antimicrobial agent from the volume created between the female luer surface and the distal tip surface 3552. The proximal trap 3571 has no separate entrance and exit. The antimicrobial agent on the surface of the proximal trap wall 3573 will diffuse out of the proximal trap 3571 after the male luer 3541 has been installed inside a female luer. The proximal trap 3571 prevents or minimizes fluid flow within the volume of the proximal trap 3571 because there is no through path to the body of the female luer lumen. Therefore, the antimicrobial agent is not readily washed away from the proximal trap 3571.

As seen in FIG. 35D, the distal tip 3555 has an outer diameter that is smaller than the outer diameter of the tapered sealing member 3542 at the tapered surface distal edge 3561, and the outer diameter of the distal tip 3555 is smaller than the outer diameter of a distal taper line defined by the conical tapered sealing member 3542.

Luer Couplers Coupled with Male and Female Luers (FIGS. 36-37)

FIG. 36 shows the luer coupler 3501 coupled between a male luer connector 3611 and a female luer 3691. FIG. 37 shows a luer coupler 3701 coupled between the male luer connector 3611 and the female luer 3691. The male luer connector 3611 has a male luer 3641 and a lumen 3621. The male luer 3641 is mated with the female luer tapered sealing surface 3588 of the luer coupler 3501. The female luer 3691 has a female luer tapered sealing surface 3688 and a lumen 3695.

The luer coupler 3701 is similar to the luer coupler 3501, with similar features and functions. The male luer portion 3749 of the luer coupler 3501 is similar to the male luer connector 2001 described in connection with FIGS. 20A-G, described above.

The luer coupler 3701 includes a male luer portion 3749 and a female luer portion 3789 integral with the male luer portion 3749. A lumen 3712 runs through both the female luer portion 3789 and the male luer portion 3749. The female luer portion 3789 further includes a female luer tapered surface 3788.

The luer coupler 3701 includes a male luer 3741. The male luer 3741 comprises a tapered sealing member 3742 with a tapered surface distal edge 3761. The luer coupler 3701 further includes threads 3702 that allow the luer coupler 3701 to couple with a female luer connector. A lumen 3712 runs through the luer coupler 3701.

The male luer 3741 includes a distal tip 3755 with a distal recess 3751 and an end face 3704. The distal tip surface 3752 of the distal tip 3755 defines an outer diameter that is smaller than the outer diameter of the extension of the tapered sealing surface 3743.

The tapered surface distal edge 3761 defines a proximal edge of the distal tip 3755. In some examples, an antimicrobial agent is applied to the distal tip surface 3752 by coating, spraying, or dipping the distal tip 3755 with an antimicrobial agent, although other methods of applying antimicrobial agent are contemplated and are within the scope of the technology. In some examples, antimicrobial agent is also applied to the tapered sealing surface 3743.

The male luer 3741 further includes multiple blades 3763 arrayed around the distal tip 3755 of the male luer 3741. Between the blades 3763 are a plurality of channels 3767.

Fluid Flow Analysis of Male Connector (FIGS. 38-39)

FIGS. 38-39 are visual representations of mathematical modeling of steady-state flow simulations of fluid flowing through a coupled male and female luer, where the male luer includes a distal recess and a proximal trap proximal to the distal recess. Without wishing to be bound by theory, these models simulate a syringe delivering fluid to the female connector (FIG. 38) and an IV-drip delivery system (FIG. 39). The syringe load is characterized as a flow of 2 milliliters/seconds for up to five seconds. The IV drip load is characterized as a flow of 1 liter/hour for up to one hour. The simulation can be applied to systems such as the coupled male luer 3549 and female luer 3691 of FIG. 36.

FIG. 38 shows the operation of the system shown in FIG. 36. In FIG. 38, the male luer 3541 is inserted into the lumen 3695 of the female luer 3691. The tapered sealing surface 3543 of the male luer 3541 and the tapered sealing surface 3688 of the female luer 3691 form a male-female luer interface with a fluid tight seal. The distal tip 3555 of the male luer 3541 is set back from the female luer tapered sealing surface 3688.

The male luer 3541 has a distal recess 3551. The male luer 3541 includes a distal tip 3555 having a distal tip surface 3552. A cavity is formed between the distal tip surface 3552 and the tapered sealing surface 3688 of the female luer 3691. The cavity is also bounded by a tapered surface distal edge face 3562 adjacent to tapered surface distal edge 3561. In the example of FIG. 38, the male luer 3541 further includes a proximal trap 3571 defined by proximal trap walls 3573.

A fluid passage is defined within the lumen 3512 of the male luer 3541 and the lumen 3695 of the female luer 3691. The fluid passage has multiple fluid flow regions. A bulk flow region 3801 is the space in which fluid travels through the connection of the male and female luers. A distal recess region 3802 is formed between the distal tip surface 3552 and the female luer tapered sealing surface 3688. A boundary region 3803 is situated between the bulk flow region 3801 and the recess region. A proximal trap region 3804 is situated proximal to the tapered surface distal edge face 3562.

The distal recess region 3802 contains a solid deposit of an antimicrobial agent, referred to as the load. An antimicrobial composition can be deposited in the proximal trap 3571 and on one or more of the surfaces 3552, 3573, and 3562. The distal recess region 3802 can be the predominant location at which surface-bound microbes are present within the luer connection.

The distal recess region 3802 confines recirculation of fluids while a fluid load passes through the luer connection.

The antimicrobial composition disperses into the fluidic recirculation. The recirculating fluid within the distal recess region 3802 recirculates the antimicrobial composition, which increases the antimicrobial concentration within this region and distributes the antimicrobial agent onto the inner surface of the female luer connector. The presence of antimicrobial agent along the inner surface of the female luer connector within the distal recess region prevents microbes located at the male-female interface from propagating along the wall of the female luer tapered sealing surface 3688.

Fluid flow through the design generates a set of three fluidic recirculations, or vortexes. These vortexes create a fluidic boundary between passing fluid and a microbial load located at the male-female interface edge. The three vortices can be described by their location. A proximal trap vortex contained in the proximal trap 3571 contains a large antimicrobial load. The distal recess vortex is located adjacent to the proximal trap vortex. A boundary vortex is sandwiched between the distal recess vortex and the stream of fluid passing through the bulk flow region 3801.

In the example of FIG. 38, vortexes are created in the boundary region 3803, the distal recess region 3802, and the proximal trap region 3804. Antimicrobial agent is contained and recirculated within each of these regions. In some examples, the proximal trap region 3804 contains a load of antimicrobial agent that is greater than can be dissolved into the distal recess region 3802 at saturation concentration; thus the proximal trap 3571 serves as an antimicrobial agent reservoir to maintain a high antimicrobial concentration. In some examples, the antimicrobial concentration can be around 200 micrograms per milliliter (μg/ml) of chlorhexidine.

FIG. 39 shows the operation of the system shown in FIG. 36, as described above, under IV drip conditions. A bulk flow region 3901 is the space in which fluid travels through the connection of the male and female luers. A distal recess region 3902 is formed between the distal tip surface 3552 and the female luer tapered sealing surface 3688. A boundary region 3903 is situated between the bulk flow region 3901 and the recess region. A proximal trap region 3904 is situated proximal to the tapered surface distal edge face 3562.

In the example of FIG. 39, vortexes are created in the boundary region 3903, the distal recess region 3902, and the proximal trap region 3904. Antimicrobial agent is contained and recirculated within each of these regions.

We claim:

1. A method for delivering an antimicrobial composition into an infusion device, the method comprising:

inserting a male connector having a male tapered surface into a female connector of the infusion device, the female connector having a female tapered surface, such that the male tapered surface engages the female tapered surface to form a substantially fluid-tight seal, the male connector having:

i) a distal tip having a distal end face;

ii) the distal tip having a recess surface proximal to the distal end face, wherein the recess surface is radially inward of a line of taper extending along, and distal of, the male tapered surface at a first taper angle relative to a central longitudinal axis of the male connector;

iii) a water-soluble antimicrobial composition positioned on the recess surface;

wherein, upon insertion of the male connector into the female connector, a cavity is formed between the recess surface and the female tapered surface, a fluid inside the infusion device at least partially fills the cavity, and at least a portion of the antimicrobial composition is dispersed within the fluid in the cavity; and iv) a fluid flow channel through the male connector.

2. The method for delivering an antimicrobial composition into an infusion device of claim 1, the male connector further comprising a tapered surface distal edge proximal to the distal tip of the male connector, the tapered surface distal edge being at the distal most end of the male tapered surface.

3. The method for delivering an antimicrobial composition into an infusion device of claim 2, wherein the tapered surface distal edge is proximal to at least part of the recess surface in the male connector.

4. The method for delivering an antimicrobial composition into an infusion device of claim 2, wherein the tapered surface distal edge has an inner diameter, the distal tip has an outer diameter, and the inner diameter of the tapered surface distal edge is greater than the outer diameter of the distal tip.

5. The method for delivering an antimicrobial composition into an infusion device of claim 2, wherein during insertion of the male connector into the female connector the tapered surface distal edge of the male connector contacts the female tapered surface of the female connector and tapered surface edge of the male connector and both rotates and moves distally along the female tapered surface.

6. The method for delivering an antimicrobial composition into an infusion device of claim 1, wherein the male connector is a distal end portion of a needleless connector.

7. The method for delivering an antimicrobial composition into an infusion device of claim 1, wherein the antimicrobial composition comprises chlorhexidine.

8. The method for delivering an antimicrobial composition into an infusion device of claim 7, wherein a portion of the antimicrobial composition dissolves into the fluid and forms a chlorhexidine precipitate on a portion of the tapered female surface.

9. The method for delivering an antimicrobial composition into an infusion device of claim 8, wherein the chlorhexidine precipitate is formed on a portion of the tapered female surface defining the cavity between the recess surface and female tapered surface.

10. The method for delivering an antimicrobial composition into an infusion device of claim 1, wherein the distal tip of the male connector has a diameter that is less than 95 percent of a diameter of a portion of the female tapered surface radially outward of the distal tip.

11. The method for delivering an antimicrobial composition into an infusion device of claim 1, wherein the cavity defines an annular volume between the male connector and the female connector.

12. The method for delivering an antimicrobial composition into an infusion device of claim 11, wherein the annular volume is between 1 and 10 micro liters in volume.

13. The method for delivering an antimicrobial composition into an infusion device of claim 1, wherein a plurality of blades extend radially outward from the male recess surface into the cavity to at least partially divide the cavity.

14. The method for delivering an antimicrobial composition into an infusion device of claim 1, wherein the first taper angle being equal to a second taper angle of the recess surface relative to the central longitudinal axis.

15. The method for delivering an antimicrobial composition into an infusion device of claim 1, further comprising a proximal trap.

16. The method for delivering an antimicrobial composition into an infusion device of claim 2, wherein the tapered surface distal edge is proximal to at least a portion of the recess surface.

17. The method for delivering an antimicrobial composition into an infusion device of claim 15, wherein a portion of the water-soluble antimicrobial composition is contained within the proximal trap.

18. A method for delivering an antimicrobial composition into an infusion device, the method comprising:
inserting a male connector having a male tapered surface into a female connector of the infusion device, the female connector having a female tapered surface, such that the male tapered surface engages the female tapered surface to form a fluid-tight seal, the male connector having:
i) a conical taper defined in part by the male tapered surface;
ii) a distal tip having an outer diameter that is less than 95 percent of an inner diameter of the female tapered surface at a point radially outward of the distal tip;
iii) the distal tip having a distal end face and a recess surface proximal to the distal end face of the male connector, the recess surface residing inside the conical taper;
iv) a tapered surface distal edge proximal to the distal end face, the tapered surface distal edge having an outer diameter greater than the outer diameter of the distal tip;
v) a fluid flow channel through the male connector; and
vi) a water-soluble antimicrobial composition positioned on the recess surface;
wherein upon insertion of the male connector into the female connector, an annular cavity is formed between the recess surface and the female tapered surface of the female connector, and
a fluid inside the infusion device at least partially fills the annular cavity, and at least a portion of the antimicrobial composition is dispersed within the fluid in the annular cavity;
wherein a proximal portion of the annular cavity is configured to collect microbes.

19. The method for delivering an antimicrobial composition into an infusion device of claim 18, wherein the annular cavity defines an annular volume between the male connector and the female connector, and wherein a portion of the antimicrobial composition dissolves into the fluid and forms a chlorhexidine precipitate on a portion of the tapered female surface.

20. The method for delivering an antimicrobial composition into an infusion device of claim 18, wherein a plurality of blades extend radially outward from the recess surface into the annular cavity to at least partially divide the annular cavity.

21. A method for delivering an antimicrobial composition into an infusion device, the method comprising:
inserting a male connector having a male tapered surface into a female connector of an infusion device, the female connector having a female tapered surface, such that the male tapered surface engages the female tapered surface to form a fluid-tight seal, the male connector having:
i) a conical taper defined in part by the male tapered surface;
ii) a distal tip having an outer diameter that is less than 95 percent of an inner diameter of the female tapered surface at a point radially outward of the distal tip;

iii) the distal tip having a distal end face and a recess surface proximal to the distal end face and inside the conical taper;
iv) a tapered surface distal edge proximal to the distal tip, the tapered surface distal edge having a radius greater than a radius of the distal tip;
v) a fluid flow channel through the male connector;
vi) a water-soluble antimicrobial composition positioned on the recess surface;
wherein, upon insertion of the male connector into the female connector, an annular cavity is formed between the recess surface and the female tapered surface of the female connector, the annular cavity having a proximal end and a distal end, a volume between the proximal end and the distal end, a width measured radially, and a length measured axially;
wherein the tapered surface distal edge at least partially defines the proximal end of the annular cavity, the distal end of the annular cavity is in fluid communication with a fluid lumen of the infusion device, and the width of the annular cavity is less than 50 percent of the length of the annular cavity; and
wherein a fluid inside the infusion device at least partially fills the annular cavity, and at least a portion of the antimicrobial composition is dispersed within the fluid in the annular cavity.

22. The method for delivering an antimicrobial composition into an infusion device of claim 21, further comprising a proximal trap.

23. The method for delivering an antimicrobial composition into an infusion device of claim 21, wherein a plurality of blades extend radially outward from the recess surface into the annular cavity to at least partially divide the annular cavity.

24. The method for delivering an antimicrobial composition into an infusion device of claim 21, wherein a portion of the antimicrobial composition dissolves into the fluid and forms a chlorhexidine precipitate on a portion of the tapered female surface.

25. A method for delivering an antimicrobial composition into a medical tube having a female connector with a female tapered surface, the method comprising:
inserting a male connector into the female connector such that a male tapered surface of the male connector mates with the female tapered surface, wherein the male connector includes:
i) an end face,
ii) a radially-outward-facing recess surface proximal to the end face and radially inward of a line of taper extending along, and distal of, the male tapered surface at a first taper angle relative to a central longitudinal axis of the male connector,
iii) a fluid flow channel, and
iv) a water-soluble antimicrobial composition on the recess surface, wherein upon insertion of the male connector into the female connector, a cavity is defined by the recess surface and the female tapered surface; and
upon inserting the male connector into the female connector, a fluid at least partially filling the cavity disperses at least a portion of the antimicrobial composition within the fluid in the cavity.

26. The method for delivering an antimicrobial composition into a medical tube having a female connector with a female tapered surface of claim 25, the male connector further comprising a tapered surface distal edge proximal to a distal end face of the male connector.

27. The method for delivering an antimicrobial composition into a medical tube having a female connector with a female tapered surface of claim 26, wherein the tapered surface distal edge is proximal to the recess surface in the male connector.

28. The method for delivering an antimicrobial composition into a medical tube having a female connector with a female tapered surface of claim 25, further comprising a proximal trap.

29. The method for delivering an antimicrobial composition into a medical tube having a female connector with a female tapered surface of claim 25, wherein a plurality of blades extend radially outward from the recess surface into the cavity to at least partially divide the cavity.

30. The method for delivering an antimicrobial composition into a medical tube having a female connector with a female tapered surface of claim 25, wherein a portion of the antimicrobial composition dissolves into the fluid and forms a chlorhexidine precipitate on a portion of the tapered female surface.

* * * * *